US011337851B2

(12) United States Patent
Jacobsen et al.

(10) Patent No.: US 11,337,851 B2
(45) Date of Patent: May 24, 2022

(54) DEVICES, SYSTEMS AND METHODS FOR ENDOVASCULAR TEMPERATURE CONTROL

(71) Applicant: Zoll Circulation, Inc., San Jose, CA (US)

(72) Inventors: John William Jacobsen, San Jose, CA (US); Ayan Majumdar, San Jose, CA (US); Sean W Yip, Mountain View, CA (US); Jeremy Thomas Dabrowiak, Santa Clara, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 404 days.

(21) Appl. No.: 16/052,551

(22) Filed: Aug. 1, 2018

(65) Prior Publication Data

US 2019/0133820 A1  May 9, 2019

Related U.S. Application Data

(63) Continuation-in-part of application No. PCT/US2018/016754, filed on Feb. 2, 2018, and a
(Continued)

(51) Int. Cl.
*A61F 7/12* (2006.01)
*A61F 7/00* (2006.01)
(Continued)

(52) U.S. Cl.
CPC ............... *A61F 7/12* (2013.01); *A61B 90/90* (2016.02); *A61F 7/0085* (2013.01); *A61F 2007/0054* (2013.01); *A61F 2007/0086* (2013.01); *A61F 2007/0093* (2013.01); *A61F 2007/0096* (2013.01); *A61F 2007/126* (2013.01);
(Continued)

(58) Field of Classification Search
CPC ............. A61B 90/90; A61F 2007/0054; A61F 2007/0086; A61F 2007/0093; A61F 2007/0096; A61F 2007/126; A61F 7/0085; A61F 7/12; A61M 2205/127; A61M 2205/6018; A61M 25/00
See application file for complete search history.

(56) References Cited

U.S. PATENT DOCUMENTS 1,459,112 A   6/1923  Mehl
1,857,031 A   5/1932  Schaffer
(Continued)

FOREIGN PATENT DOCUMENTS

CN    202942288        5/2013
DE    19531935 A1      2/1997
(Continued)

OTHER PUBLICATIONS

Behringer, et al., "Rapid Hypothermic Aortic Flush Can Achieve Survival without Brain Damage after 30 minutes Cardiac Arrest in Dogs", Anesthesiology, vol. 93, No. 6, Dec. 2000.
(Continued)

*Primary Examiner* — Tigist S Demie
(74) *Attorney, Agent, or Firm* — ZOLL Circulation, Inc.

(57) ABSTRACT

Devices, systems and methods for controlling a patient's body temperature by endovascular heat exchange and/or surface heat exchange.

14 Claims, 49 Drawing Sheets

Related U.S. Application Data continuation-in-part of application No. 15/594,541, filed on May 12, 2017, now Pat. No. 11,116,657, which is a continuation-in-part of application No. 15/423,581, filed on Feb. 2, 2017, now Pat. No. 11,185,440.

(51) Int. Cl.
*A61B 90/90* (2016.01)
*A61M 25/00* (2006.01)

(52) U.S. Cl.
CPC ....... *A61M 25/00* (2013.01); *A61M 2205/127* (2013.01); *A61M 2205/6018* (2013.01)

(56) References Cited

U.S. PATENT DOCUMENTS

| | | |
|---|---|---|
| 2,663,030 A | 12/1953 | Dahlberg |
| 2,673,987 A | 4/1954 | Upshaw et al. |
| 2,696,173 A | 12/1954 | Jensen |
| 2,893,324 A | 7/1959 | Isreeli et al. |
| 2,987,004 A | 6/1961 | Murray |
| 3,225,191 A | 12/1965 | Calhoun |
| 3,369,549 A | 2/1968 | Armao |
| 3,425,419 A | 2/1969 | Dato |
| 3,504,674 A | 4/1970 | Swenson et al. |
| 3,726,269 A | 4/1973 | Webster, Jr. |
| 3,744,555 A | 7/1973 | Fletcher et al. |
| 3,751,077 A | 8/1973 | Hiszpanski |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,231,707 A | 11/1980 | Tokorozawa et al. |
| 4,298,006 A | 11/1981 | Parks |
| 4,459,468 A | 7/1984 | Bailey |
| 4,532,414 A | 7/1985 | Shah et al. |
| 4,554,793 A | 11/1985 | Harding, Jr. |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,941,475 A | 7/1990 | Williams et al. |
| 5,092,841 A | 3/1992 | Spears |
| 5,096,393 A | 3/1992 | Van Steenderen et al. |
| 5,103,360 A | 4/1992 | Maeda |
| 5,106,360 A | 4/1992 | Ishiwara et al. |
| 5,192,274 A | 3/1993 | Bierman |
| 5,195,965 A | 3/1993 | Shantha |
| 5,211,631 A | 5/1993 | Sheaff |
| 5,269,758 A | 12/1993 | Taheri |
| 5,281,215 A | 1/1994 | Milder |
| 5,304,214 A | 4/1994 | DeFord et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,403,281 A | 4/1995 | O'Neill et al. |
| 5,433,740 A | 7/1995 | Yamaguchi |
| 5,437,673 A | 8/1995 | Baust et al. |
| 5,458,639 A | 10/1995 | Tsukashima et al. |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,624,392 A | 4/1997 | Saab |
| 5,634,907 A | 6/1997 | Rani et al. |
| 5,676,670 A | 10/1997 | Kim |
| 5,701,905 A | 12/1997 | Esch |
| 5,709,564 A | 1/1998 | Yamada et al. |
| 5,709,654 A | 1/1998 | Klatz et al. |
| 5,711,654 A | 1/1998 | Afflerbaugh |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,776,079 A | 7/1998 | Cope et al. |
| 5,788,647 A | 8/1998 | Eggers |
| 5,837,003 A | 11/1998 | Ginsburg |
| 5,862,675 A | 1/1999 | Scaringe et al. |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,110,139 A | 8/2000 | Loubser |
| 6,117,065 A | 9/2000 | Hastings et al. |
| 6,117,105 A | 9/2000 | Bresnaham et al. |
| 6,124,452 A | 9/2000 | DiMagno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,677 A | 11/2000 | Dobak, III |
| 6,231,594 B1 | 5/2001 | Dae |
| 6,283,940 B1 | 9/2001 | Mulholland |
| 6,299,599 B1 | 10/2001 | Pham et al. |
| 6,338,727 B1 | 1/2002 | Noda et al. |
| 6,383,144 B1 | 5/2002 | Mooney et al. |
| 6,409,747 B1 | 6/2002 | Gobin et al. |
| 6,416,533 B1 | 7/2002 | Gobin et al. |
| 6,428,563 B1 | 8/2002 | Keller |
| 6,436,130 B1 | 8/2002 | Philips et al. |
| 6,450,990 B1 | 9/2002 | Walker et al. |
| 6,464,716 B1 | 10/2002 | Dobak, III et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | LePivert |
| 6,554,791 B1 | 4/2003 | Cartledge et al. |
| 6,605,106 B2 | 8/2003 | Schwartz |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaiuolo et al. |
| 6,635,076 B1 | 10/2003 | Ginsburg |
| 6,679,906 B2 | 1/2004 | Hammack et al. |
| 6,685,733 B1 | 2/2004 | Dae et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,733,495 B1 | 5/2004 | Bek et al. |
| 6,740,109 B2 | 5/2004 | Dobak, III |
| 6,799,342 B1 | 10/2004 | Jarmon |
| 6,843,800 B1 | 1/2005 | Dobak, III |
| 6,878,156 B1 | 4/2005 | Noda |
| 6,887,263 B2 | 5/2005 | Bleam et al. |
| 6,890,347 B2 | 5/2005 | Machold et al. |
| 6,893,419 B2 | 5/2005 | Noda et al. |
| 6,918,924 B2 | 7/2005 | Lasheras et al. |
| 6,969,399 B2 | 11/2005 | Schock et al. |
| 7,070,612 B1 | 7/2006 | Collins et al. |

(56) References Cited

U.S. PATENT DOCUMENTS

| | | |
|---|---|---|
| 7,211,105 B2 | 5/2007 | Magers et al. |
| 7,258,662 B2 | 8/2007 | Machold et al. |
| 7,510,569 B2 | 3/2009 | Dae et al. |
| 7,666,215 B2 | 2/2010 | Ballister et al. |
| 7,806,915 B2 | 10/2010 | Scott et al. |
| 7,822,485 B2 | 10/2010 | Collins |
| 7,846,193 B2 | 12/2010 | Dae et al. |
| 7,857,781 B2 | 12/2010 | Noda et al. |
| 8,038,639 B2 | 10/2011 | Lo et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,366,667 B2 | 2/2013 | Chan et al. |
| 8,968,378 B2 | 3/2015 | Ginsburg et al. |
| 9,056,004 B2 | 6/2015 | Ginsburg et al. |
| 9,492,633 B2 | 11/2016 | Dabrowiak |
| 9,763,823 B2 | 9/2017 | Voorhees et al. |
| 9,784,263 B2 | 10/2017 | Hendricks et al. |
| 10,022,265 B2 | 7/2018 | Pamichev et al. |
| 2001/0031946 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0145525 A1 | 10/2002 | Friedman et al. |
| 2002/0183692 A1 | 12/2002 | Callister |
| 2002/0198579 A1 | 12/2002 | Khanna |
| 2003/0236496 A1 | 12/2003 | Samson et al. |
| 2004/0089058 A1 | 5/2004 | De Haan et al. |
| 2004/0102825 A1 | 5/2004 | Daoud |
| 2004/0171935 A1 | 9/2004 | Van Creveld et al. |
| 2004/0199230 A1 | 10/2004 | Yon |
| 2004/0210231 A1 | 10/2004 | Boucher et al. |
| 2004/0267340 A1 | 12/2004 | Cioanta et al. |
| 2005/0065584 A1 | 3/2005 | Schiff et al. |
| 2005/0156744 A1 | 7/2005 | Pires |
| 2005/0277890 A1* | 12/2005 | Stewart .................. G16H 20/17 604/189 |
| 2006/0064146 A1 | 3/2006 | Collins |
| 2006/0241335 A1 | 10/2006 | Benkowski et al. |
| 2006/0253095 A1 | 11/2006 | Stull |
| 2006/0293734 A1 | 12/2006 | Scott et al. |
| 2007/0007640 A1 | 1/2007 | Harnden et al. |
| 2007/0076401 A1 | 4/2007 | Carrez et al. |
| 2007/0093710 A1 | 4/2007 | Maschke |
| 2008/0267599 A1 | 10/2008 | Arnold et al. |
| 2009/0065565 A1 | 3/2009 | Cao |
| 2009/0099518 A1 | 4/2009 | Magers |
| 2010/0204765 A1 | 8/2010 | Hall et al. |
| 2011/0046551 A1 | 2/2011 | Augustine et al. |
| 2011/0184253 A1 | 7/2011 | Archer et al. |
| 2011/0196303 A1 | 8/2011 | Chan et al. |
| 2012/0095536 A1 | 4/2012 | Machold et al. |
| 2013/0079855 A1 | 3/2013 | Helkowski et al. |
| 2013/0079856 A1 | 3/2013 | Dabrowiak et al. |
| 2013/0090708 A1 | 4/2013 | Dabrowiak et al. |
| 2013/0178923 A1 | 7/2013 | Dabrowiak |
| 2014/0094880 A1 | 4/2014 | Lim et al. |
| 2014/0094882 A1 | 4/2014 | Lim |
| 2014/0094883 A1 | 4/2014 | Lim et al. |
| 2014/0276792 A1 | 9/2014 | Kaveckis et al. |
| 2014/0277302 A1 | 9/2014 | Weber et al. |
| 2015/0314055 A1 | 11/2015 | Hogard et al. |
| 2016/0228291 A1 | 8/2016 | Calliser et al. |
| 2016/0287434 A1* | 10/2016 | Dabrowiak ............... A61F 7/12 |
| 2016/0287435 A1 | 10/2016 | Pamichev et al. |
| 2018/0185192 A1 | 7/2018 | Mazzone et al. |
| 2018/0185193 A1 | 7/2018 | Mazzone et al. |
| 2018/0207024 A1 | 7/2018 | Dabrowiak et al. |

FOREIGN PATENT DOCUMENTS

| | | |
|---|---|---|
| DE | 102009050053 | 5/2011 |
| GB | 1183185 A | 3/1970 |
| GB | 2040169 A | 8/1980 |
| GB | 2212262 A | 7/1989 |
| GB | 2383828 A | 7/2003 |
| JP | 7308338 | 11/1995 |
| JP | 09-215754 A | 8/1997 |
| JP | 10-0127777 A | 5/1998 |
| JP | 10-305103 A | 11/1998 |
| JP | 2003028582 | 1/2003 |
| JP | 2003508150 A | 3/2003 |
| JP | 2004504110 | 2/2004 |
| JP | 2008154751 A | 7/2008 |
| JP | 2011505929 A | 3/2011 |
| JP | 2011182849 A | 9/2011 |
| JP | 2013519849 | 5/2013 |
| WO | 1990/001682 A1 | 2/1990 |
| WO | 1993/002730 A1 | 2/1993 |
| WO | 1993/004727 A1 | 3/1993 |
| WO | 1994/000177 A1 | 1/1994 |
| WO | 1994/001177 A1 | 1/1994 |
| WO | 1997/025011 A1 | 7/1997 |
| WO | 1998/024491 A1 | 6/1998 |
| WO | 1998/040017 A2 | 9/1998 |
| WO | 2000/010494 A1 | 3/2000 |
| WO | 2001/013809 A1 | 3/2001 |
| WO | 2001/064146 A1 | 9/2001 |
| WO | 2001/076517 A2 | 10/2001 |
| WO | 2001/083001 A1 | 11/2001 |
| WO | WO 2009/056640 A2 | 5/2009 |

OTHER PUBLICATIONS

Watts, Dorraine Day, et al., "Hypothermic Coagulopathy in Trauma: Effect of Varying Levels of Hypothermia on Enzyme Speed, Platelet Function, and Fibrinolytic Activity," Journal of Trauma—Injury Infection & Critical Care, vol. 44, No. 5, pp. 846-854, 1998.

F.W. Behmann, et al., "Die Regelung der Wärmebildung bei künstlicher Hypothermie," Pflügers Archiv, Bd. 266, S. 408-421 (1958).

F.W. Behmann, et al., "Intravasale Kühlung," Pflügers Archiv, Bd. 263, S. 145-165 (1956).

PCT International Search Report dated Jun. 25, 2018 in related PCT Application No. PCT/US2018/016752.

PCT International Search Report dated Jun. 25, 2018 in related PCT Application No. PCT/US2018/016754.

* cited by examiner

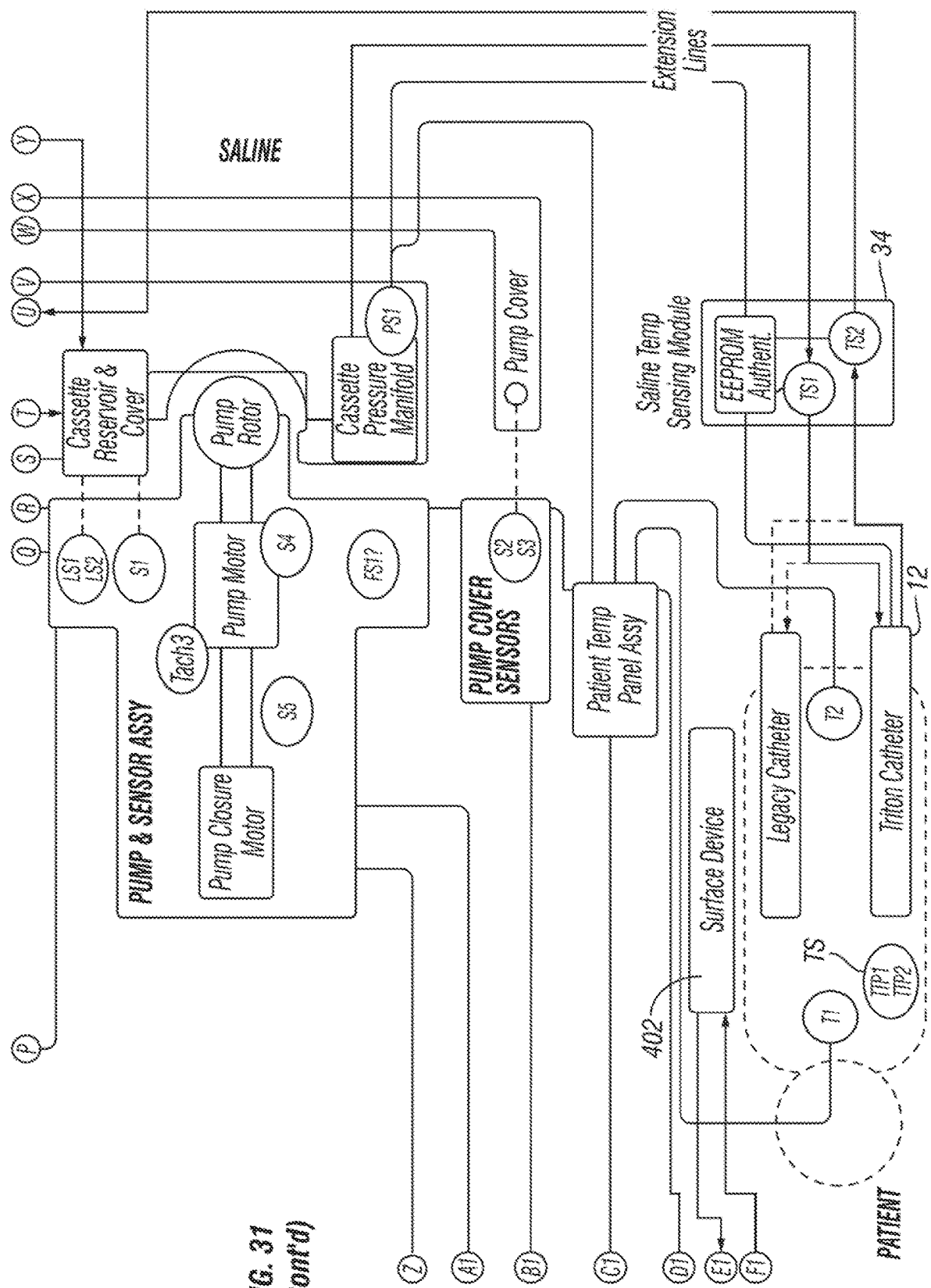
FIG. 31 (Con't'd)

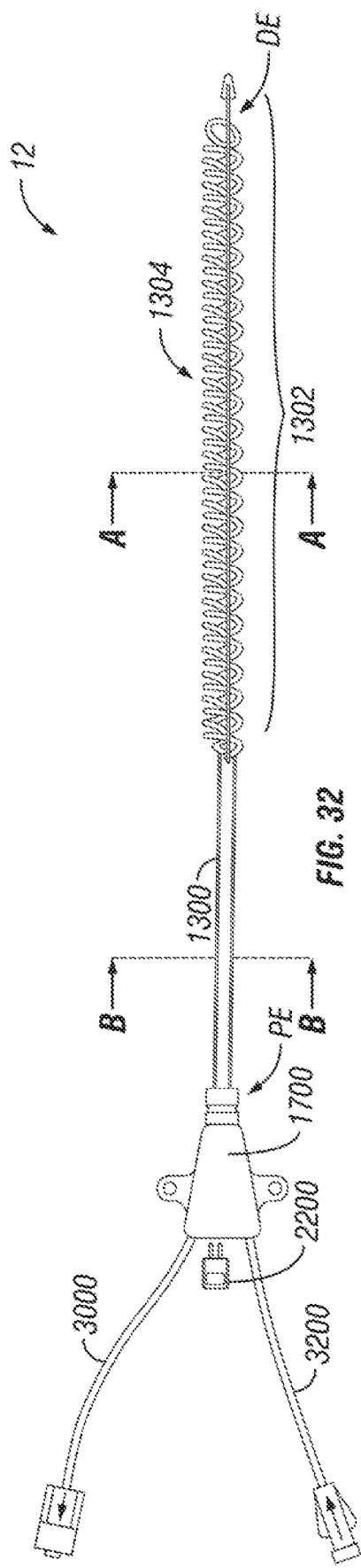
FIG. 32
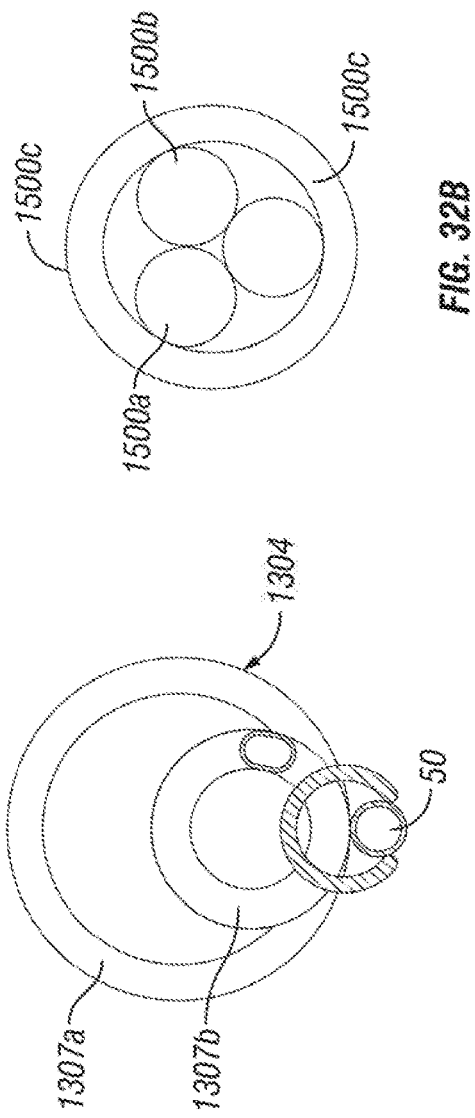
FIG. 32A
FIG. 32B

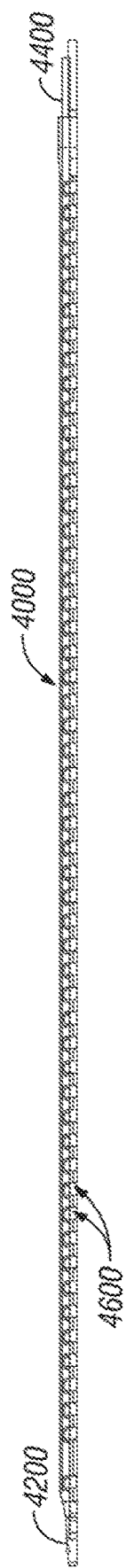
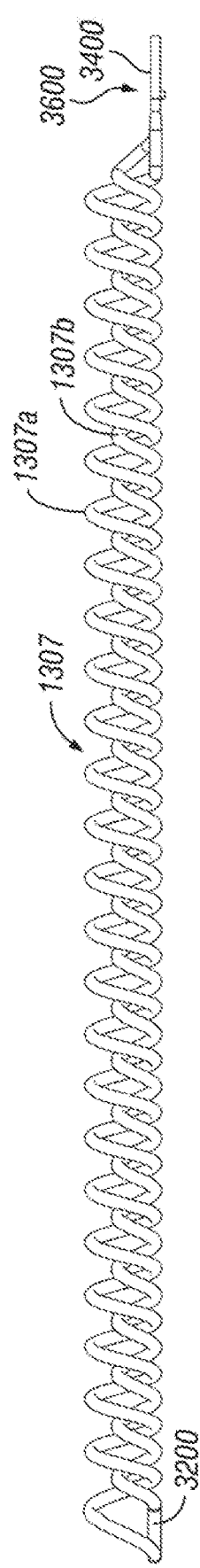
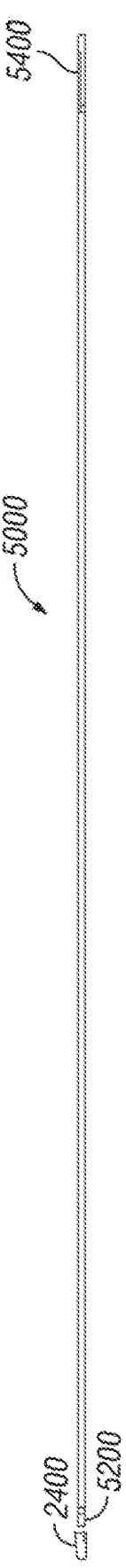
FIG. 33A
FIG. 33B
FIG. 33C

| Initiate Anti-shivering Medication Protocol | Turn on Endovascular Heat exchange System |
|---|---|

Begin Therapeutic Hypothermia with Intravenous Infusion of up to One Liter of 4 degree C Saline Solution Using Pressure Bag. Then Continue Using Endovascular Heat Exchange System

Documentation/Work Up:

| Document Time Endovascular Heat Exchange System Was Turned On | Document Time of Occurrence of STEMI, Arrival Time at E.D. and Other Subject Data Upon Arrival (e.g., Temperature, Physical Exam, Vital Signs, Blood Studies, Lab Studies, Cardiac Markers, Troponin T, 12-Lead ECG) | Maintain Sedation and Document All Medications |
|---|---|---|

Initiation of Cooling to 32 Degrees C.

| Begin cooling induction by forced infusion 2SmL/kg 4-C saline for up to 1 L at treating Physician's discretion | Insert heat exchange catheter and connect to cassette in heat exchange console. Enter 32 degree C target body temperature and cool at maximum power. Insert temperature probe. | Use Bair Hugger System for counter warming of body surface and follow hospital guidelines for venous thromboembolism prophylaxis |
|---|---|---|

*FIG. 37*

If BSAS≥2.2 at 32.0 C increase dose of Pethidine as indicated in Antishivering Guidelines (Attachment II) and increase set-point temperature to 32.5·C

*Immediately Prior to Reperfusion:*

| Perform Angiogram after Induction of Hypothermia and just prior to PCI | Document Core Body Temp. at time of PCI & Continue Cooling until subject has reached 32.0±1.0·C |

*Maintenance of Hypothermia at Target Temperature of 32.0+/-1.0 degrees C:*

| Maintain Target Temperature of 32.0+/-1.0 degrees C for 3.0 Hours +/- 15 Minutes | Assess Need for Antishivering Medication |

*Rewarming:*

| Increase Target Temperature to 36.0 degrees C and rewarm at a rate of 1.0 degree C per hour until subject's body temp is 36.0 degrees C | Assess Need for Antishivering Medication |

*Catheter Removal:*

Remove heat exchange catheter and temperature probe. Dispose per guidelines

FIG. 37
(Cont'd)

DEVICES, SYSTEMS AND METHODS FOR ENDOVASCULAR TEMPERATURE CONTROL

RELATED APPLICATIONS

This is a continuation in part of U.S. patent application Ser. No. 15/594,541 entitled Devices, Systems and Methods for Endovascular Temperature Control filed May 12, 2017, now U.S. Pat. No. 11,116,657, which is a continuation in part of U.S. patent application Ser. No. 15/423,581 entitled Devices, Systems and Methods or Endovascular Temperature Control filed Feb. 2, 2017, now U.S. Pat. No. 11,185,440. Additionally, this application is a continuation in part of PCT International Patent Application No. PCT/US18/16754 entitled Devices, Systems and Methods for Endovascular Temperature Control filed Feb. 2, 2018. The entire disclosure of each such prior application is hereby expressly incorporated herein by reference.

FIELD OF THE INVENTION

The present disclosure relates generally to the fields of medicine and engineering and more particularly to devices, systems and methods for controlling a patient's body temperature by endovascular heat exchange.

BACKGROUND

Pursuant to 37 CFR 1.71(e), this patent document contains material which is subject to copyright protection and the owner of this patent document reserves all copyright rights whatsoever.

In various clinical situations, it is desirable to warm, cool or otherwise control the body temperature of a subject. For example, hypothermia can be induced in humans and some animals for the purpose of protecting various organs and tissues (e.g., heart, brain, kidneys) against the effects of ischemic, anoxic or toxic insult. For example, animal studies and/or clinical trials suggest that mild hypothermia can have neuroprotective and/or cardioprotective effects in animals or humans who suffer from ischemic cardiac events (e.g., myocardial infract, acute coronary syndromes, etc.), post-anoxic coma after cardiopulmonary resuscitation, traumatic brain injury, stroke, subarachnoid hemorrhage, fever and neurological injury. Also, studies have shown that whole body hypothermia can ameliorate the toxic effects of radiographic contrast media on the kidneys (e.g., radiocontrast nephropathy) of patients with pre-existing renal impairment who undergo angiography procedures.

One method for inducing hypothermia is by endovascular temperature management (ETM) wherein a heat exchange catheter is inserted into a blood vessel and a thermal exchange fluid is circulated through a heat exchanger positioned on the portion of the catheter that is inserted in the blood vessel. As the thermal exchange fluid circulates through the catheter's heat exchanger, it exchanges heat with blood flowing past the heat exchange in the blood vessel. Such technique can be used to cool the subject's flowing blood thereby resulting in a lowering of the subject's core body temperature to some desired target temperature. ETM is also capable of warming the body and/or of controlling body temperature to maintain a monitored body temperature at some selected temperature. If a controlled rate of re-warming or re-cooling from the selected target temperature is desired, that too can be accomplished by carefully controlling the amount of heat added or removed from the body and thereby controlling the temperature change of the patient.

SUMMARY

In accordance with the present disclosure, there are provided heat exchange devices, systems and methods which facilitate efficient endovascular and/or body surface heat exchange.

In accordance with one embodiment, there is provided a system for circulating a warmed or cooled thermal exchange fluid through an endovascular heat exchanger (e.g., an endovascular heat exchange catheter), wherein a) the system produces a pulsatile flow of thermal exchange fluid and b) the system is connected to the endovascular heat exchanger by way of one or more conduits which comprise a pulse damping conduit that functions not only as a conduit through which the thermal exchange fluid flows but also a pulse damper for damping pulses or pressure in the thermal exchange fluid as it flows therethrough. The pulse damping conduit may comprise, for example, tubing that has sufficient elastic or flexural properties to dampen or reduce the amplitude of pulses in the thermal exchange fluid as it flows therethrough.

In accordance with another embodiment, there is provided a system for warming or cooling the body of a human or animal subject, such system comprising an extracorporeal control system that is connectable to one or more changeable component(s) (e.g., an endovascular heat exchange catheter, a body surface heat exchange pad, tubing, a cassette through which thermal exchange fluid circulates, other disposable components, etc.). When the changeable component(s) is/are connected to the extracorporeal control system, the system is useable to effect heat exchange with the subject's body. The changeable component(s) may include machine readable encoded information. The extracorporeal control system includes a reader or processor that receives and reads the encoded information. The extracorporeal control system uses such encoded information to identify, qualify, confirm or control the operation of the changeable component(s). The encoded information may be stored in any suitable electronic storage medium and may be embedded in a chip or microchip mounted on or in the changeable component(s). Examples of the types of encoded information that may be stored include but are not limited to; unique identifier(s) for the changeable components (e.g., manufacturer identification, part number, lot number, etc.), indications of whether the changeable component(s) have previously been used (e.g., an encoded indication of first use), indications of whether the changeable component(s) is/are expired (e.g., encoded expiration date), operational characteristic(s) and or operational variables (e.g., minimum and/or maximum pressure, minimum and or maximum flow rate, control algorithm to be used, etc.) of the changeable component(s) (e.g., encoded indications of the size, type, volume, etc. of the changeable component(s). Examples of the types of information storage that may be utilized include but are not necessarily limited to: non-volatile random access memory (RAM), non-volatile flash memory, electrically erasable programmable read-only memory (EEPROM) or ferroelectric random access memory (FRAM). The extracorporeal control system may comprises a controller (e.g., a processor) programmed to take one or more actions in response to the encoded information. For example, the controller may be programmed to determine whether the encoded information meets a prerequisite requirement and to proceed with warming or cooling of the subject's body only if said prerequisite requirement is met.

In accordance with another embodiment, there is provided a thermal exchange engine for warming or cooling a thermal exchange fluid. Such thermal exchange engine comprises thermal exchange plates or evaporators which are alternately coolable by circulation of refrigerant through the plates and warmable by heaters positioned on or in the plates. A cassette receiving space is located between the temperature controlled plates and is configured for receiving a cassette or heat exchanger. The cassette comprises a frame and an expandable vessel (e.g., a bag or other expandable fluid containing vessel). The expandable vessel is finable with thermal exchange fluid, e.g., after the cassette has been inserted into the cassette receiving space. Heat is thereby transferred between the refrigerant and the thermal exchange fluid or the heater(s) and the thermal exchange fluid. In some embodiments, outer surface(s) of the expandable vessel may be coated with a release material, covered with a layer of releasable material or otherwise treated or modified to deter sticking of the expandable vessel to the adjacent thermal exchange plates. In some embodiments, surface(s) of the thermal exchange plates and/or surfaces of the expandable vessel or a layer on a surface of the expandable vessel may be textured or provided with holes, groves or other surface features to deter sticking of the expandable vessel to the adjacent thermal exchange plates. In some embodiments, the cassette may comprise a housing attached to an insertable portion (e.g., the frame and expandable vessel) by a hinged attachment such that the cassette may be disposed in a folded or closed configuration prior to use and converted to an unfolded or open configuration at the time of use. Such hinged connection between the housing and the insertable portion may be constructed so that, once unfolded or opened, the cassette locks in the unfolded or open configuration. In some embodiments, a plurality of hooks located in the console or system may be initially positioned in retracted positions allowing insertion of the insertable portion into the cassette receiving space between the thermal exchange plates and, thereafter, may be moved to advanced positions wherein they hold the insertable portion of the cassette within the cassette receiving space.

In accordance with another embodiment, there is provided a system configured to circulate warmed or cooled thermal exchange fluid through a body heat exchanger to warm or cool the body or a human or animal subject, wherein the system comprises a first display device which receives signals from one or more temperature sensors and displays temperature data based on signals received from said one or more temperature sensors. The first display device is connectable, by wired or wireless connectivity, to a second display device (e.g., a bedside monitor, central unit monitor, remote monitor, etc.), so as to transmit said signals received from said one or more temperature sensors from the first display device to the second display device. The system further comprises circuitry for minimizing or eliminating any effect of ambient temperature on such signals as they are transmitted from the first display device to the second display device. In some embodiments, the signals transmitted from the first display device to the second display device may comprise signals representative of sensed temperatures, such as patient body temperature, temperature of thermal exchange fluid flowing to the body heat exchanger, temperature of thermal exchange fluid flowing from the body heat exchanger, etc.

Disclosed herein is a system comprising: a heat exchange catheter which comprises (i) a catheter body having a distal end, (ii) a elongate member attached to the catheter body and extending beyond its distal end, and (iii) at least one helically coiled tube disposed on the elongate member and connected to delivery and return lumen in the catheter body; and fluid cooling apparatus comprising a refrigeration apparatus, cooling plates, and a cassette connected to the delivery and return lumens of the catheter body and operative to circulate a cooled thermal exchange fluid through the cassette, into the catheter, through said at least one helically coiled tube, out of the catheter and back into the cassette, wherein the heat exchange catheter and fluid cooling apparatus and said at least one helically coiled tube are sized, configured and constructed to render the system capable of delivering at least about 600 watts of cooling power. The fluid cooling apparatus may be configured to deliver to the heat exchange catheter a flow of heat exchange fluid that is cooled to a temperature at or below 4° C. at a rate of at least 600 mL/min at steady state, when up to 700 W of heat is being added to the flowing saline as a result of heat exchange through the catheter's heat exchanger. The fluid cooling apparatus may be configured to deliver to the heat exchange catheter a flow of heat exchange fluid that is cooled to a temperature at or below 4° C. at a rate of from 200 mL/min to 240 mL/min at steady state, when up to 70 W of heat is being added to the flowing saline as a result of heat exchange through the catheter's heat exchanger. The fluid cooling apparatus may be configured to deliver to the heat exchange catheter a flow of heat exchange fluid that is warmed to a temperature at or above 42° C. at a rate of at least 400 mL/min at steady state, when up to 200 W of heat is being removed from the flowing saline as a result of heat exchange through the catheter's heat exchanger. The system may be configured to deliver greater than or equal to 600 W of cooling power by circulating heat exchange fluid that is cooled to a temperature at or below 4° C. through the heat exchange catheter at a catheter pressure of about 60 PSI. The system may further comprise heating apparatus useable for warming rather than cooling the heat exchange fluid. Such heating apparatus may deliver greater than or equal to 50 W of warming power by circulating heat exchange fluid that is warmed to a temperature above 37° C. through the heat exchange catheter at a catheter pressure of about 40 PSI.

In another aspect, disclosed herein is a system comprising: at least one set of thermal exchange plates which warm or cool a heat exchange fluid for delivery to a body surface or endovascular heat exchanger; a refrigeration unit for circulating cold refrigerant through said at least one thermal exchange plate; at least one heater for heating the thermal exchange plate; a programmable controller; wherein the system further comprises a bypass circuit for alternately circulating hot refrigerant from the refrigeration unit through said at least one thermal exchange plate; and wherein the controller is programmed to monitor the power output of said at least one heater and, if said power output exceeds a limit, to cause hot refrigerant to flow through the bypass circuit and through said at least one thermal exchange plate, thereby assisting said at least one heater in warming said at least one thermal exchange plate. The controller may be further programmed to incrementally or progressively reduce the amount of hot refrigerant being circulated through said at least one thermal exchange plate in the event that the power output of said at least one heater falls below the limit until a target temperature has been reached.

In another aspect, disclosed herein is a body heat exchange system comprising: heater/cooler apparatus for alternately warming or cooling a heat exchange fluid for delivery to a body heat exchange device for surface or endovascular heat exchange in or on the body of a subject; a pump for circulating the heat exchange fluid through the body heat exchange device; a controller which is programmed to selectively vary both the temperature and flow rate of the heat exchange fluid to maintain the subject's body temperature at or within a permissible range of a target body temperature. The controller may be programmed such that, after a body temperature of the subject has been warmed or cooled to a target temperature, the controller will cause the system to maintain said body temperature at or within a permissible variance range of the target temperature by: holding the temperature of the heat exchange fluid constant and varying the operation of the pump to adjust the flow rate of heat exchange fluid through the catheter as needed to maintain said body temperature at or within a permissible variance range of the target temperature so long as the speed of the pump does not exceed a maximum pump speed; and if the pump exceeds the predetermined maximum pump speed, adjusting the temperature of the heat exchange fluid such that said body temperature at or within a permissible variance range of the target temperature without exceeding the maximum pump speed. If it is necessary to switch between cooling mode and warming mode in order to maintain said body temperature at or within a permissible variance range of the target temperature, the controller may, upon making such switch, adjust the temperature of the heat exchange fluid irrespective of whether the maximum pump speed has been exceeded. The system may be combined with a body heat exchange device. The body heat exchange device may comprise an endovascular heat exchange catheter. The body heat exchange device comprises a body surface heat exchange member.

In another aspect, disclosed herein is a body heat exchange system comprising: heater/cooler apparatus for alternately warming or cooling a heat exchange fluid for delivery to a body heat exchange device for surface or endovascular heat exchange in or on the body of a subject; a pump for circulating the heat exchange fluid through the body heat exchange device; a temperature sensor for sensing the temperature of the heat exchange fluid; a pressure sensor for sensing the pressure of the heat exchange fluid and a controller which receives a maximum pump speed set point and signals from the temperature sensor and pressure sensor, said controller being programmed to: a) establish current cold/warm status of the heat exchange fluid based on the sensed temperature of the heat exchange fluid; b) determining whether operation of the pump at the maximum pump speed set point will cause over-pressurization of the heat exchange fluid or under-pressurization of the heat exchange fluid; and c) if it is determined that operation of the pump at the maximum pump speed set point will cause over-pressurization of the heat exchange fluid, causing the maximum pump speed set point to change to an adjusted maximum pump speed set point at which the pump may operate without causing over-pressurization of the heat exchange fluid; or d) if it is determined that operation of the pump at the maximum pump speed set point will cause an under-pressurization of the heat exchange fluid, causing the maximum pump speed set point to change to an adjusted maximum pump speed set point at which the pump may operate without causing under-pressurization of the heat exchange fluid. The controller may be programmed to perform steps a through c repeatedly. The controller may be programmed to repeat Steps a through c at least once every 3 seconds. The controller may be programmed to repeat Steps a through c every three seconds. The controller may be programmed to cause the maximum pump speed set point to change by applying a maximum pump speed set point adjustment integrator. The application of the maximum pump speed adjustment integrator may cause the maximum pump speed set point to change slowly. The controller may be programmed to determine that operation of the pump at the maximum pump speed set point will cause over-pressurization of the heat exchange fluid based on different maximum pressure limits for cold status and warm status. The maximum pressure limit when operating with cold status heat exchange fluid may, for example, be 40 psi and the maximum pressure limit when operating with warm status heat exchange fluid may, for example, be 60 psi. The controller may be programmed to establish warm status in Step a if the sensed temperature of the heat exchange fluid is above 19.5 degree C. and to establish cold status in Step a if the sensed temperature of the heat exchange fluid is not above 19.5 degrees C. The controller may be further programmed to store the most recent prior maximum pump speed set point for warm status and cold status. The controller may be further programmed such that, if performance of Step a results in a change from warm status to cold status, the controller will reset the maximum pump speed set point to the most recent stored maximum pump speed set point for cold status heat exchange fluid. The controller may be further programmed such that, if performance of Step a results in a change from cold status to warm status, the controller will reset the maximum pump speed set point to the most recent stored maximum pump speed set point for warm status heat.

In another aspect, disclosed herein is a method for deterring reperfusion injury in a human or animal subject who is suffering from ischemia and who undergoes reperfusion to relieve the ischemia, said method comprising the steps of: cooling a body temperature of the subject to a target temperature of 35 degrees C. or below; and performing the reperfusion after the body temperature of the subject has been cooled to the target temperature; and maintaining the target temperature for a period of time after reperfusion. The target temperature may be between 32 degrees C. and 34 degrees C. The step of cooling a body temperature of the subject to a target temperature of 35 degrees C. or below may be performed in less than 30 minutes. The target temperature may be maintained for a period of 1-5 hours after reperfusion. The step of cooling a body temperature of the subject to a target temperature of 35 degrees C. or below in less than 30 minutes may comprise: inserting a heat exchange catheter into the subject's vasculature; circulating heat exchange fluid through the heat exchange catheter at a temperature and flow rate sufficient to cold said body temperature to said target temperature in less than 30 minutes. The heat exchange catheter may comprise (i) a catheter body having a distal end, (ii) a elongate member attached to the catheter body and extending beyond its distal end, and (iii) at least one helically coiled tube disposed on the elongate member and connected to delivery and return lumen in the catheter body; and the heat exchange fluid may be circulated through the delivery lumen, at least one helically coiled tube and return lumen of the catheter by a cooling apparatus that comprises a refrigeration apparatus, cooling plates, and a cassette which is connected to the delivery and return lumens of the catheter body and may be operative to circulate the cooled heat exchange fluid through the cassette, into the catheter, through the delivery lumen, through said at least one helically coiled tube, out of the return lumen and back into the cassette; wherein the heat exchange catheter and fluid cooling apparatus and said at least one helically coiled tube are sized, configured and constructed to render the system capable of delivering at least about 600 watts of cooling power. The fluid cooling apparatus may be configured to deliver to the heat exchange catheter a flow of heat exchange fluid that is cooled to a temperature at or below 4° C. at a rate of at least 600 mL/min at steady state, when up to 700 W of heat is being added to the flowing saline as a result of heat exchange through the catheter's heat exchanger. The fluid cooling apparatus may be configured to deliver to the heat exchange catheter a flow of heat exchange fluid that is cooled to a temperature at or below 4° C. at a rate of from 200 mL/min to 240 mL/min at steady state, when up to 70 W of heat is being added to the flowing saline as a result of heat exchange through the catheter's heat exchanger. The fluid cooling apparatus may be configured to deliver to the heat exchange catheter a flow of heat exchange fluid that is warmed to a temperature at or above 42° C. at a rate of at least 400 mL/min at steady state, when up to 200 W of heat of heat is being removed from the flowing saline as a result of heat exchange through the catheter's heat exchanger. The fluid cooling apparatus may be configured to deliver to greater than or equal to 600 W of cooling power by circulating heat exchange fluid that is cooled to a temperature at or below 4° C. through the heat exchange catheter at a catheter pressure of about 60 PSI.

In another aspect, disclosed herein is a system comprising: a heat exchange catheter which comprises (i) a catheter body having a distal end, (ii) a elongate member attached to the catheter body and extending beyond its distal end, and (iii) at least one helically coiled tube disposed on the elongate member and connected to delivery and return lumen in the catheter body; and fluid cooling apparatus comprising a refrigeration apparatus, thermal exchange plates through which refrigerant circulates having a cassette receiving space between the thermal exchange plates, a cassette connected to the delivery and return lumens of the catheter body and operative to circulate a cooled thermal exchange fluid through the cassette, into the catheter, through said at least one helically coiled tube, out of the catheter and back into the cassette; wherein the heat exchange catheter and fluid cooling apparatus are configured to render the system capable of delivering at least about 600 watts of cooling power.

In another aspect, the fluid cooling apparatus are configured to deliver to the heat exchange catheter a flow of heat exchange fluid that is cooled to a temperature at or below 4° C. at a rate of at least 600 mL/min at steady state, when up to 700 W of heat is being added to the flowing saline as a result of heat exchange through the catheter's heat exchanger. The fluid cooling apparatus may be configured to deliver to the heat exchange catheter a flow of heat exchange fluid that is cooled to a temperature at or below 4'C at a rate of from 200 mL/min to 240 mL/min at steady state, when up to 70 W of heat is being added to the flowing saline as a result of heat exchange through the catheter's heat exchanger. The fluid cooling apparatus may be configured to deliver to the heat exchange catheter a flow of heat exchange fluid that is warmed to a temperature at or above 42° C. at a rate of at least 400 mL/min at steady state, when up to 200 W of heat is being removed from the flowing saline as a result of heat exchange through the catheter's heat exchanger. The fluid cooling apparatus are configured to deliver greater than or equal to 600 W of cooling power by circulating heat exchange fluid that is cooled to a temperature at or below 4° C. through the heat exchange catheter at a catheter pressure of about 60 PSI. The system may further comprise apparatus useable for warming rather than cooling the heat exchange fluid. The system may be configured to deliver greater than or equal to 50 W of warming power by circulating heat exchange fluid that is warmed to a temperature above 37° C. through the heat exchange catheter at a catheter pressure of about 40 PSI. The system may further comprise at least one heater for warming the thermal exchange plates and a controller programmed to monitor the power output of said at least one heater and, if said power output exceeds a limit, to cause hot refrigerant to flow through the bypass circuit and through said at least one thermal exchange plate, thereby assisting said at least one heater in warming said at least one thermal exchange plate. The controller may be further programmed to incrementally or progressively reduce the amount of hot refrigerant being circulated through said at least one thermal exchange plate in the event that the power output of said at least one heater falls below the limit until a target temperature has been reached. The system may further comprise at least one heater for warming the thermal exchange plates, a pump for pumping the heat exchange fluid at varied flow rates, and a controller programmed to selectively vary both the temperature and flow rate of the heat exchange fluid to maintain the subject's body temperature at or within a permissible range of a target body temperature. The controller may be programmed such that, after a body temperature of the subject has been warmed or cooled to a target temperature, the controller will cause the system to maintain said body temperature at or within a permissible variance range of the target temperature by: holding the temperature of the heat exchange fluid constant and varying the operation of the pump to adjust the flow rate of heat exchange fluid through the catheter as needed to maintain said body temperature at or within a permissible variance range of the target temperature so long as the speed of the pump does not exceed a maximum pump speed; and if the pump exceeds the predetermined maximum pump speed, adjusting the temperature of the heat exchange fluid such that said body temperature at or within a permissible variance range of the target temperature without exceeding the maximum pump speed. If it is necessary to switch between cooling mode and warming mode in order to maintain said body temperature at or within a permissible variance range of the target temperature, the controller may, upon making such switch, adjust the temperature of the heat exchange fluid irrespective of whether the maximum pump speed has been exceeded. The system may further comprise at least one heater for warming the thermal exchange plates, a pump for pumping the heat exchange fluid at varied flow rates, a temperature sensor for sensing the temperature of the heat exchange fluid, a pressure sensor for sensing the pressure of the heat exchange fluid, and a controller which receives a maximum pump speed set point and signals from the temperature sensor and pressure sensor, said controller being programmed to: a) establish current cold/warm status of the heat exchange fluid based on the sensed temperature of the heat exchange fluid; b) determine whether operation of the pump at the maximum pump speed set point will cause over-pressurization of the heat exchange fluid or under-pressurization of the heat exchange fluid; and c) if it is determined that operation of the pump at the maximum pump speed set point will cause over-pressurization of the heat exchange fluid, causing the maximum pump speed set point to change to an adjusted maximum pump speed set point at which the pump may operate without causing over-pressurization of the heat exchange fluid; or d) if it is determined that operation of the pump at the maximum pump speed set point will cause an under-pressurization of the heat exchange fluid, causing the maximum pump speed set point to change to an adjusted maximum pump speed set point at which the pump may operate without causing under-pressurization of the heat exchange fluid. The controller may be programmed to perform steps a through c repeatedly. The controller may be programmed to repeat Steps a through c at least once every 3 seconds. The controller may be programmed to repeat Steps a through c every three seconds. The controller may be programmed to cause the maximum pump speed set point to change bay applying a maximum pump speed set point adjustment integrator. The application of the maximum pump speed adjustment integrator may cause the maximum pump speed set point to change slowly. The controller may be programmed to determine that operation of the pump at the maximum pump speed set point will cause over-pressurization of the heat exchange fluid based on different maximum pressure limits for cold status and warm status. The maximum pressure limit when operating with cold status heat exchange fluid may be, for example, 40 psi and the maximum pressure limit when operating with warm status heat exchange fluid may be, for example, 60 psi. The controller may be programmed to establish warm status in Step a if the sensed temperature of the heat exchange fluid is above 19.5 degree C. and to establish cold status in Step a if the sensed temperature of the heat exchange fluid is not above 19.5 degrees C. The controller may be further programmed to store the most recent prior maximum pump speed set point for warm status and cold status. The controller may be further programmed such that, if performance of Step a results in a change from warm status to cold status, the controller will reset the maximum pump speed set point to the most recent stored maximum pump speed set point for cold status heat exchange fluid. The controller may be further programmed such that, if performance of Step a results in a change from cold status to warm status, the controller will reset the maximum pump speed set point to the most recent stored maximum pump speed set point for warm status heat. The system may be configured to deliver greater than or equal to 700 W of cooling power.

In another aspect, disclosed herein is a system usable for circulating warmed or cooled thermal exchange fluid through a plurality of different changeable heat exchange components which are available and alternately connectable to the system, said system comprising: thermal exchange fluid warming/cooling apparatus for warming, cooling or alternately warming and cooling the thermal exchange fluid; a pump for pumping the thermal exchange fluid; a controller; and apparatus for communicating, to the controller, identifying data which is associated with a selected one of said plurality of changeable heat exchange components; wherein the controller is programmed to assign, on the basis of the identifying data, operational variables for use in connection with the selected one of said plurality of different changeable heat exchange components and to thereafter control the operation of at least one of said thermal exchange fluid warming/cooling apparatus and said pump in accordance with the assigned operational variables. The thermal exchange fluid warming/cooling apparatus may comprise an extracorporeal heat exchange system through which the thermal exchange circulates. The apparatus for communicating to the controller may comprise apparatus for communicating to the controller machine readable identifying data that is encoded on or in the selected one of said plurality of different changeable heat exchange components. The plurality of different changeable heat exchange components may be selected from: endovascular heat exchange catheters, body surface heat exchangers, tubings or tubing sets and cassettes through which the thermal exchange fluid circulates. The plurality of different changeable heat exchange components may comprise a plurality of different types of heat exchange catheters or a plurality of different cassettes each of which is used in connection with a different type of heat exchange catheter and the operational variables may comprise at least one of: minimum fluid pressure, maximum fluid pressure, minimum fluid flow rate, maximum fluid flow rate, number of temperature sensors, location(s) of temperature sensor(s), maximum temperature, minimum temperature and control algorithm to be used.

In another aspect, disclosed herein is a system for warming or cooling the body of a human or animal subject, such system comprising: an extracorporeal control console having a warming and/or cooling apparatus, a pump and a controller and a cassette having a fluid flow path that is connectable to a body heat exchanger positionable on or in a subject's body, such cassette being positionable at an operating position on or in the extracorporeal unit while connected to a body heat exchanger, such that a) the pump will circulate heat exchange fluid through the cassette's heat exchange fluid flow path, through the connected body heat exchanger and back into the cassette's heat exchange fluid flow path and b) the warming and/or cooling apparatus will warm and/or cool the circulating heat exchange fluid. Such cassette may further comprise an electronic storage medium containing machine readable encoded information. The extracorporeal control console may further comprise a reader which receives and reads the cassette's encoded information and the controller may use the cassette's encoded information, as read by the reader, to control operation of one or more components of the system. In some embodiments, the cassette is useable or approved for use with only a single body heat exchanger type and the encoded information either includes, or causes the controller to select and use, a control algorithm, operational setting or parameter that is suitable for that single body heat exchanger type. In some embodiments the cassette may be useable or approved for use with a plurality of different body heat exchanger types and the encoded information includes, or causes the controller to select and use, a control algorithm, operational setting or parameter that is suitable for any of the body heat exchanger types useable or approved for use with the cassette. In some embodiments the extracorporeal control console may be alternately useable with a first cassette that is useable or approved for use with only a single body heat exchanger type and has encoded information that either includes, or causes the controller to select and use, a control algorithm, operational setting or parameter that is suitable for that single body heat exchanger or a second cassette having a fluid flow path that is connectable to a body heat exchanger, such second cassette being alternately positionable, instead of said cassette, in said operating position such that a) the pump will circulate heat exchange fluid through the second cassette's heat exchange fluid flow path, through the connected body heat exchanger and back into the second cassette's heat exchange fluid flow path and b) the warming and/or cooling apparatus will warm and/or cool the circulating heat exchange fluid; the second cassette further comprising an electronic storage medium containing machine readable encoded information; wherein the reader receives and reads the second cassette's encoded information; and wherein the controller uses the second cassette's encoded information, as read by the reader, to control operation of one or more components of the system. Such second cassette may be useable or approved for use with a plurality of different body heat exchanger types and the encoded information includes, or causes the controller to select and use, a control algorithm, operational setting or parameter that is suitable for any of the body heat exchanger types useable or approved for use with the second cassette. Such plurality of approved body heat exchangers may have a recommended pressure limit and the second cassette's encoded information may include, or cause the controller to select and use, a control algorithm, operational setting or parameter that limits the speed of the pump such that heat exchange fluid pressure within the body heat exchanger connected to the second cassette will not exceed a maximum pressure limit for that body heat exchanger, irrespective of which of the plurality of body heat exchanger types is connected to the second cassette. In some embodiments, the second cassette's encoded information may distinguish the second cassette from the cassette and wherein the controller is pre-programmed to select and use, in the basis of that encoded information, a control algorithm, operational setting or parameters suitable for the body heat exchanger(s) that are useable or approved for use of either the cassette or the second cassette, depending on which is presently inserted in the operating position. The electronic storage medium may comprise a medium type selected from: non-volatile random access memory (RAM); non-volatile flash memory; electrically erasable programmable read-only memory (EEPROM); ferroelectric random access memory (FRAM); a chip-embedded storage medium and a microchip-embedded storage medium. The cassette's encoded information may include an indication that the cassette meets a prerequisite requirement and the extracorporeal unit will proceed with warming or cooling of the heat exchange fluid only if the reader has determined that the encoded information includes said indication that the cassette meets a prerequisite requirement. An indication that the cassette meets a prerequisite requirement may comprise at least one of: an expiration date and the absence of an indication that the cassette has been previously used. The body heat exchanger(s) may comprise heat exchange catheters or body surface heat exchangers.

In another aspect, disclosed herein is a body temperature management system comprising: a body heat exchanger positionable on or in a subject's body, a heat exchange fluid warmer and/or cooler; a heat exchange fluid pump which circulates heat exchange fluid through the heat exchange fluid warmer and/or cooler and through the body heat exchanger; a sensor for sensing the subject's actual body temperature; a user interface configured to receive a user-input patient temperature set point; and a controller which receives signals indicating the user-input patient temperature and the currently-sensed actual body temperature; wherein the controller is programmed to control the heat exchange fluid warmer or cooler and/or the heat exchange fluid pump to initially cause the system to perform a first phase of warming or cooling, during which the heat exchange fluid circulates through the body heat exchanger at temperature and flow rate to cause the sensed actual body temperature to increase or decrease until the sensed actual body temperature reaches a predetermined interim temperature, said interim body temperature being less than the user-input patient temperature set point if the subject is being warmed or greater than the patient temperature set point if the subject is being cooled; and, thereafter, cause the system to perform a second phase of warming or cooling to increase or decrease from the interim temperature to the user input temperature set point at one or more rates which are slower than said initial rate, until the sensed actual body temperature becomes equal to the user-input patient temperature set point without substantially overshooting the user input patient temperature set point; and, thereafter, cause the system to perform a third phase of warming or cooling during which the temperature and/or flow rate of the heat exchange fluid is/are periodically adjusted as needed to maintain the sensed actual body temperature substantially equal to the user-input patient temperature set point. The user interface may allow a user to select a rate of warming or cooling and the controller will cause the system to perform said first, second and third phases only when the selected rate of warming or cooling is greater than a triggering rate. Such triggering rate may be greater than 0.1 degrees C. per hour. The user interface may allow the user to select a maximum rate of warming or cooling and the controller will cause the system to perform said first, second and third phases when the maximum rate is selected. During the first phase, the temperature and/or flow rate of the heat exchange fluid or pump speed may be periodically adjusted as needed to cause the sensed actual body temperature to increase or decrease until the sensed actual body temperature reaches a predetermined interim temperature. During the second phase the temperature and/or flow rate of the heat exchange fluid or pump speed may be periodically adjusted as needed to cause the sensed actual body temperature to increase or decrease to the user input temperature set point. During the first phase the temperature and flow rate of the heat exchange fluid may be substantially constant and not varied based on sensed changes in the actual patient temperature. During the second phase, the actual patient body temperature may warm or cool at a rate of 0.05 degrees C. per hour to 0.1 degrees C. per hour. The user interface may allow the user to select a patient temperature set point and the controller will cause the system to perform said first, second and third phases only when the patient temperature set point is greater than a triggering patient temperature set point. Such triggering patient temperature set point may be greater than 37.8 degrees C.

Still further aspects and details of the present invention will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments of the invention, and shall not limit the scope of the invention in any way.

Figure 6:
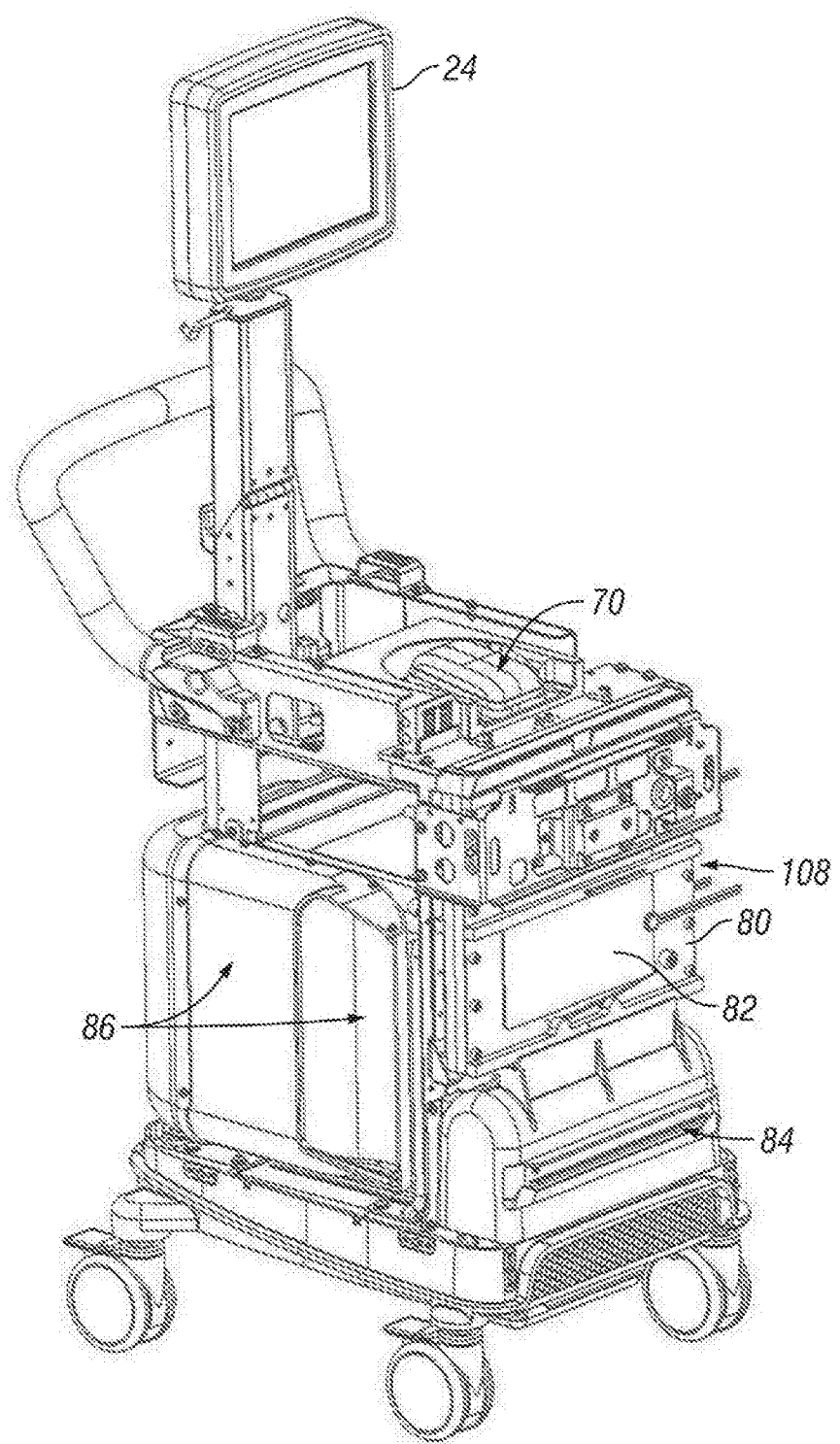

FIG. 6 is a right/front perspective view of the control console with its housing and access cover removed.

Figure 7:
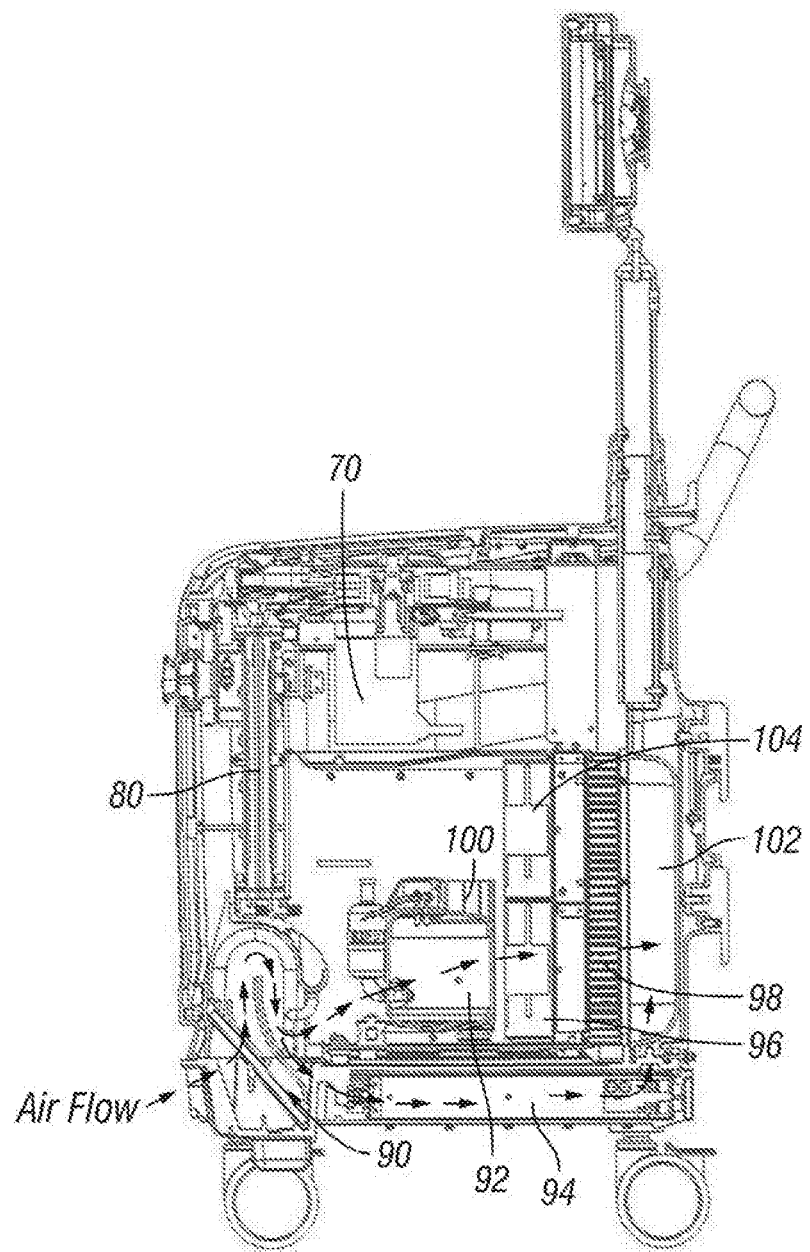

FIG. 7 is a left cross-sectional view of the control console.

Figure 8:
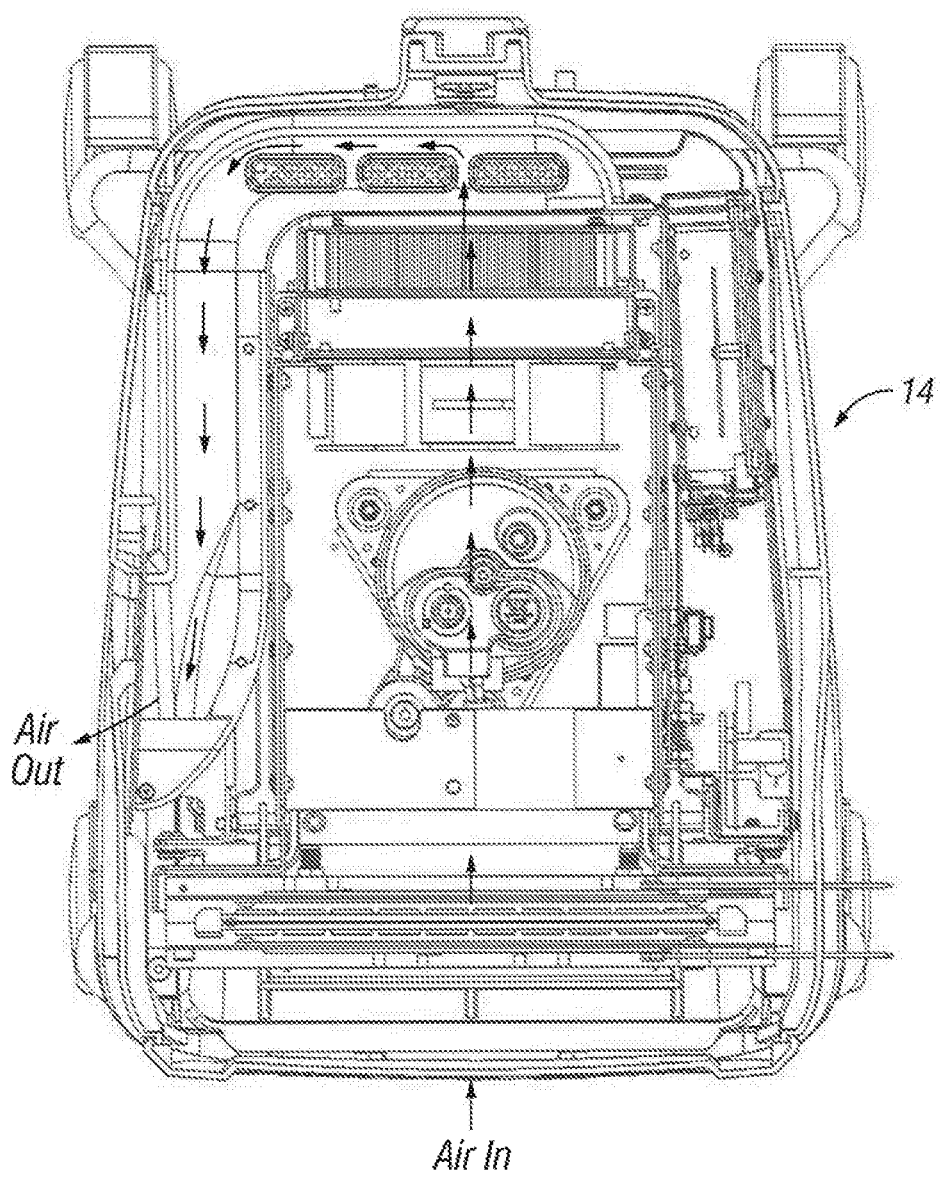

FIG. 8 is a top cross-sectional view of the control console.

Figure 9:
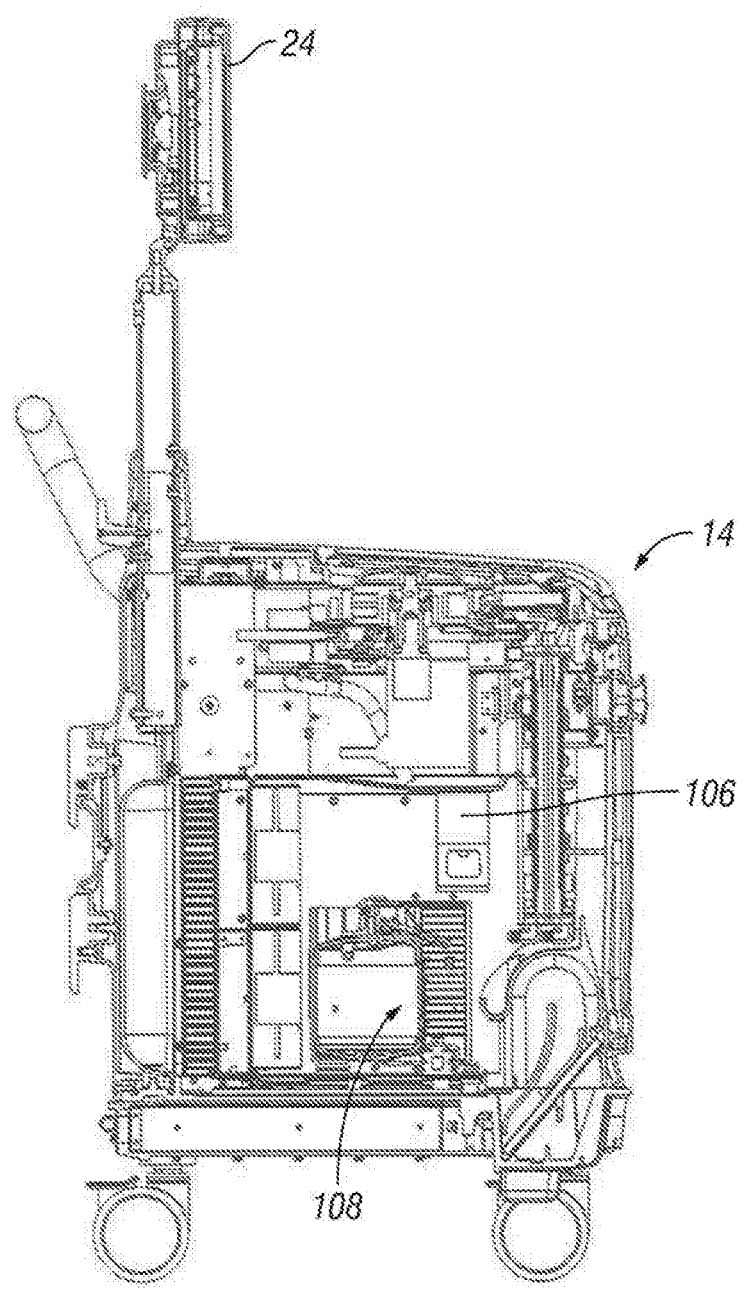

FIG. 9 is a right cross-sectional view of the control console.

Figure 10:
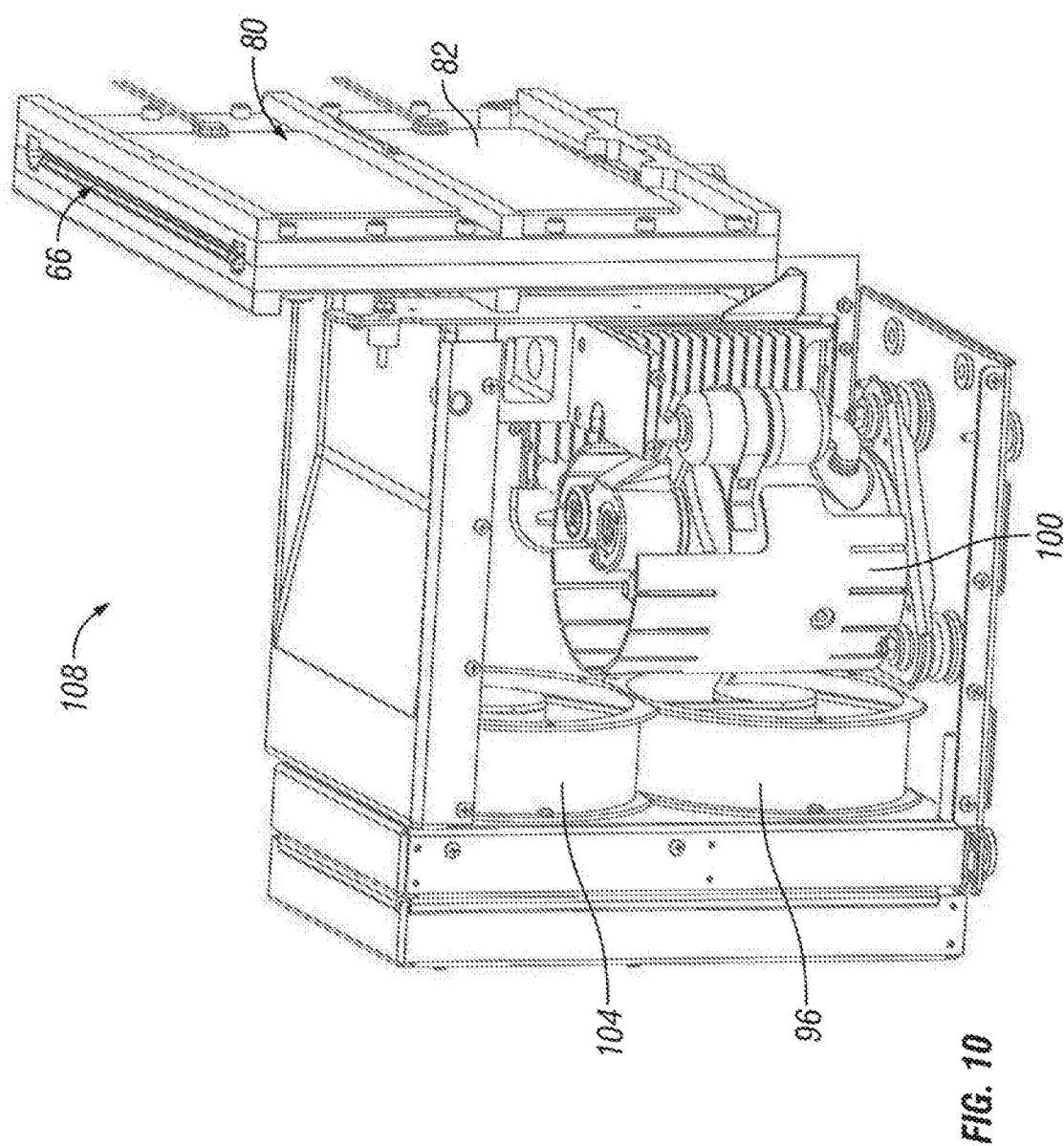

FIG. 10 is a perspective view of a thermal exchange engine component of the control console.

Figure 11:
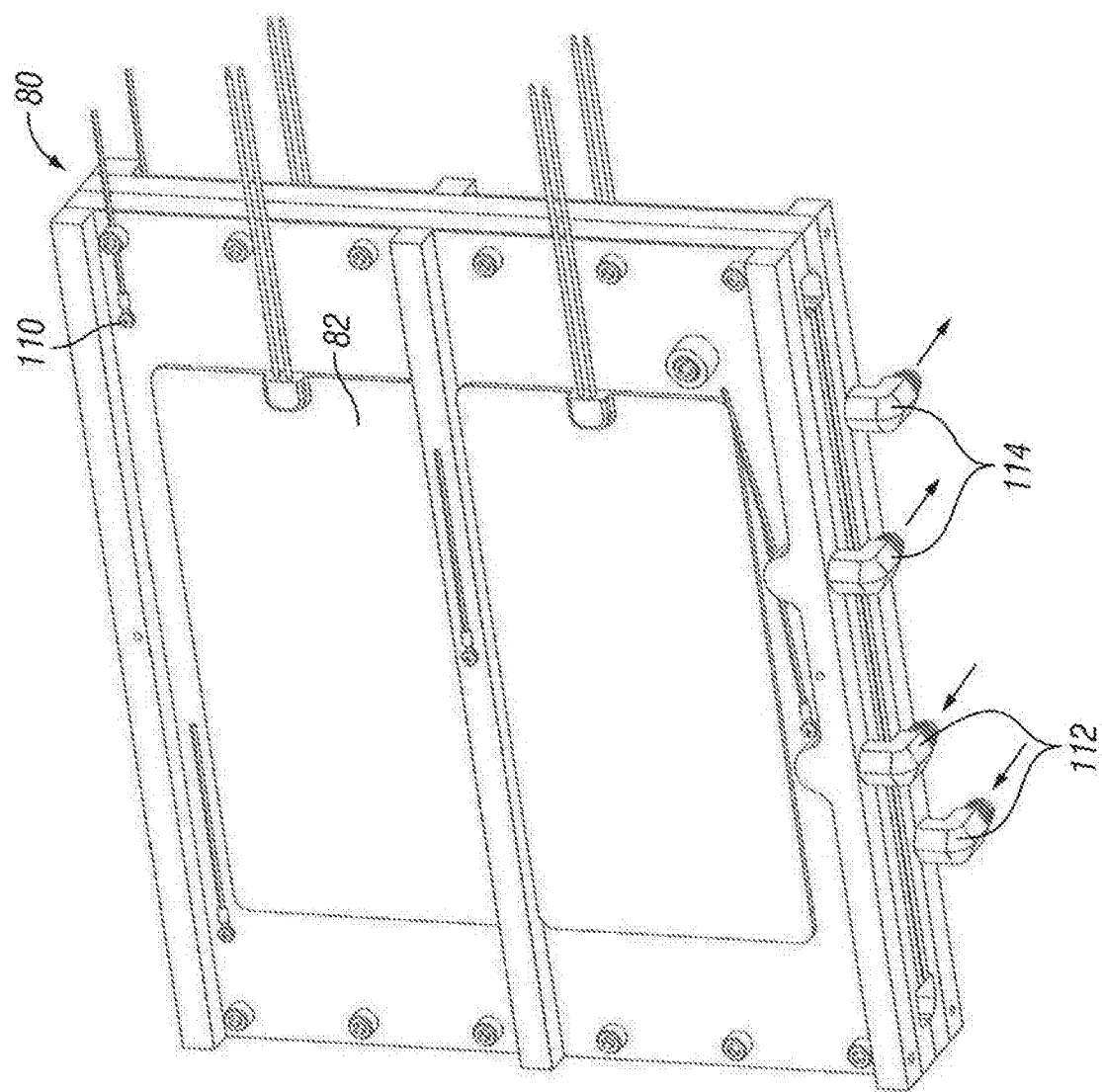

FIG. 11 is a bottom/perspective view of a thermal exchange plate assembly of the thermal exchange engine.

Figure 12:
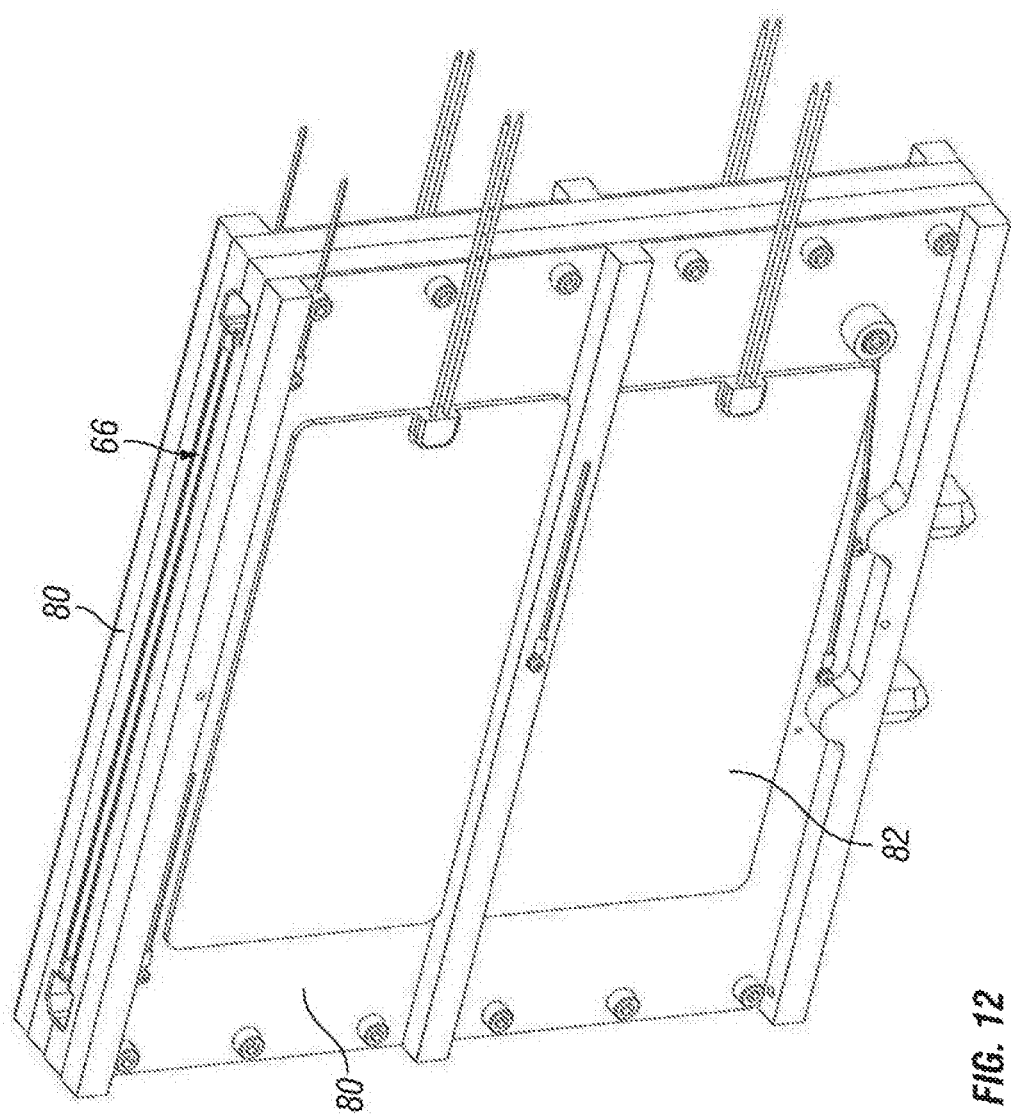

FIG. 12 is a top/perspective view of the thermal exchange plate assembly.

Figure 13:
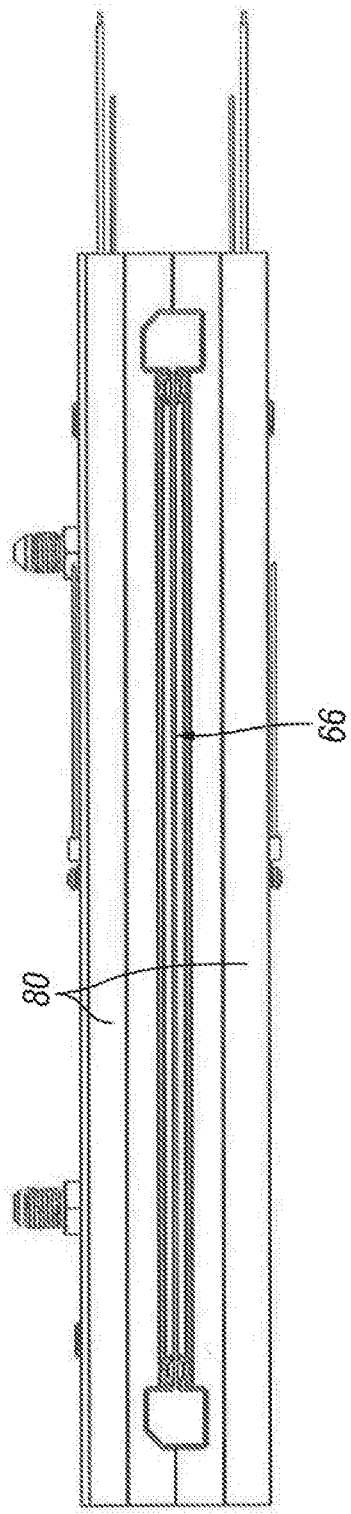

FIG. 13 is a top (plan) view of the thermal exchange plate assembly of the thermal exchange engine.

Figure 14:
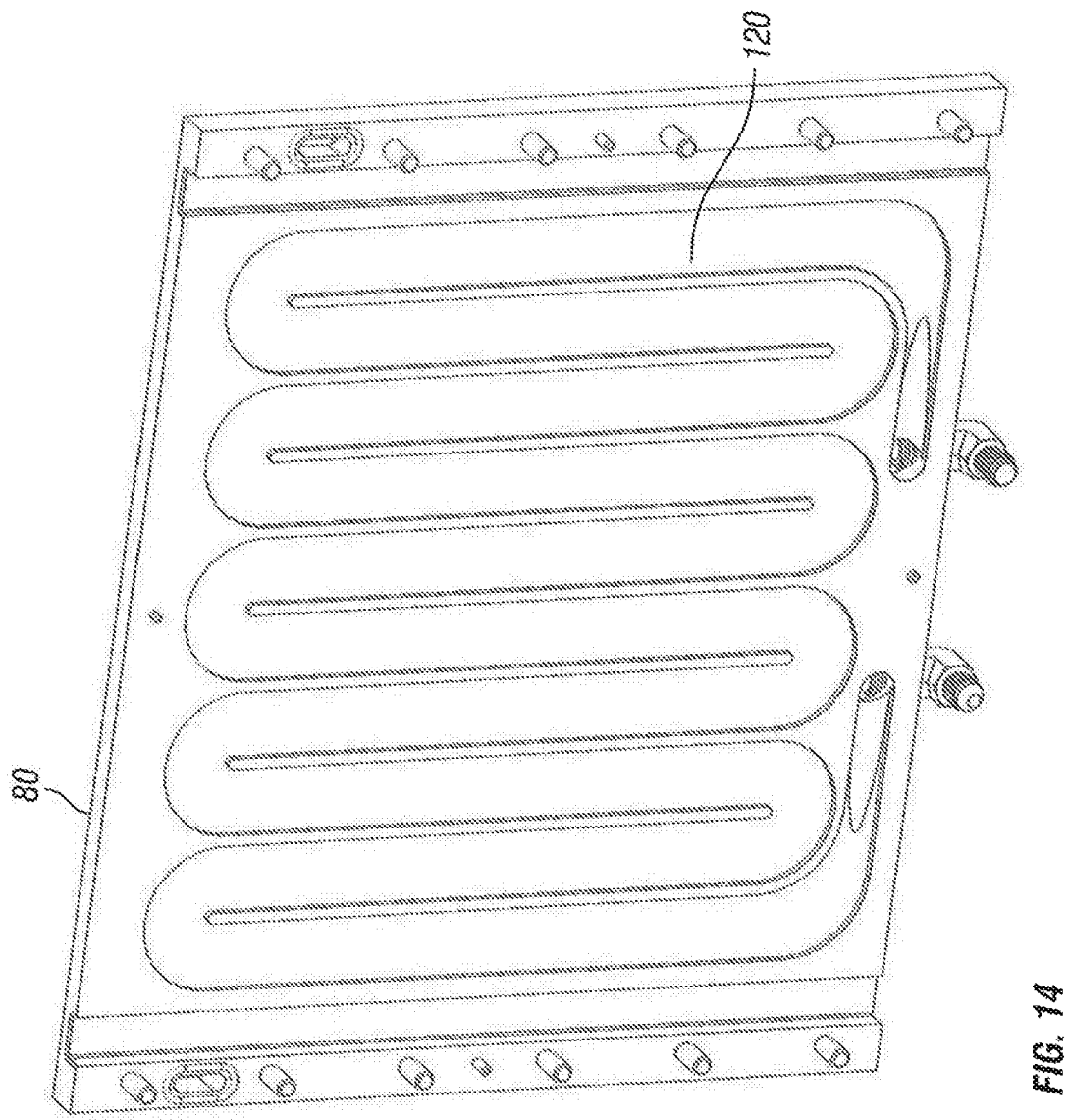

FIG. 14 is disassembled view of one of the thermal exchange plates of the thermal exchange plate assembly, exposing a vertically oriented serpentine refrigerant flow path formed in the inner surface of the plate.

Figure 15:
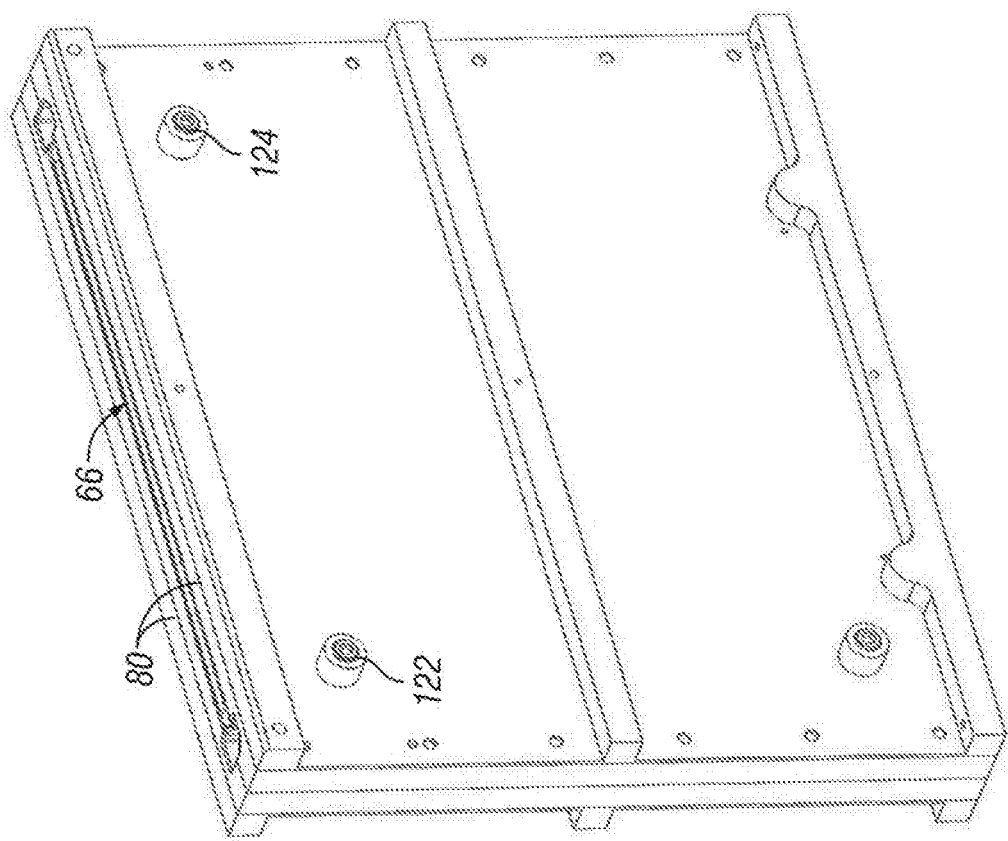

FIG. 15 is a rear view of the thermal exchange plate assembly with the outer plate and heater removed.

Figure 16:
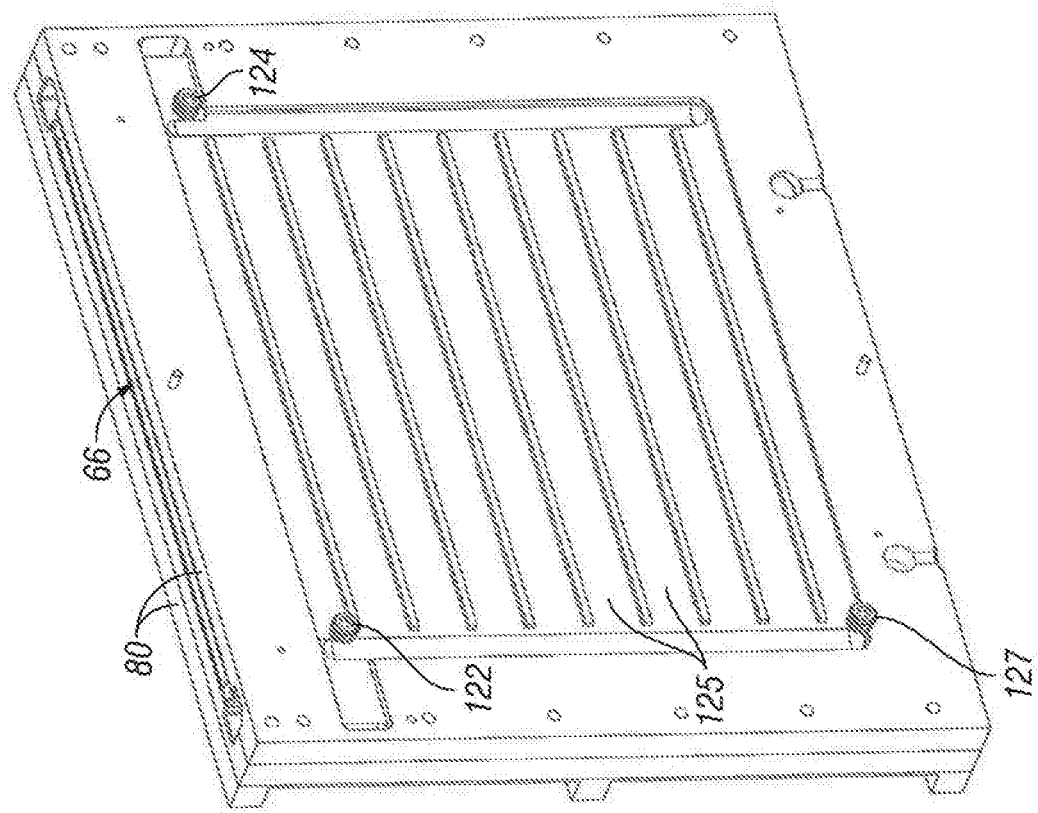

FIG. 16 is a partially disassembled rear perspective view of with the thermal exchange plate wherein rear plates have been removed so as to expose secondary fluid flow channels useable for optional non-cassette warming/cooling of a fluid.

Figure 17:
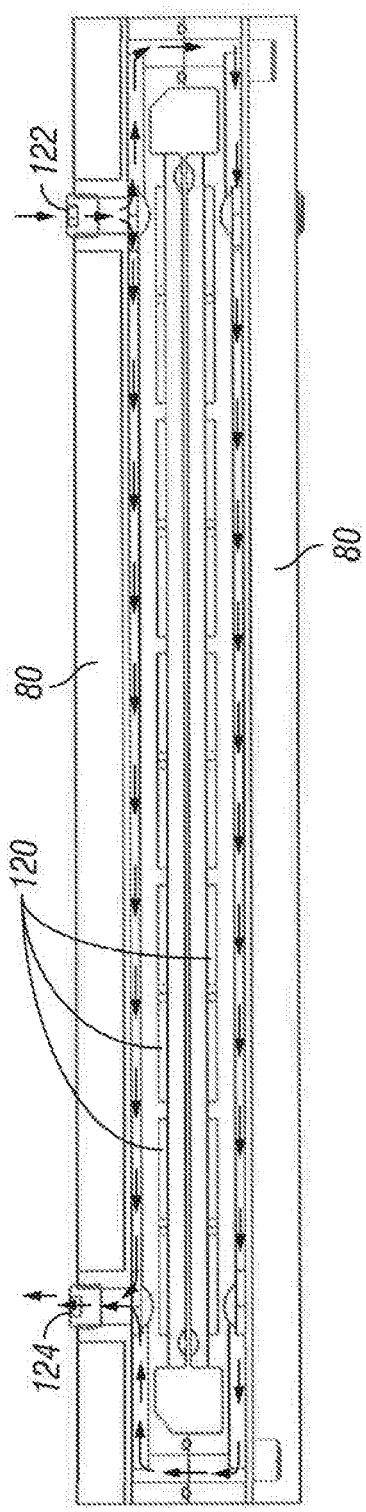

FIG. 17 is a top view of the fully assembled thermal exchange plate assembly.

Figure 18:
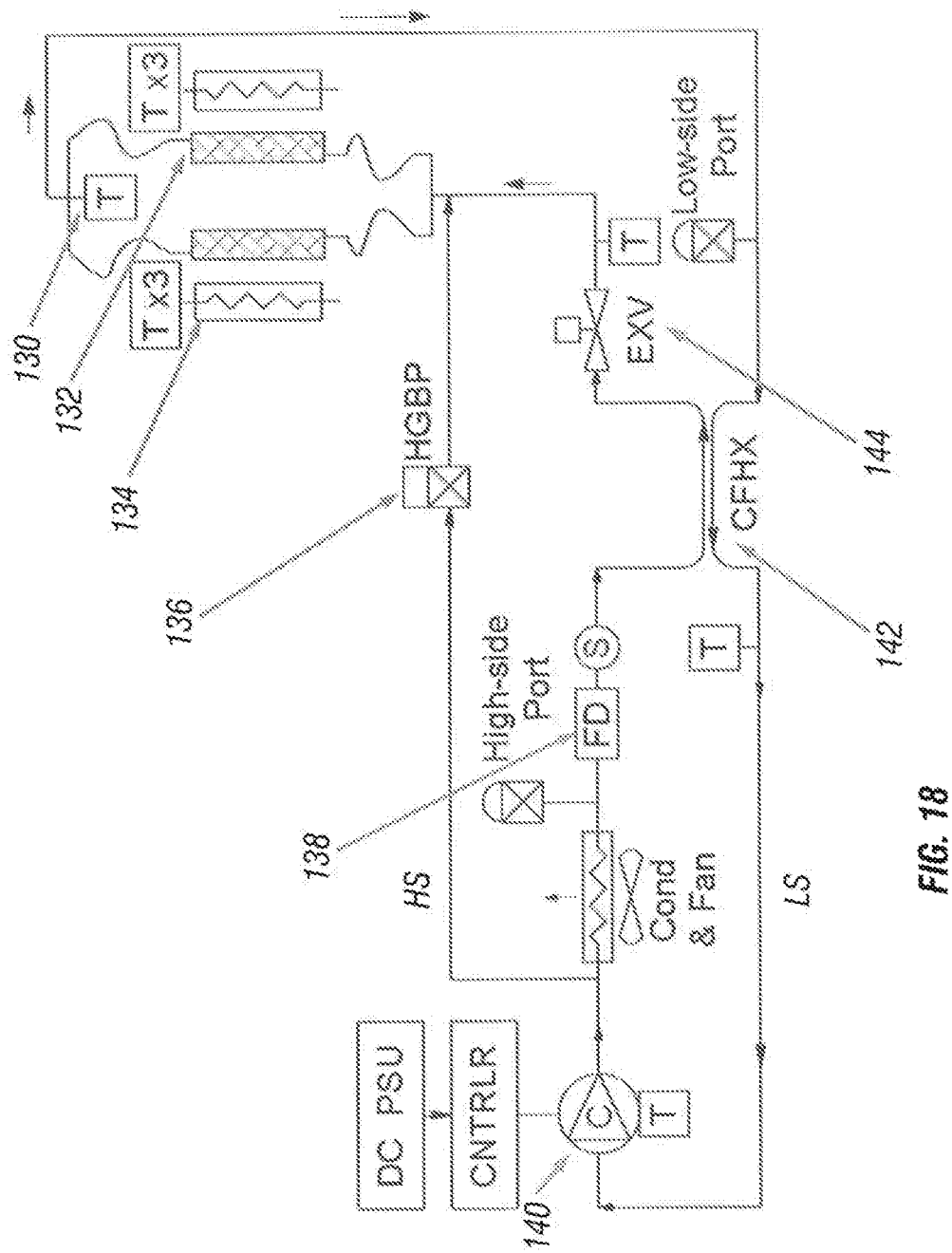

FIG. 18 is a schematic diagram illustrating the functional lay out of the thermal exchange engine.

Figure 19:
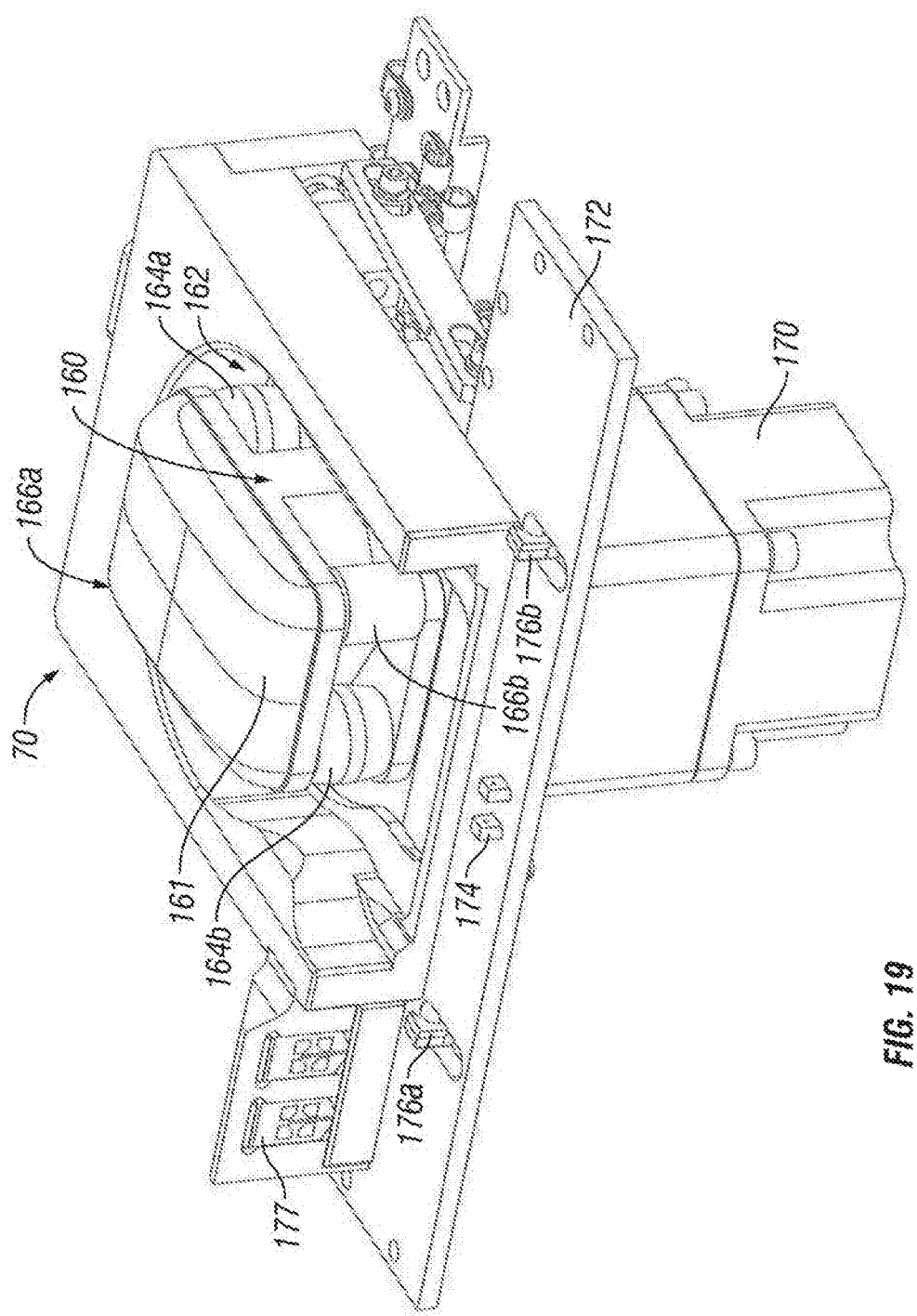

FIG. 19 is a front perspective view of the pump assembly of extracorporeal control console.

Figure 20:
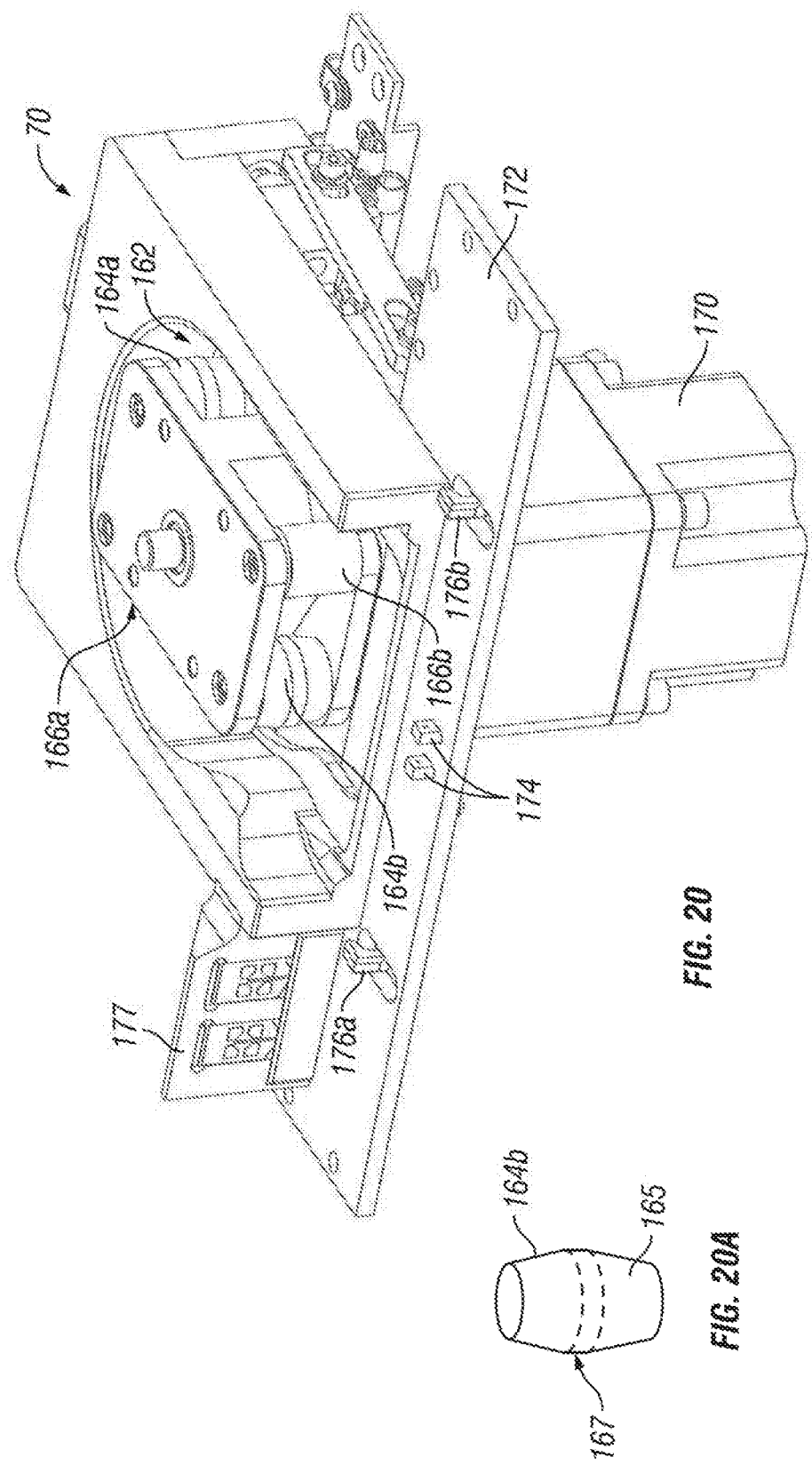

FIG. 20 is a partially disassembled view of the pump assembly wherein the cover has been removed.

FIG. 20A is a separate view of a barrel-shaped guide roller of the pump assembly.

Figure 21:
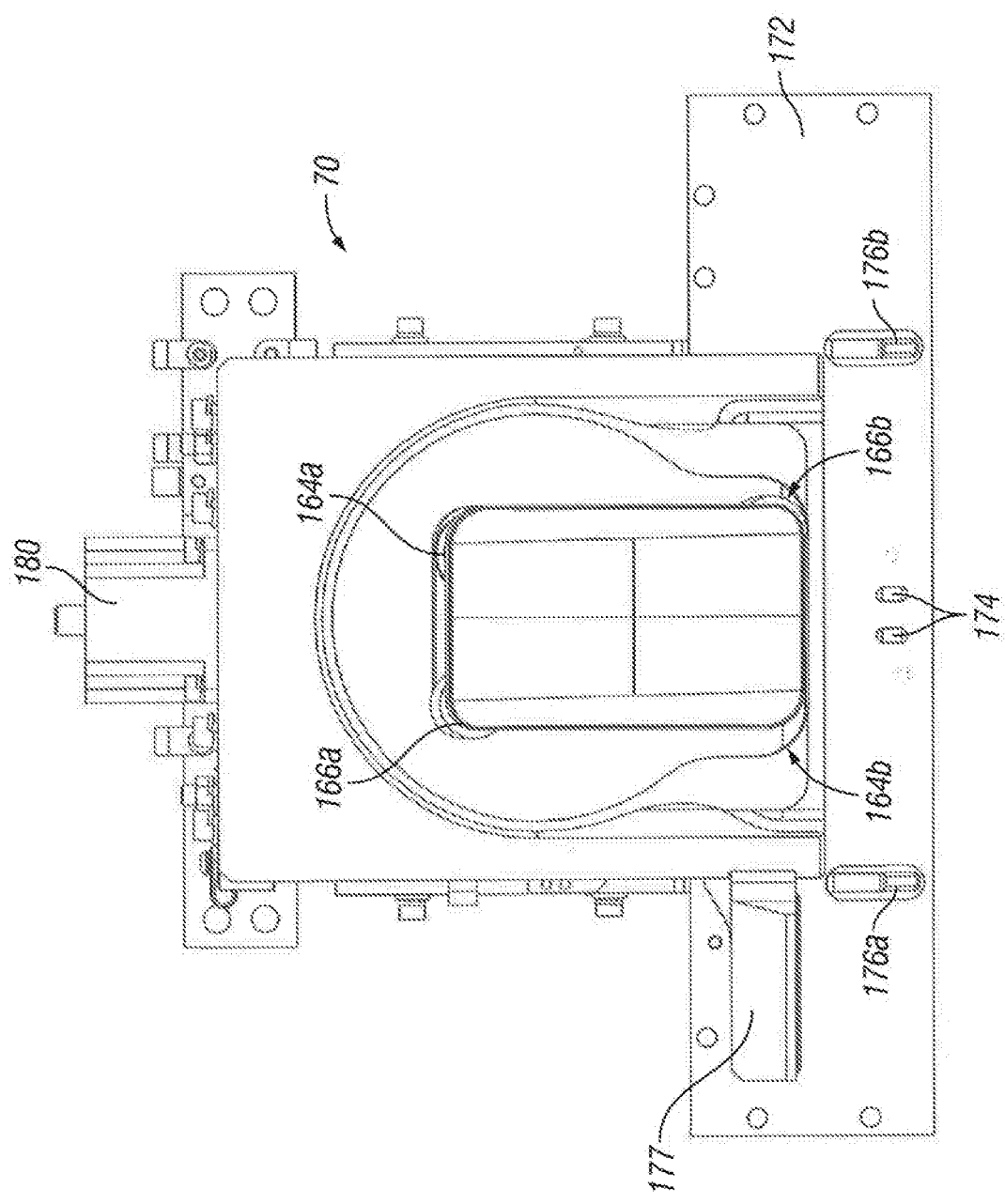

FIG. 21 is a top view of the pump assembly.

Figure 22:
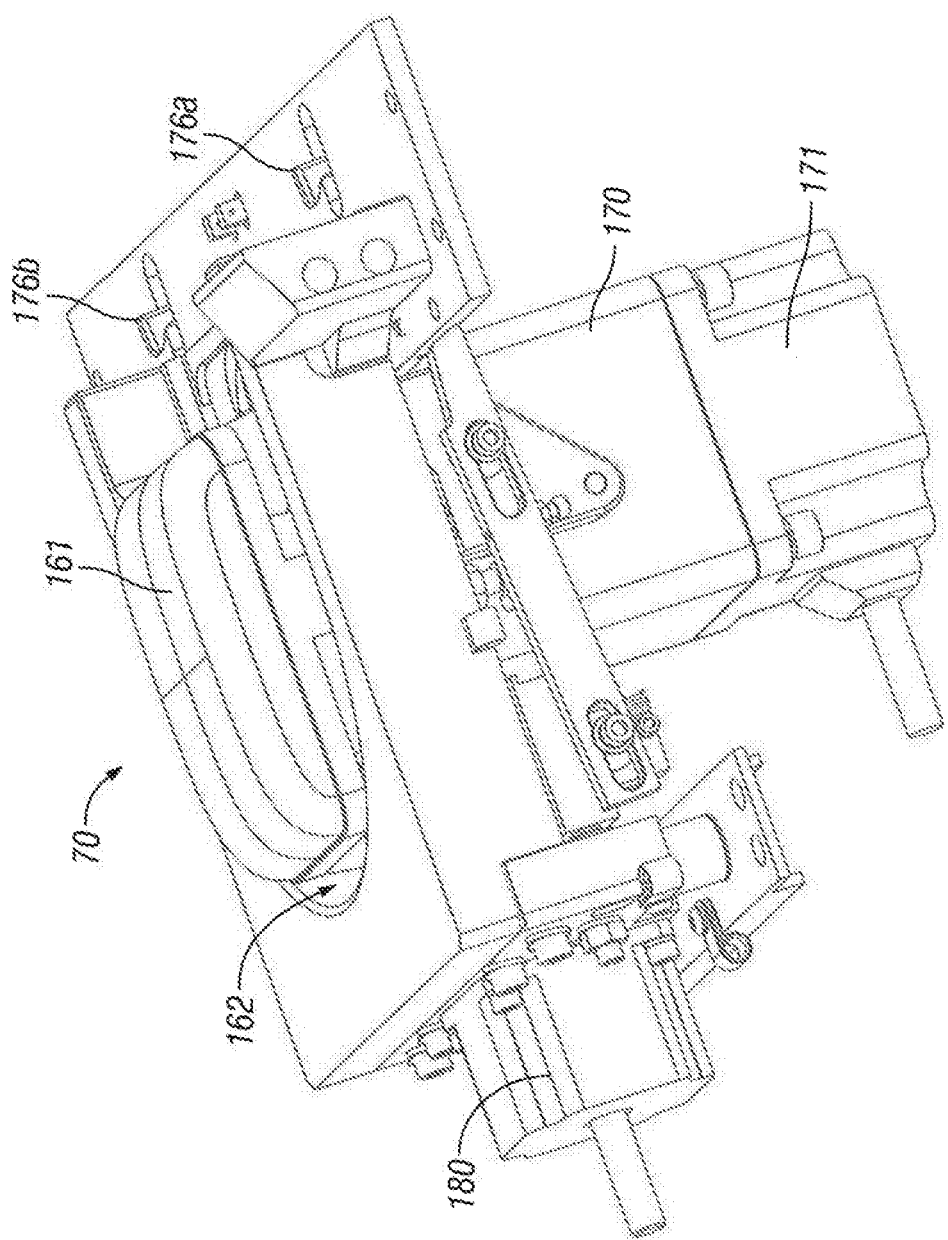

FIG. 22 is a rear perspective view of the pump assembly disposed in an operative configuration.

Figure 23:
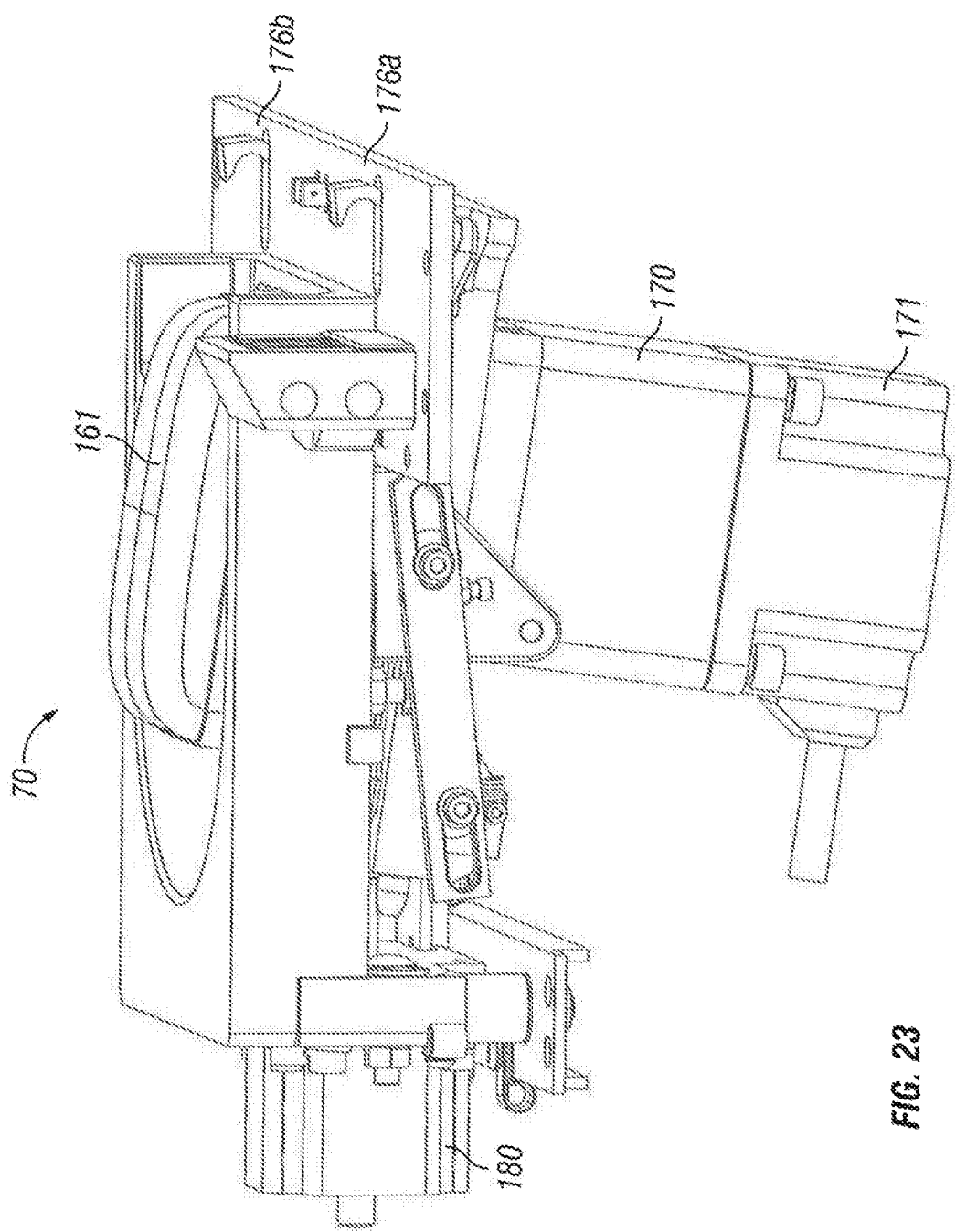

FIG. 23 is a rear perspective view of the pump assembly disposed in a loading configuration.

Figure 24:
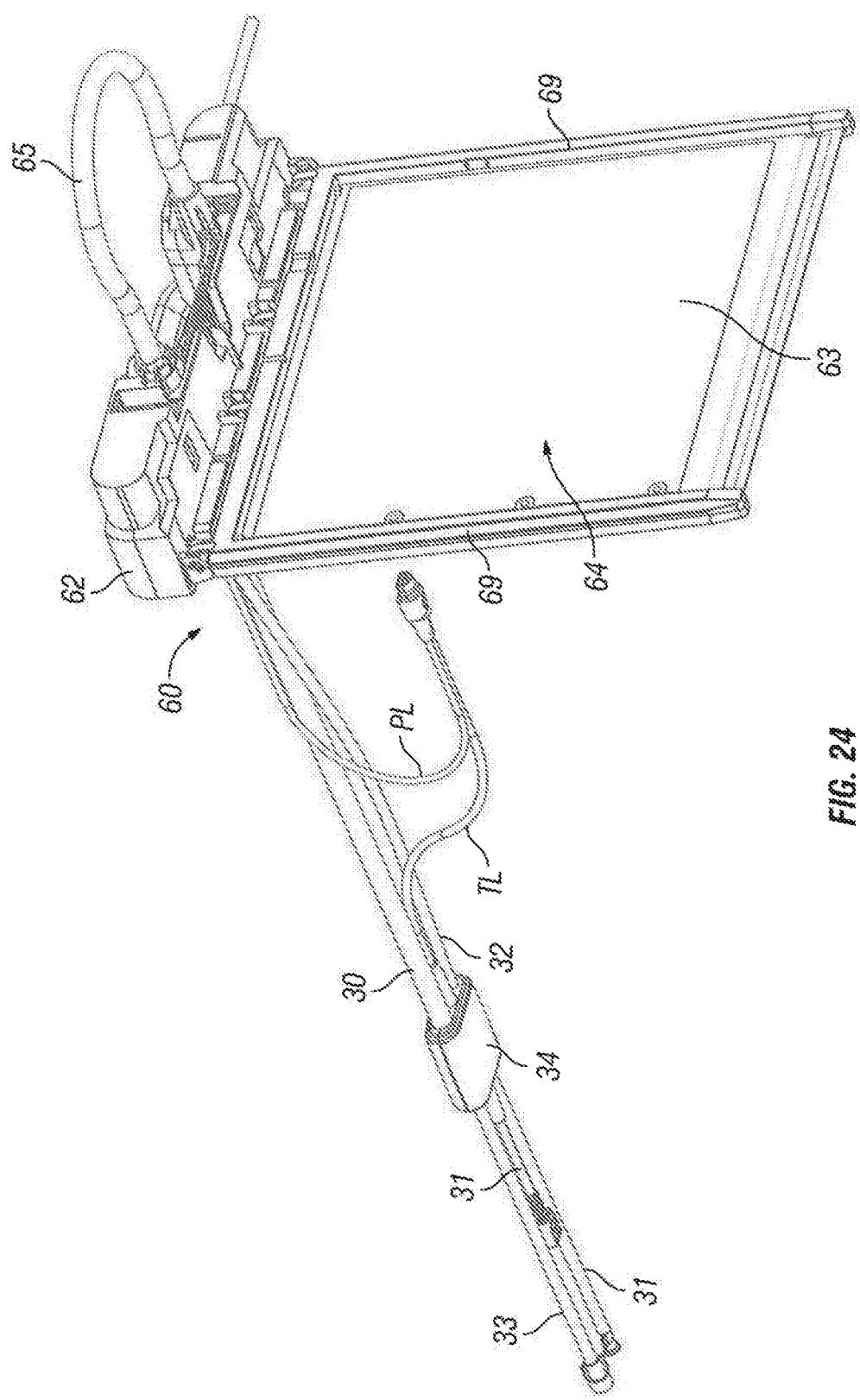

FIG. 24 is a rear perspective view of the tubing/cassette/sensor module assembly of the endovascular heat exchange system.

Figure 25:
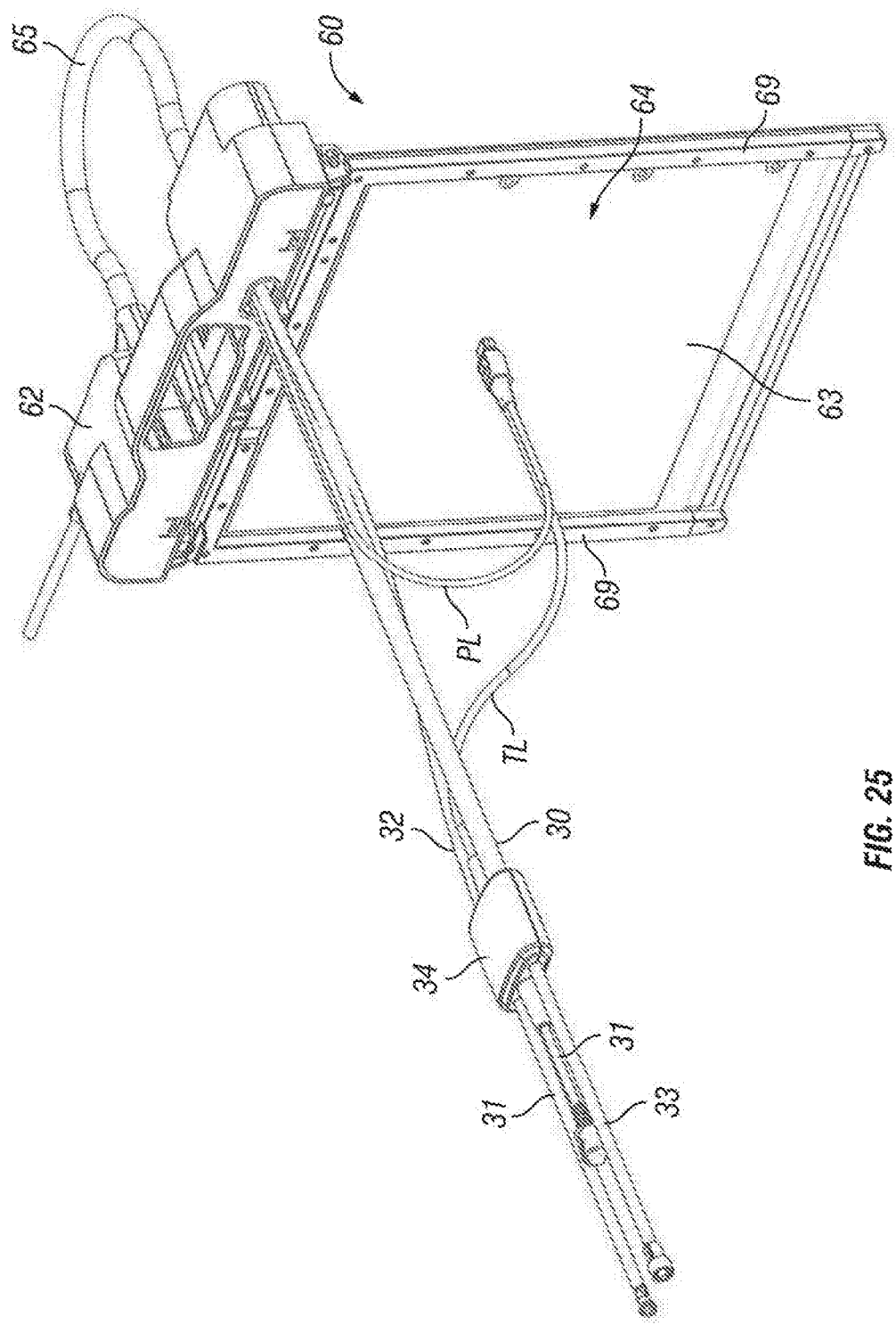

FIG. 25 is a front perspective view of the tubing/cassette/sensor module assembly.

Figure 26:
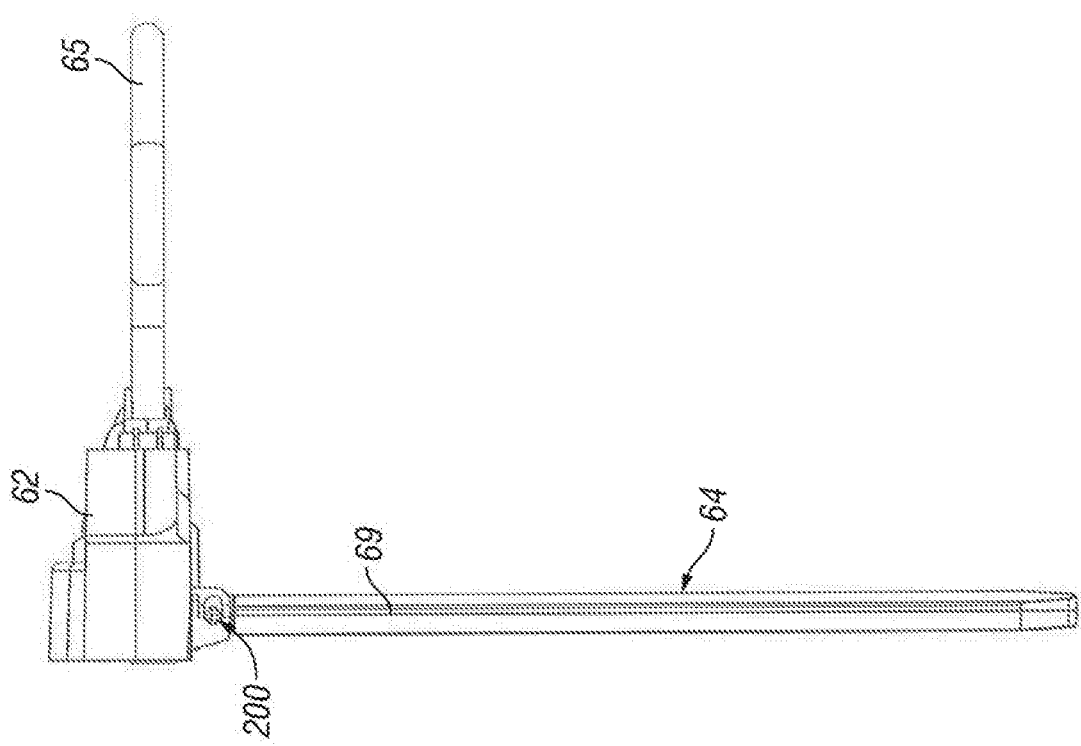

FIG. 26 is a side view of the cassette and pump tubing portions of the tubing/cassette/sensor module assembly disposed in an open/locked configuration useable for insertion and operation.

Figure 27:
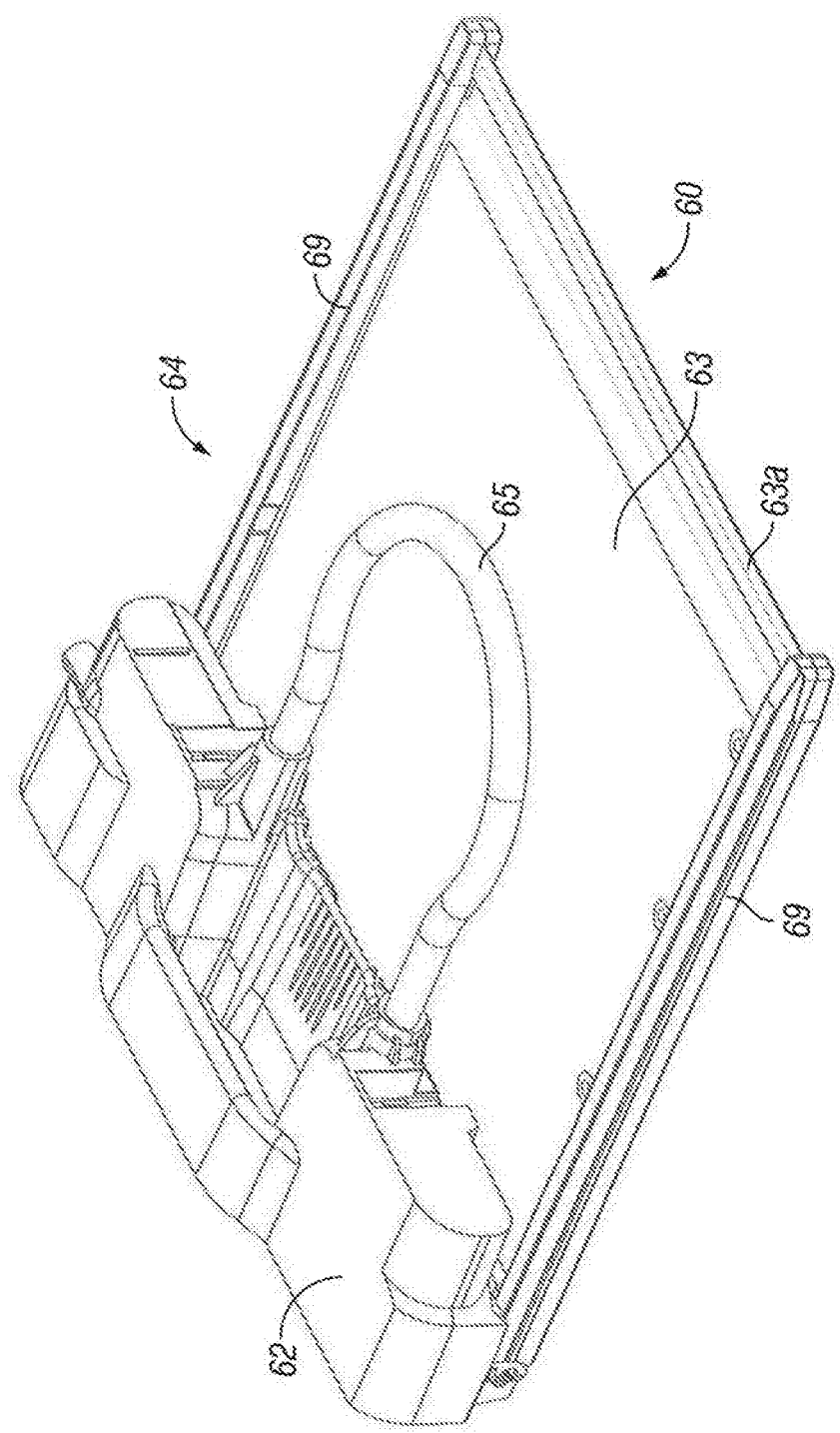

FIG. 27 is a rear perspective view of the cassette and pump tubing portions of the tubing/cassette/sensor module assembly disposed in a closed configuration prior to insertion and operation.

Figure 28:
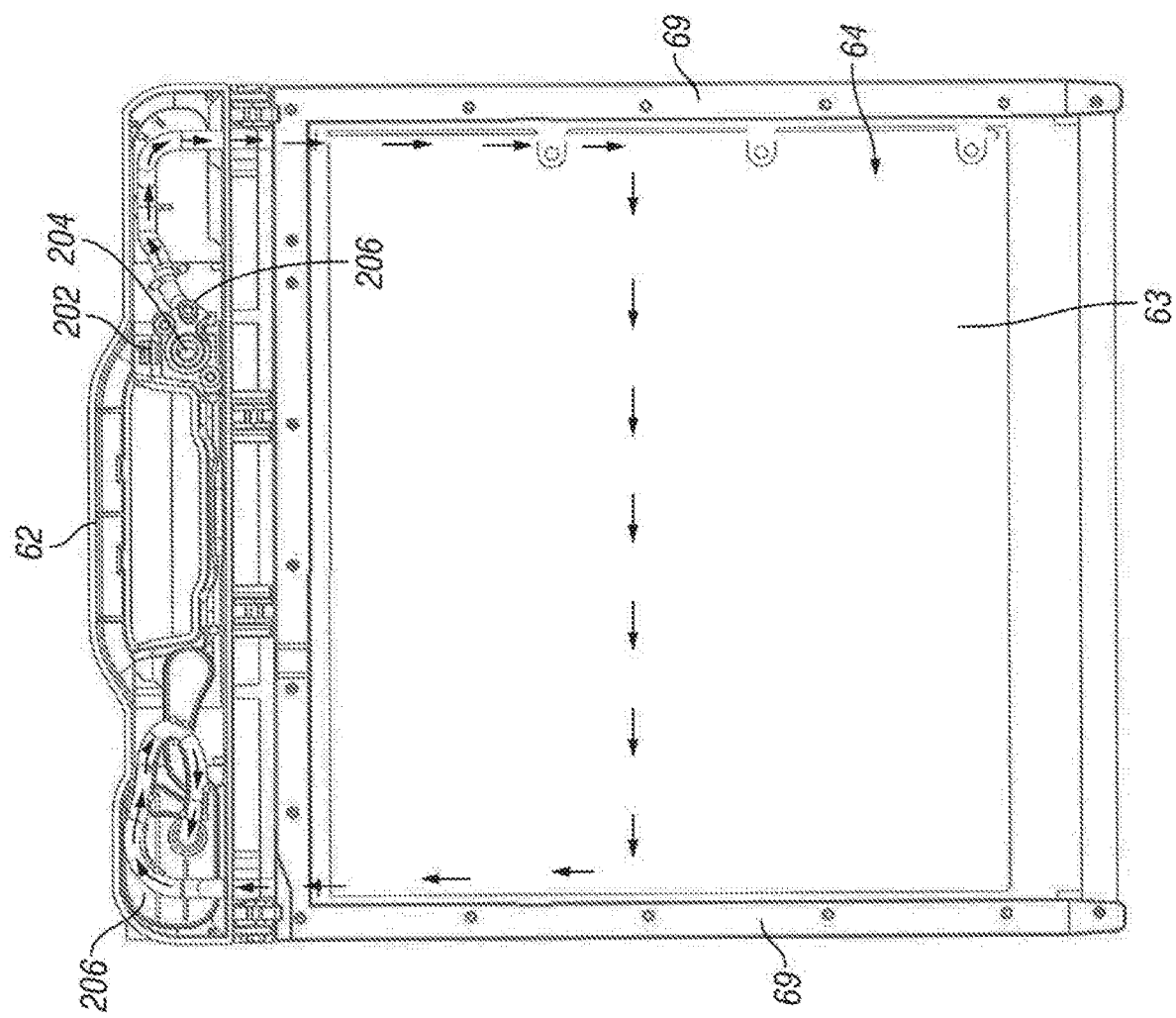

FIG. 28 is a cross sectional view of the cassette portion of the tubing/cassette/sensor module assembly.

Figure 29:
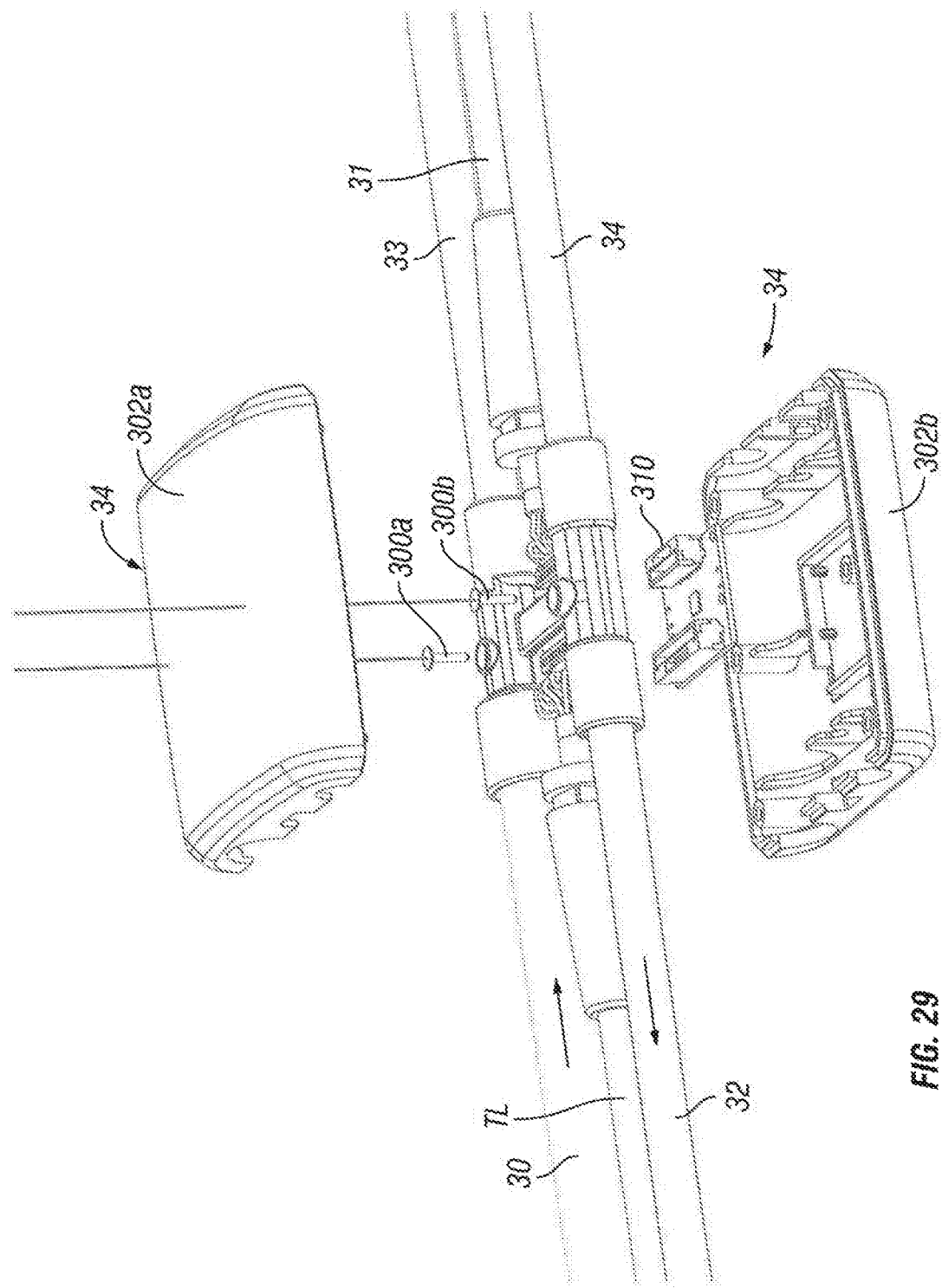

FIG. 29 is an exploded view of the sensor module portion of the tubing/cassette/sensor module assembly.

Figure 30:
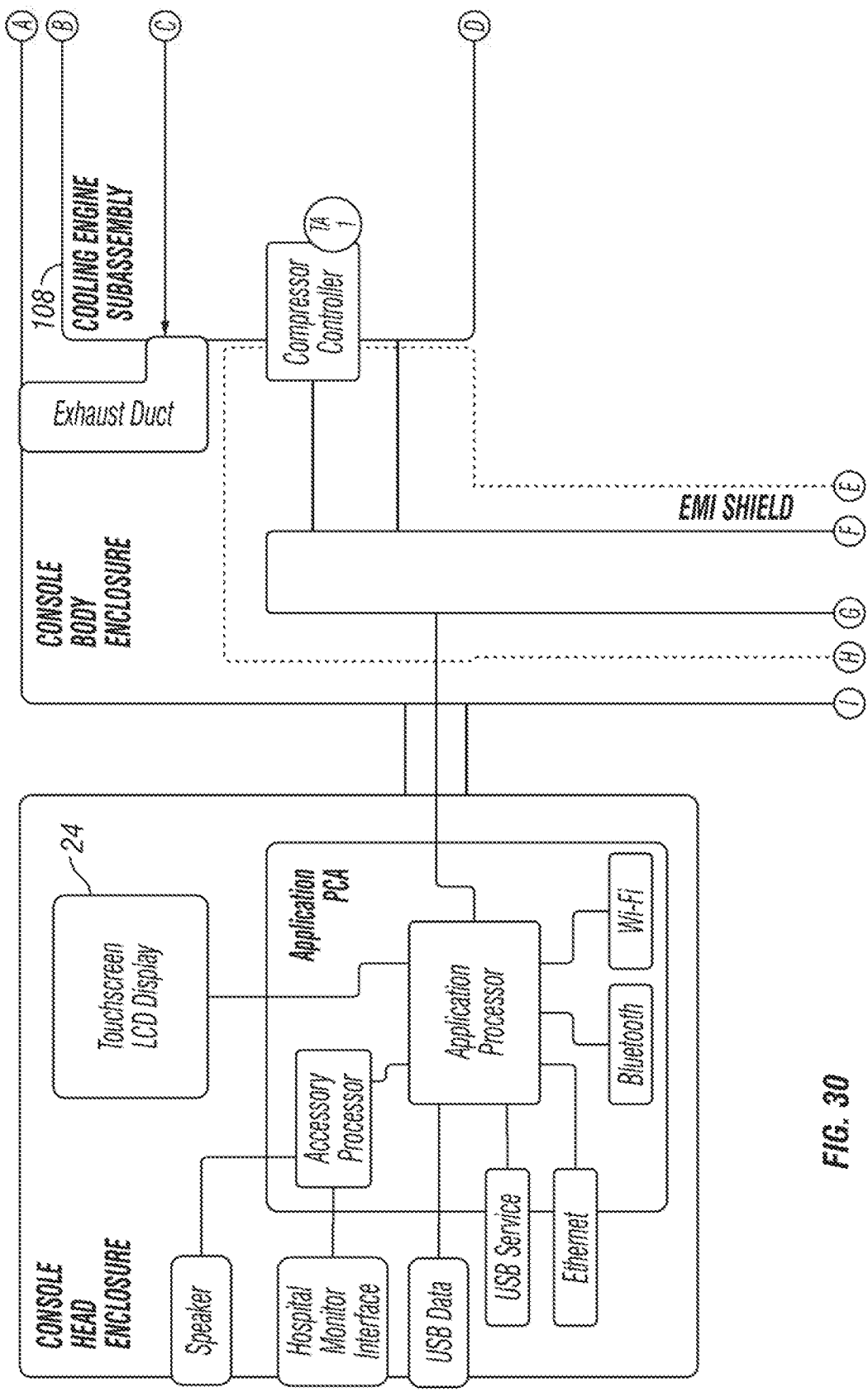
Figure 30:
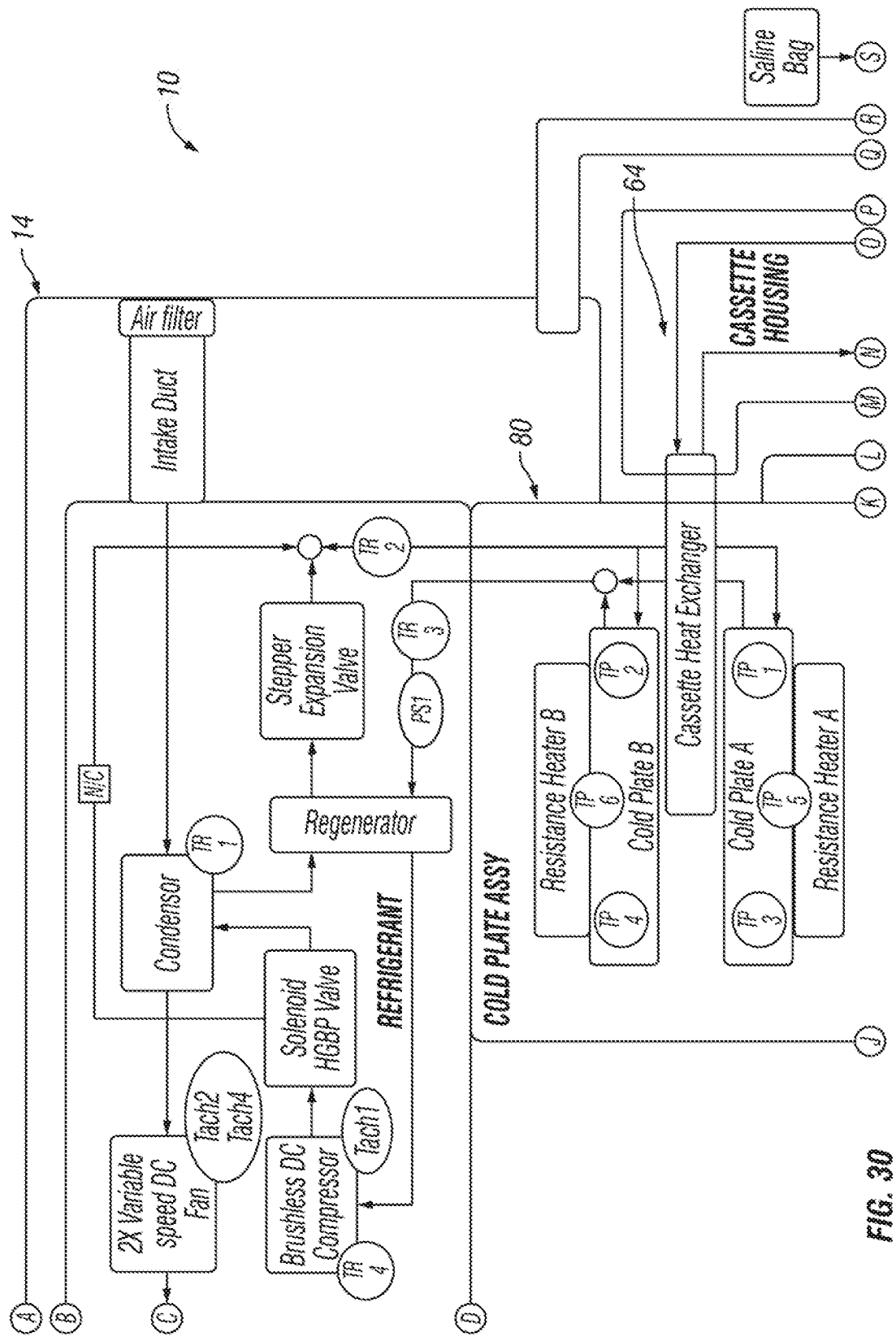
Figure 30:
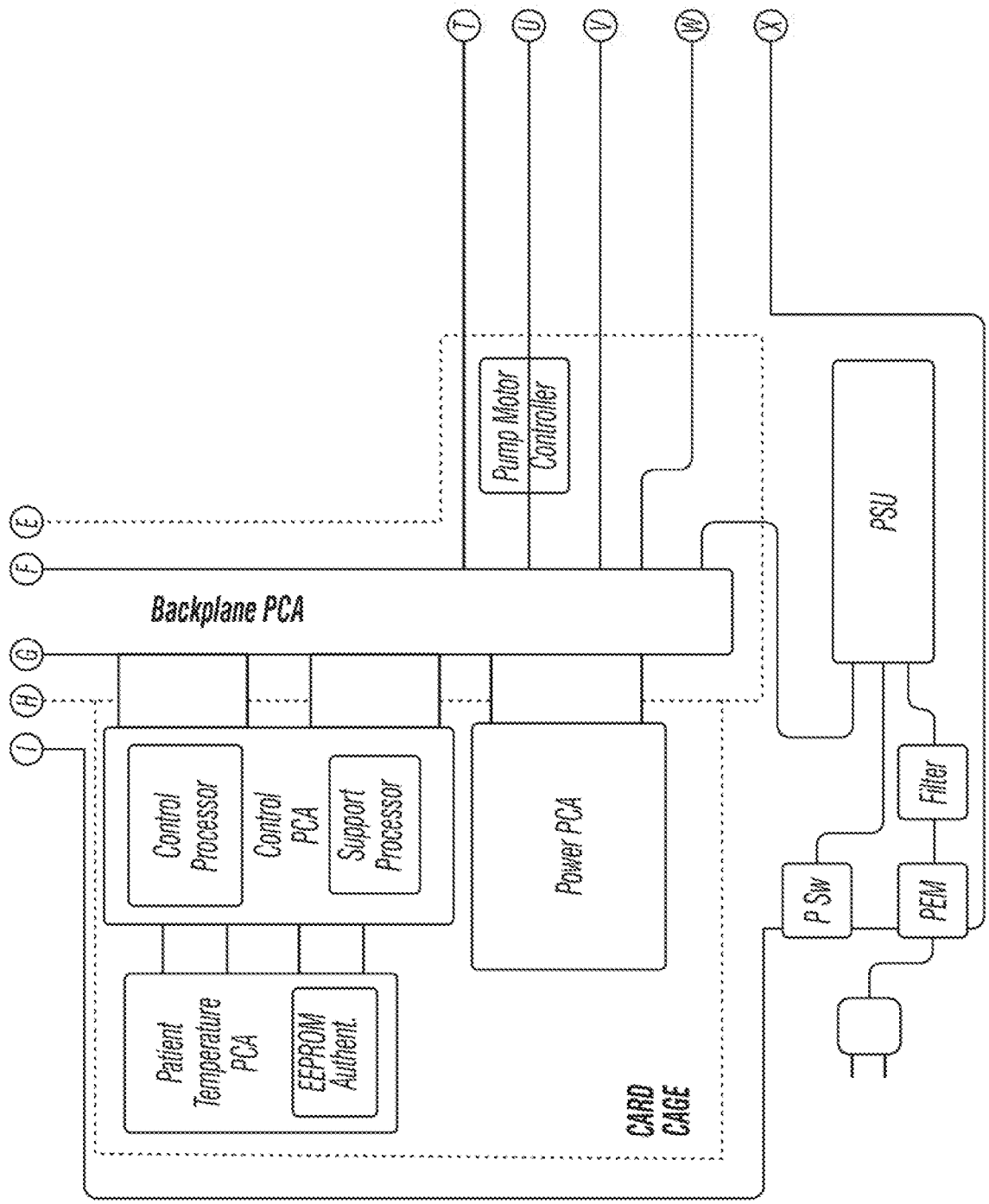
Figure 30:
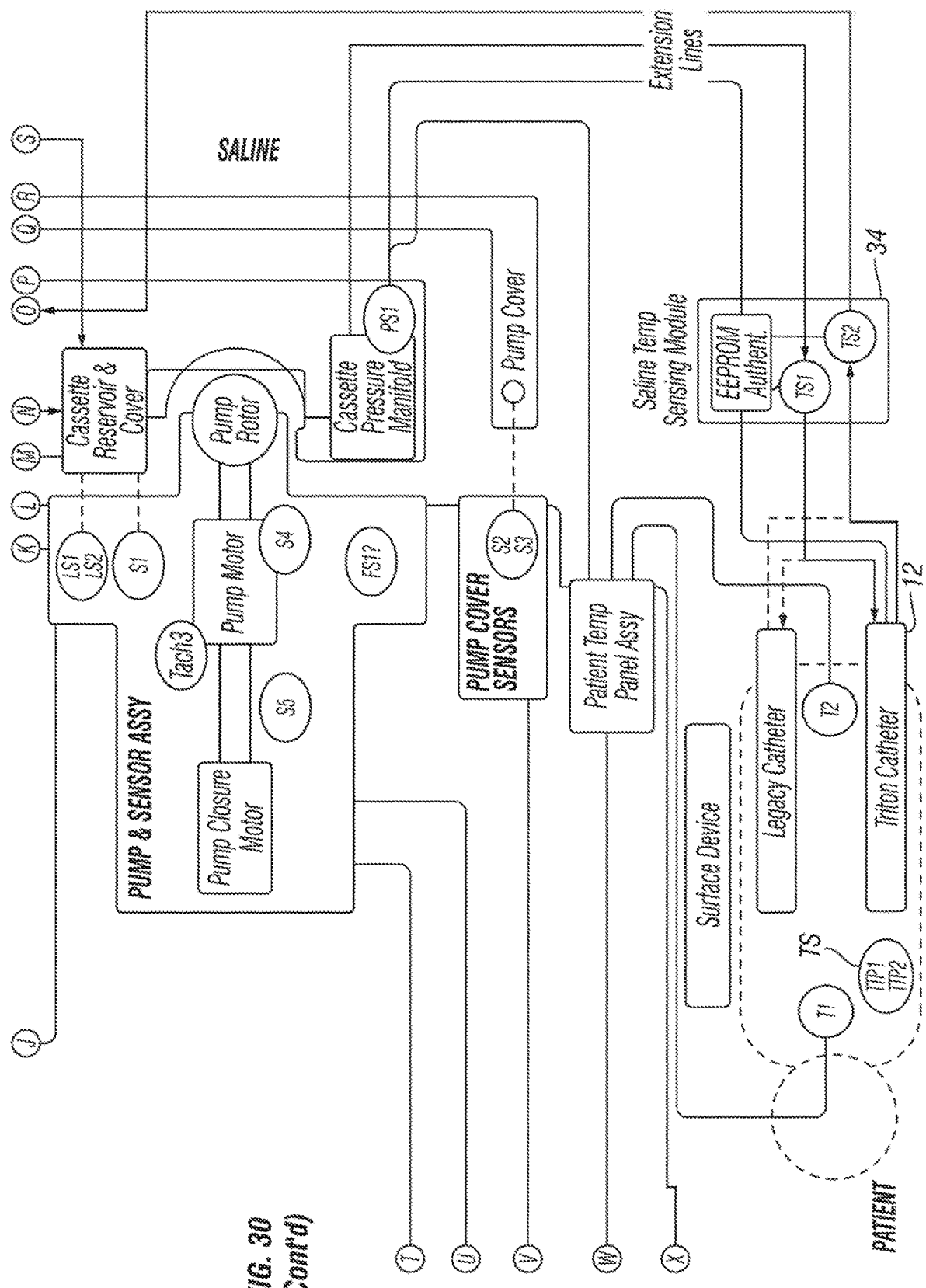

FIG. 30 is a schematic diagram of an endovascular heat exchange system. (convert to black/white formalize)

Figure 31:
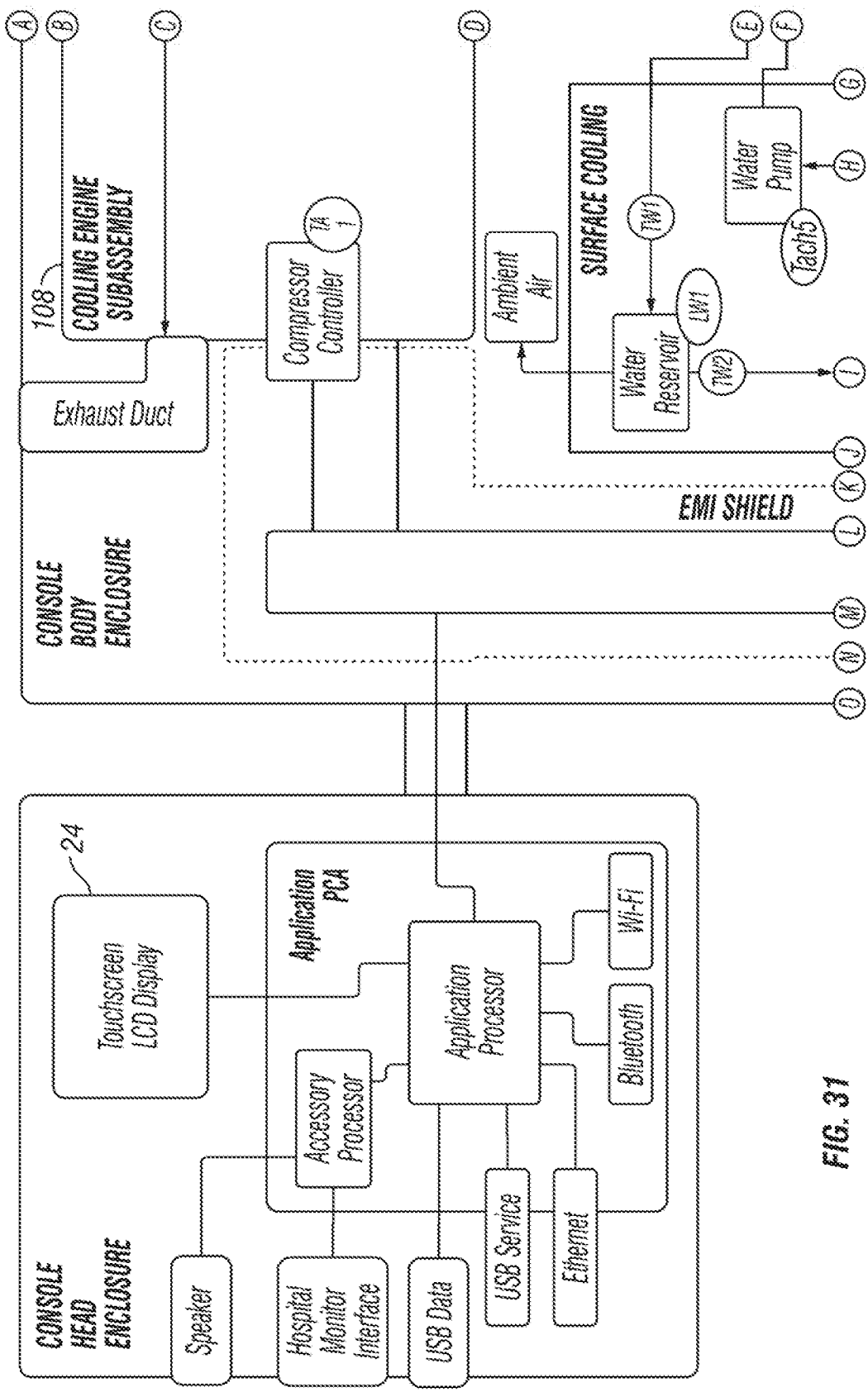
Figure 31:
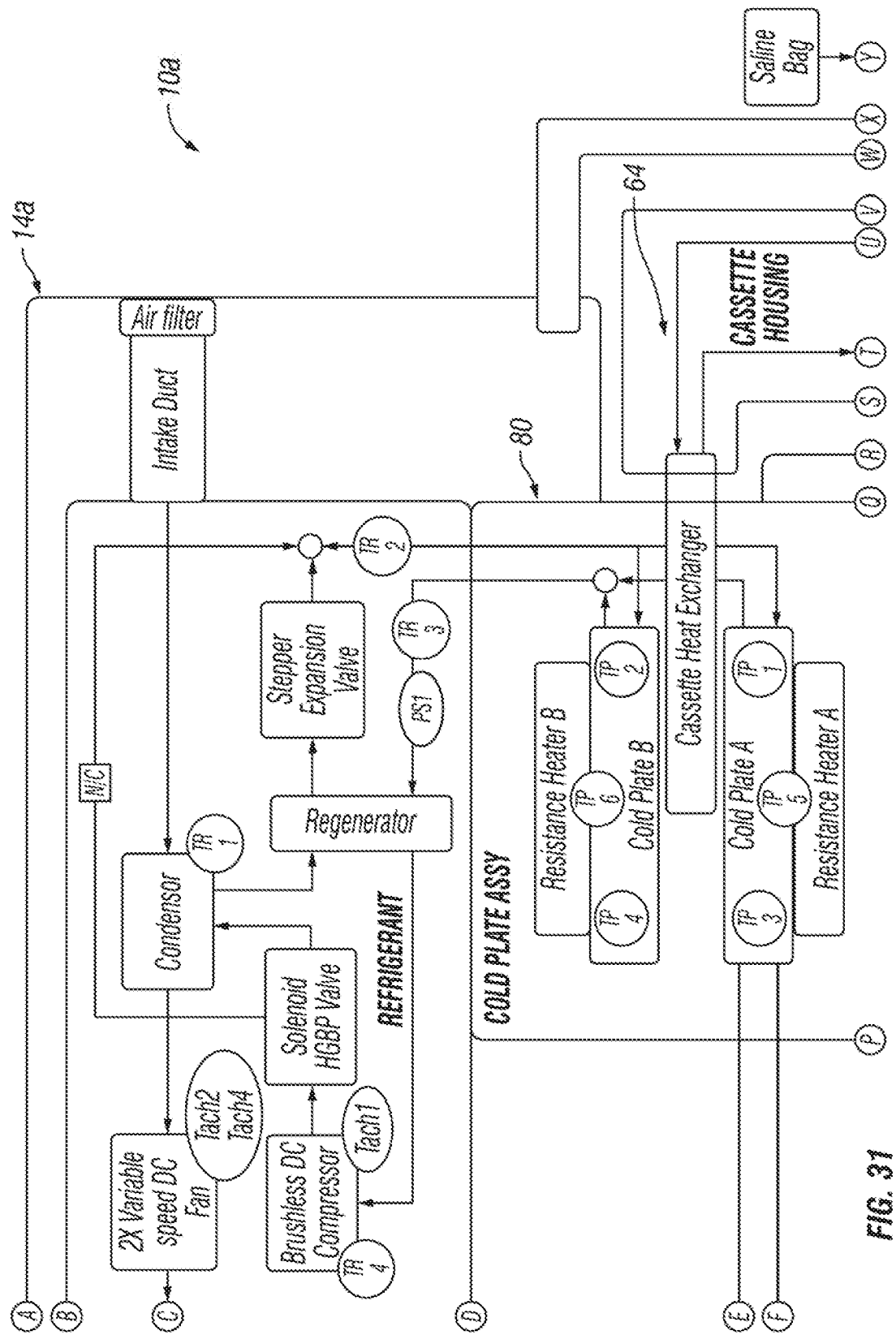
Figure 31:
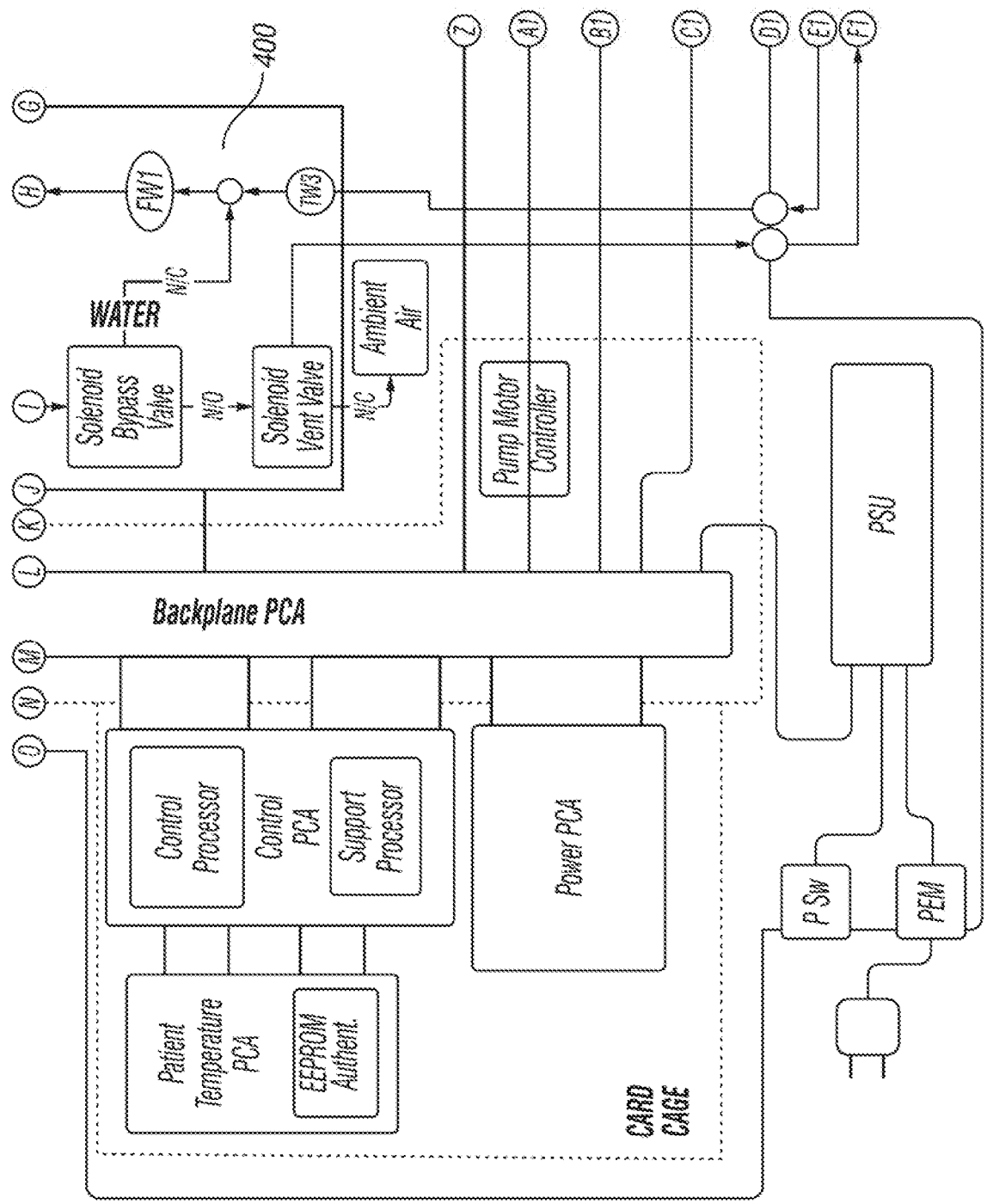

FIG. 31 is a schematic diagram of a heat exchange system capable of providing endovascular and/or body surface heat exchange.

Figure 1:
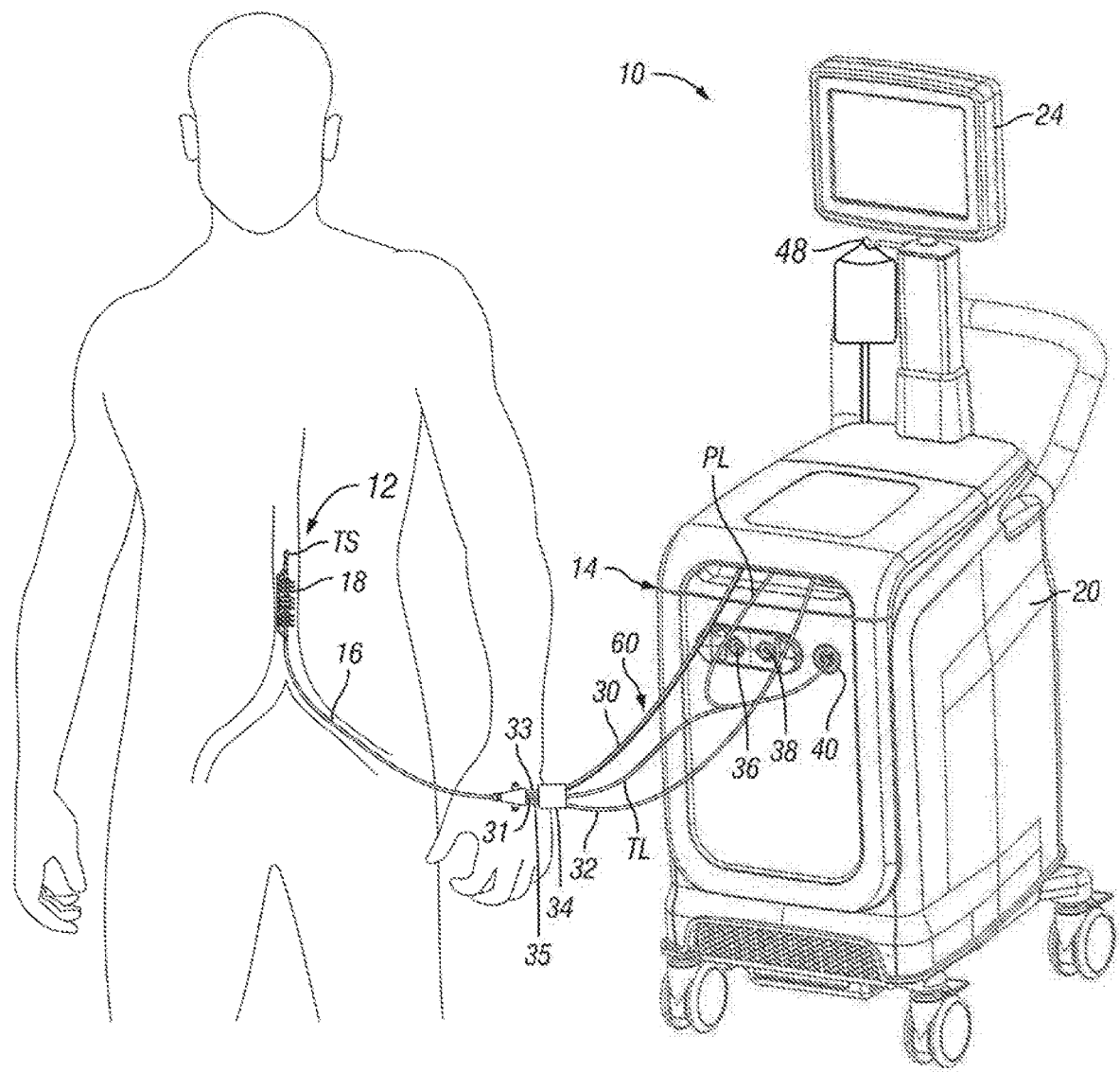
FIG. 1 shows one embodiment of an endovascular heat exchange system comprising an endovascular heat exchange catheter, an extracorporeal control console and a tubing/cassette/sensor module assembly useable for operatively connecting the heat exchange catheter to the control console.

FIG. 32 shows the heat exchange catheter of the system of FIG. 1.

FIG. 32A is a cross-sectional view through line A-A of FIG. 32.

FIG. 32B is a cross-sectional view through line B-5 of FIG. 32.

FIGS. 33A through 33O show certain components of the endovascular heat exchange catheter embodiment of FIG. 32. Specifically, FIG. 33A is a side view of the elongate member; FIG. 33B is a side view of the heat exchange tube and FIG. 33C is a side view of an optional elongate luminal member and the distal tip member.

Figure 34:
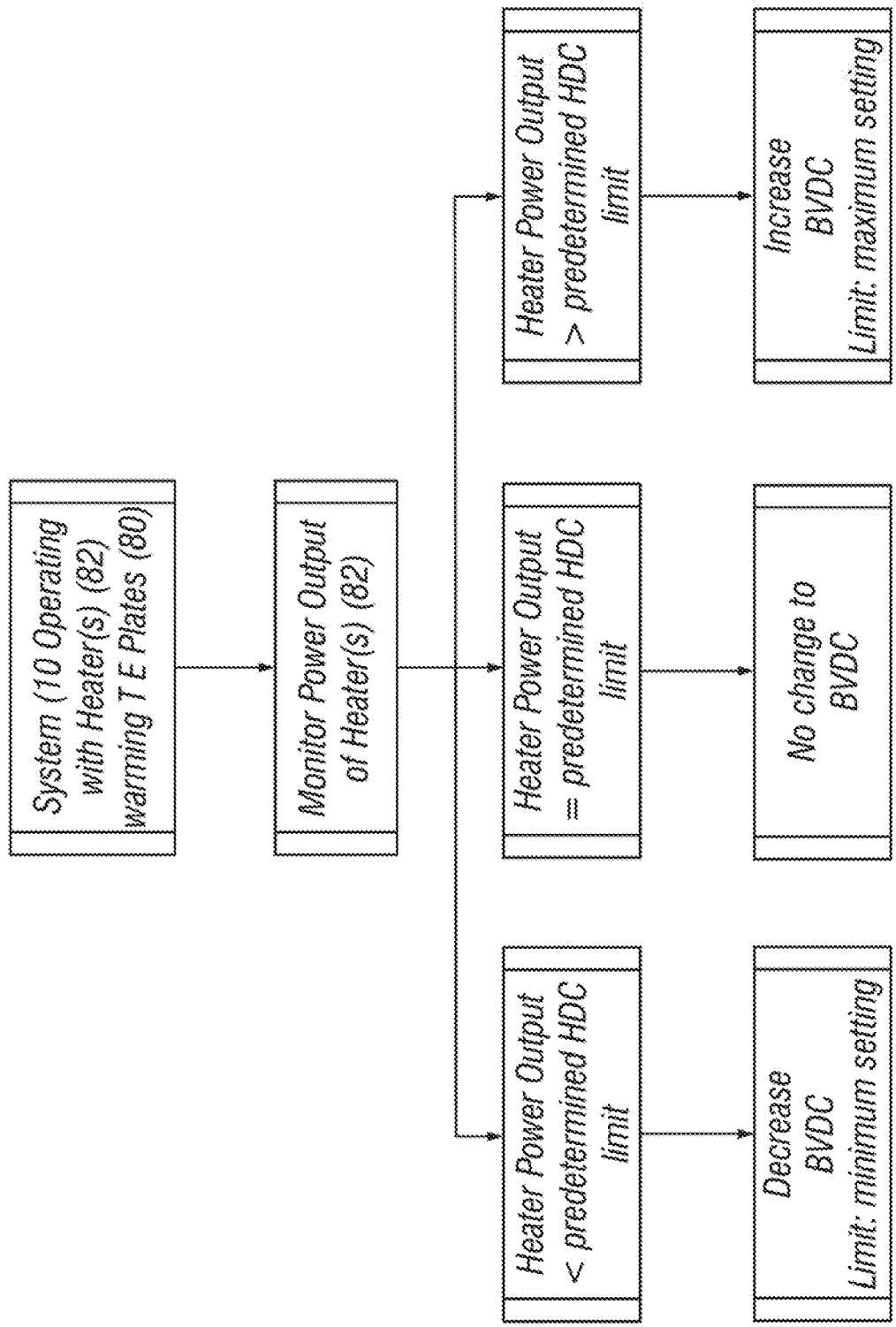

FIG. 34 is a flow diagram showing one example of a process by which a body heat exchange system may employ hot refrigerant from its cooling engine to augment the warming effect of resistance heaters.

Figure 35:
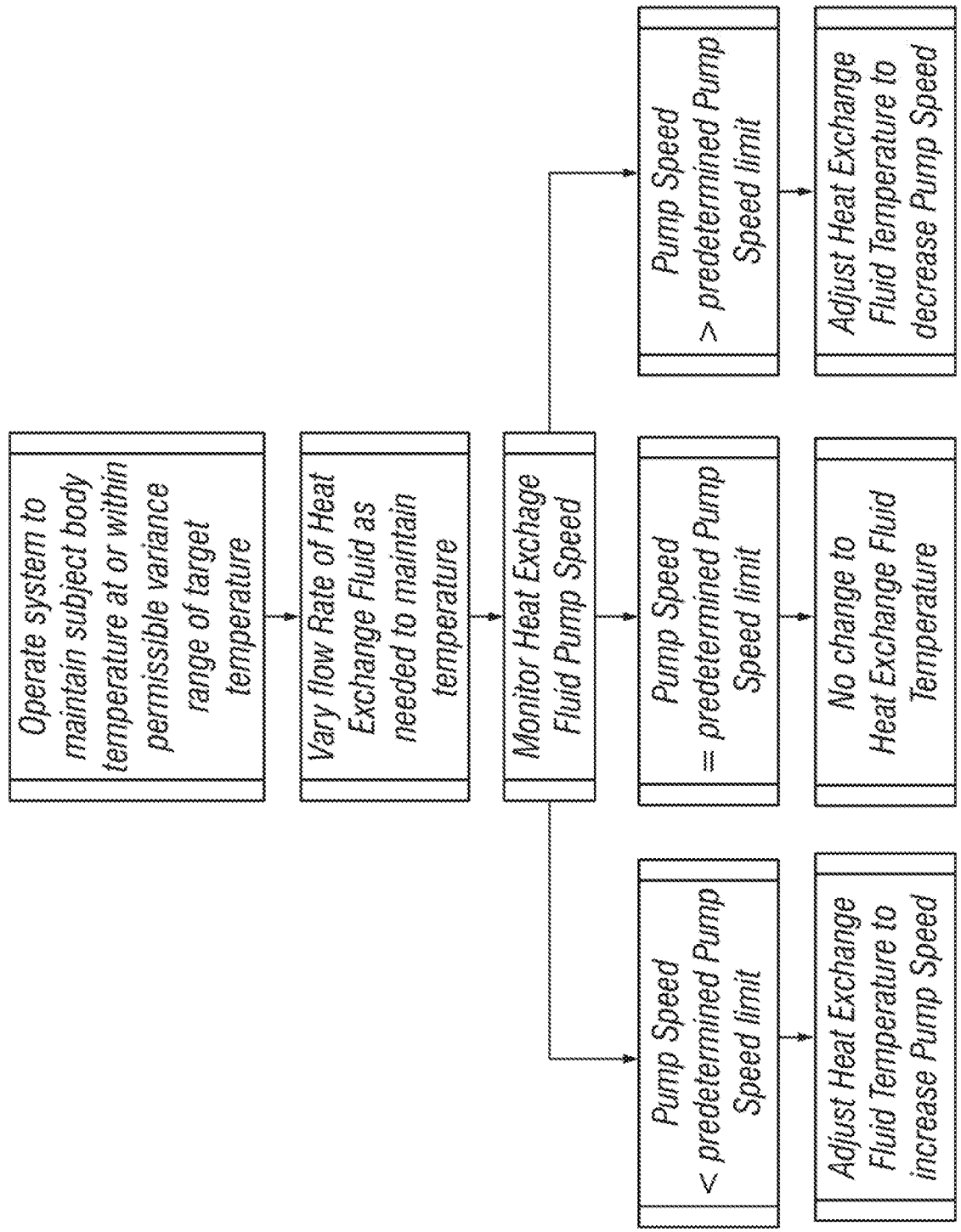

FIG. 35 is a flow diagram showing one example of a process by which a body heat exchange system may combine variations in heat exchange fluid flow rate with variations in heat exchange fluid temperature for precise maintenance of a target body temperature.

Figure 36:
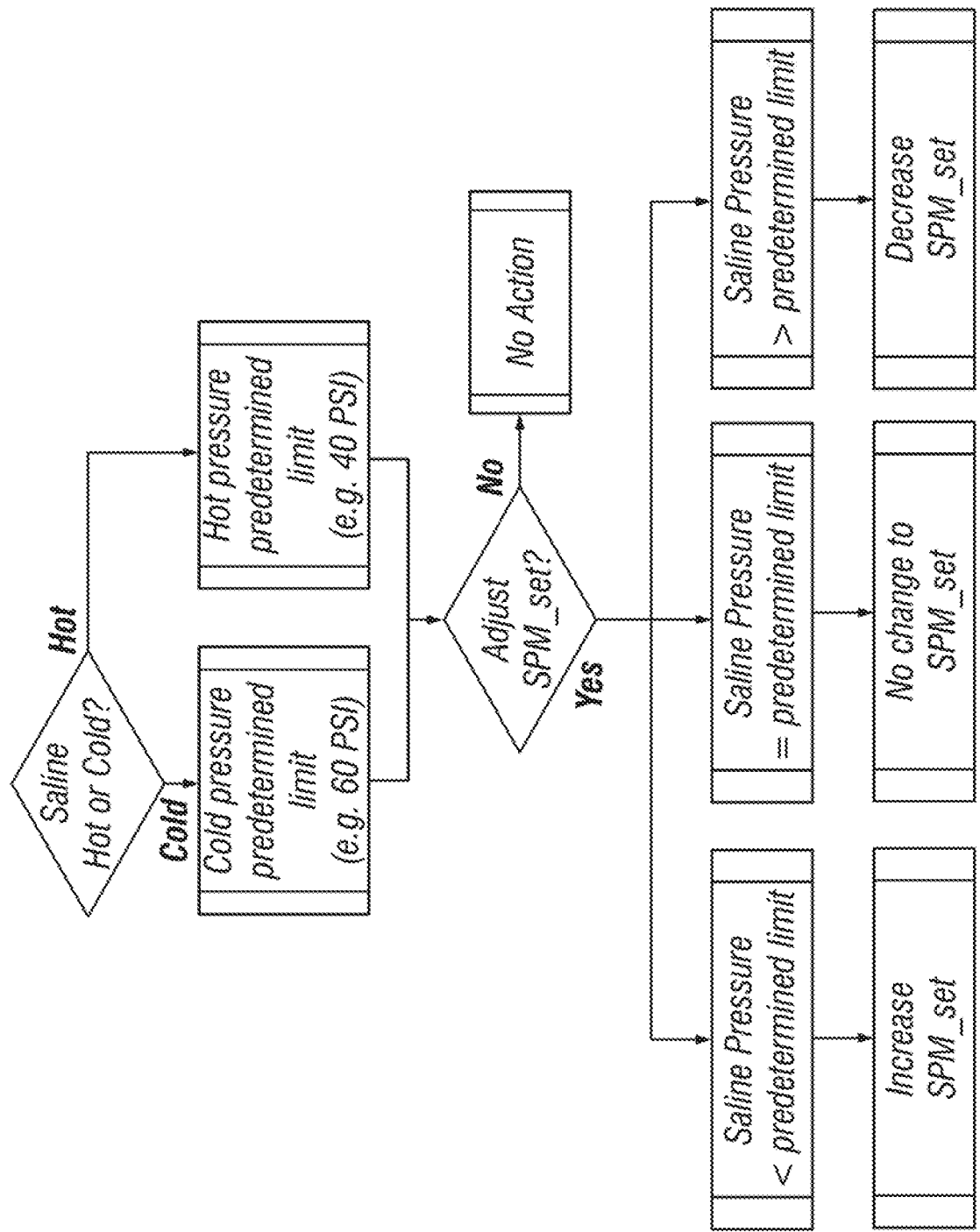

FIG. 36 is a flow diagram showing one example of a process by which a body heat exchange system may optimize pump speed and heat exchange fluid pressure during operation with either warm or cool heat exchange fluid.

FIG. 37 is a flow diagram showing one embodiment of a process for using a heat exchange catheter system to deter reperfusion injury in a subject who is suffering from an ischemic event that is treatable by a reperfusion procedure or administration of a reperfusion agent (e.g., thrombolytic drug).

Figure 38:
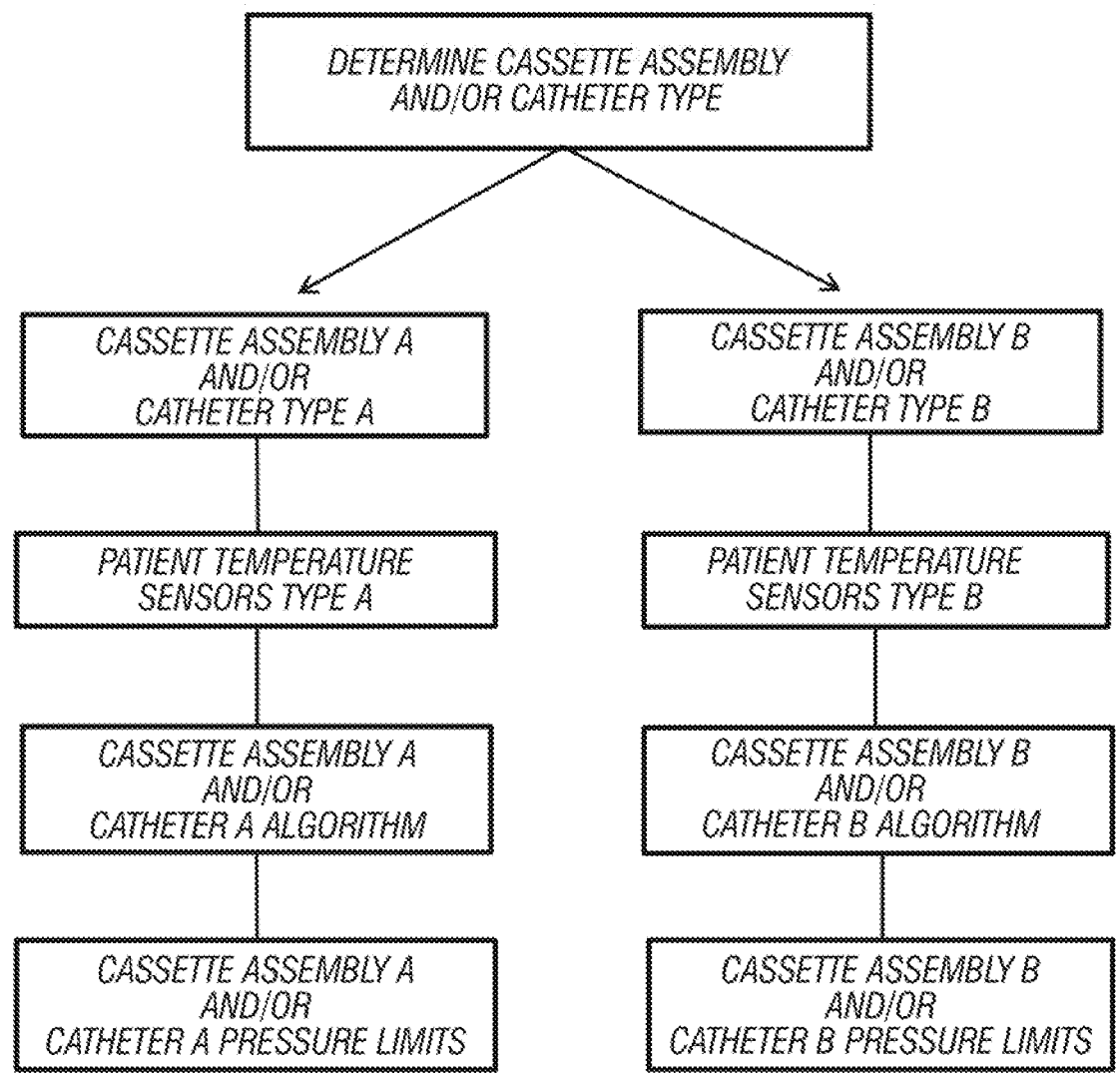

FIG. 38 is a flow diagram showing one example of a process by which a system that is configured and programmed to operate with more than one type of heat exchange device and/or body heat exchange device may detect the particular type of heat exchange device that has been connected to the system and adjust the system's operation in accordance with the detected type of heat exchange device and/or body heat exchange device.

Figure 3:
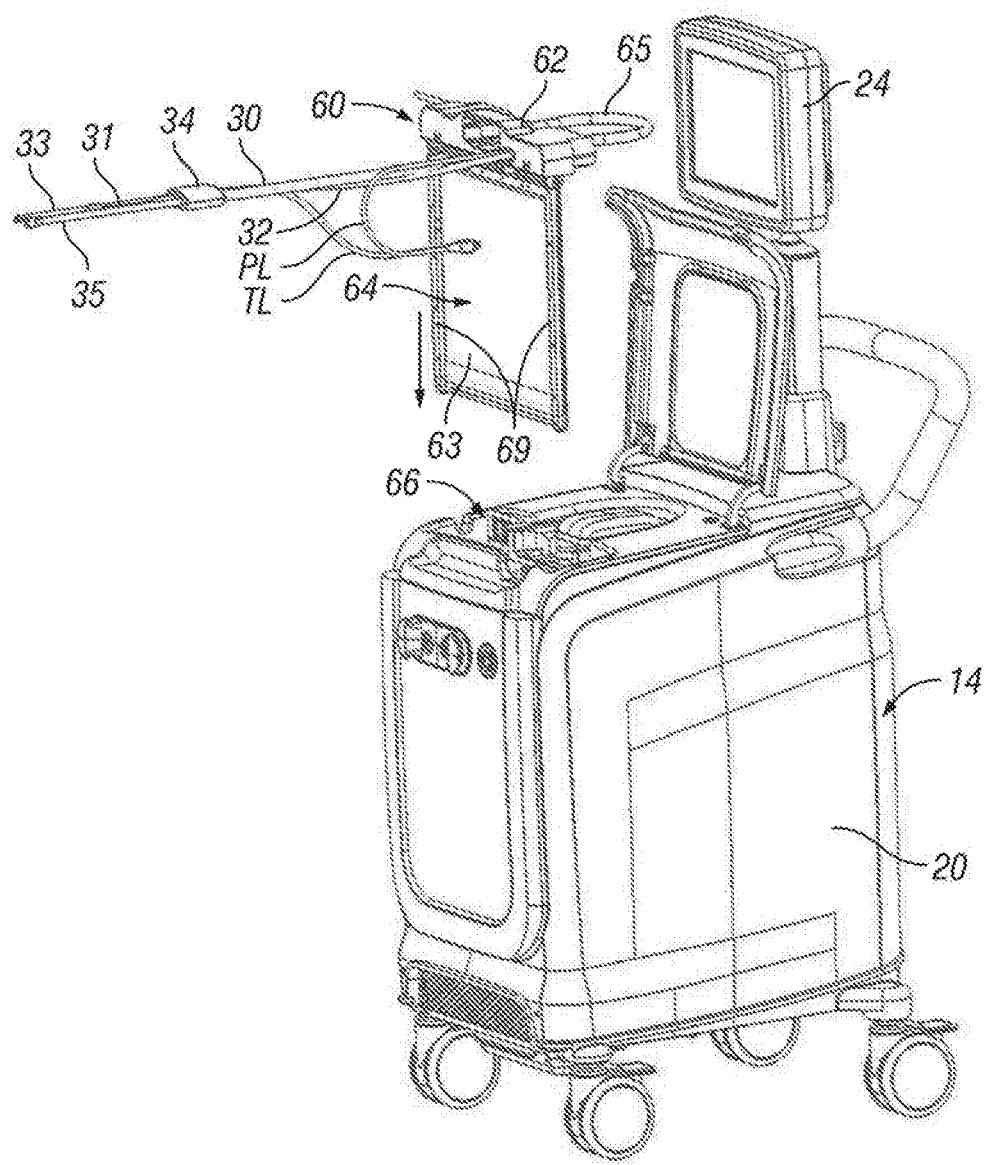
FIG. 3 is an exploded view of the control console with its access cover in an open position and the tubing/cassette/sensor module assembly staged for insertion in, and operative connection to, the control console.
Figure 39:
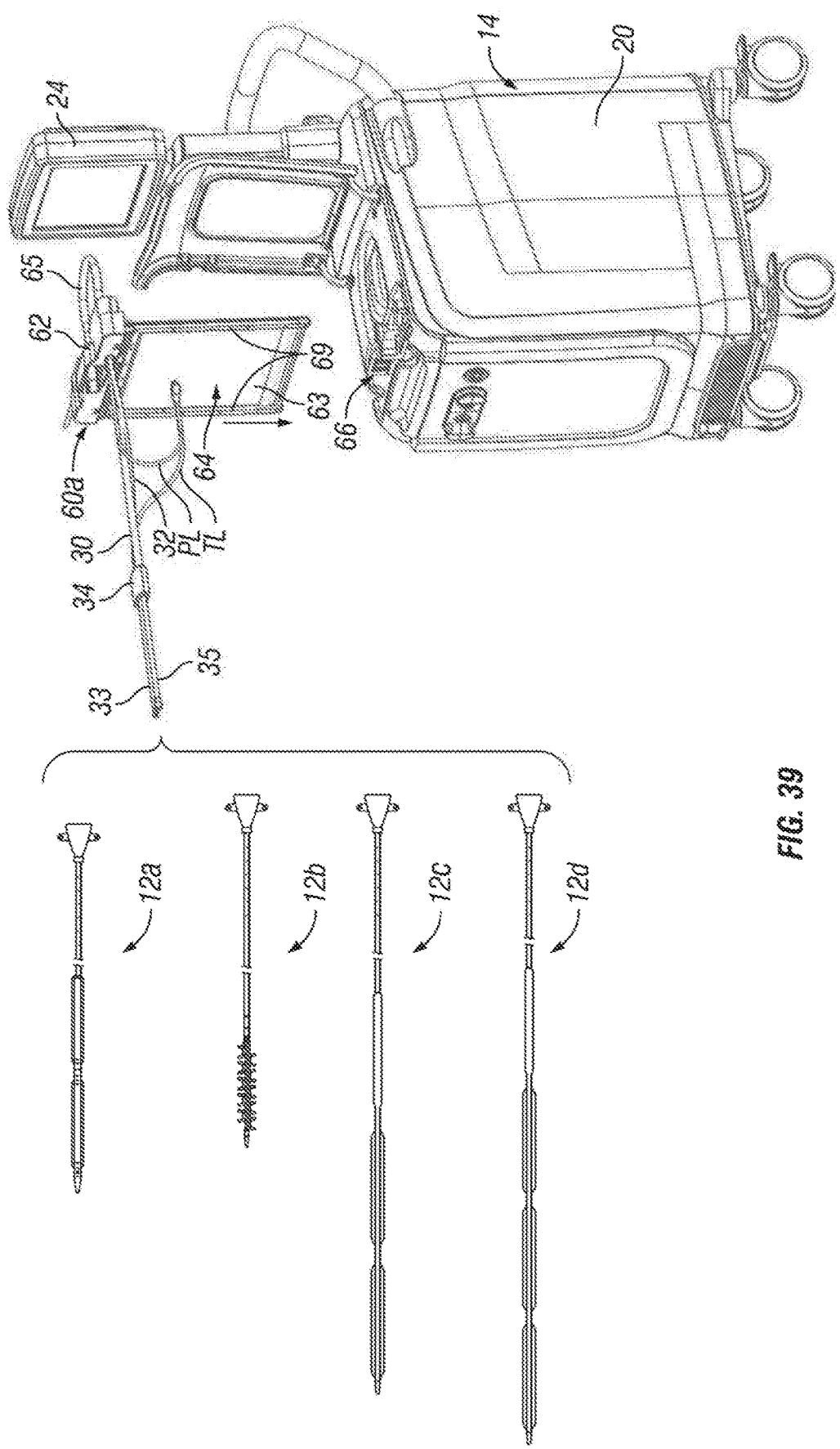

FIG. 39 shows the system of FIG. 3 in combination with partial views of a plurality of heat exchange catheters, any of which may be connected to and used in conjunction with the system.

Figure 40:
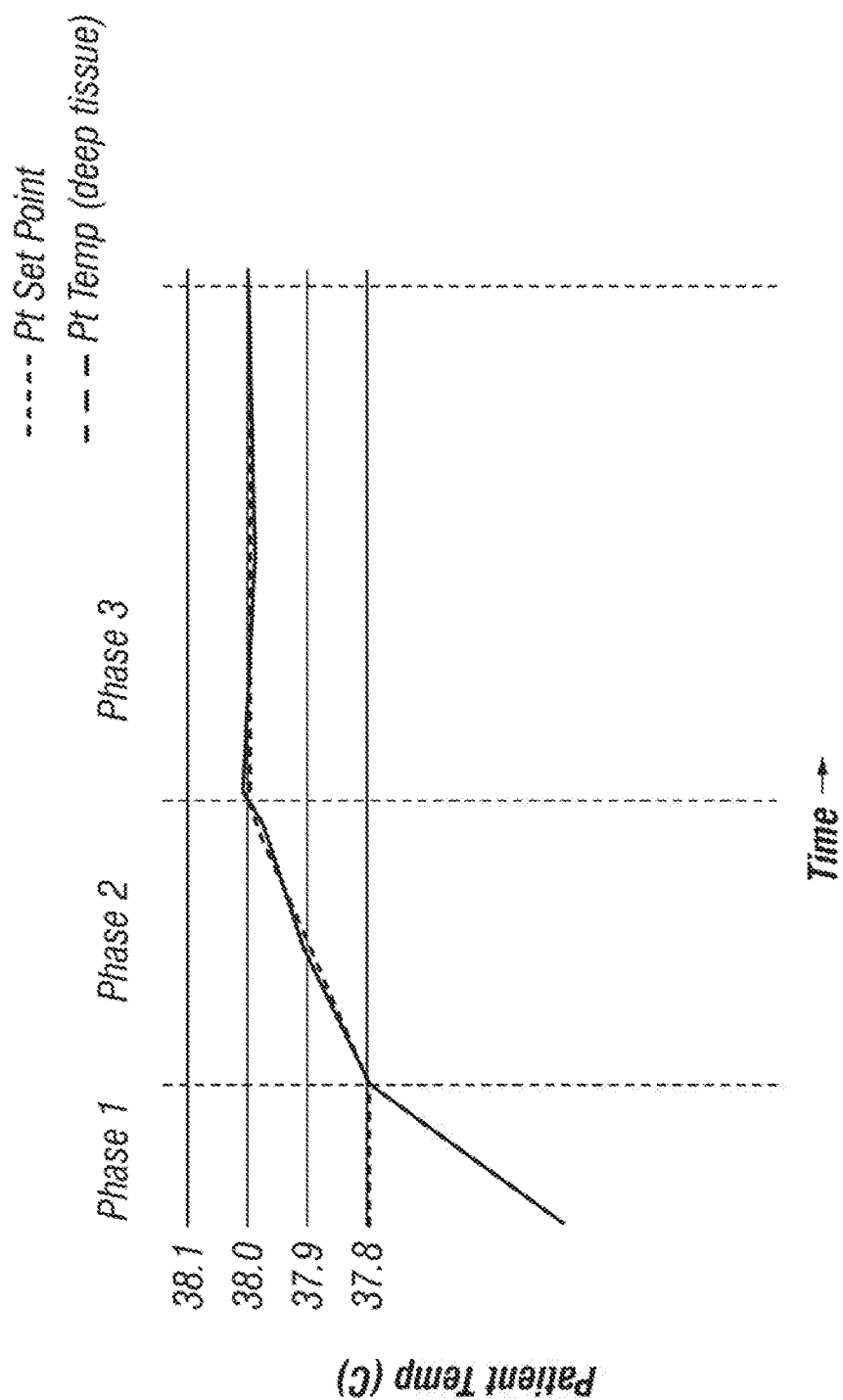

FIG. 40 is a graph of body temperature versus time during a body warming process using a body heat exchange system as described herein.

Figure 41:
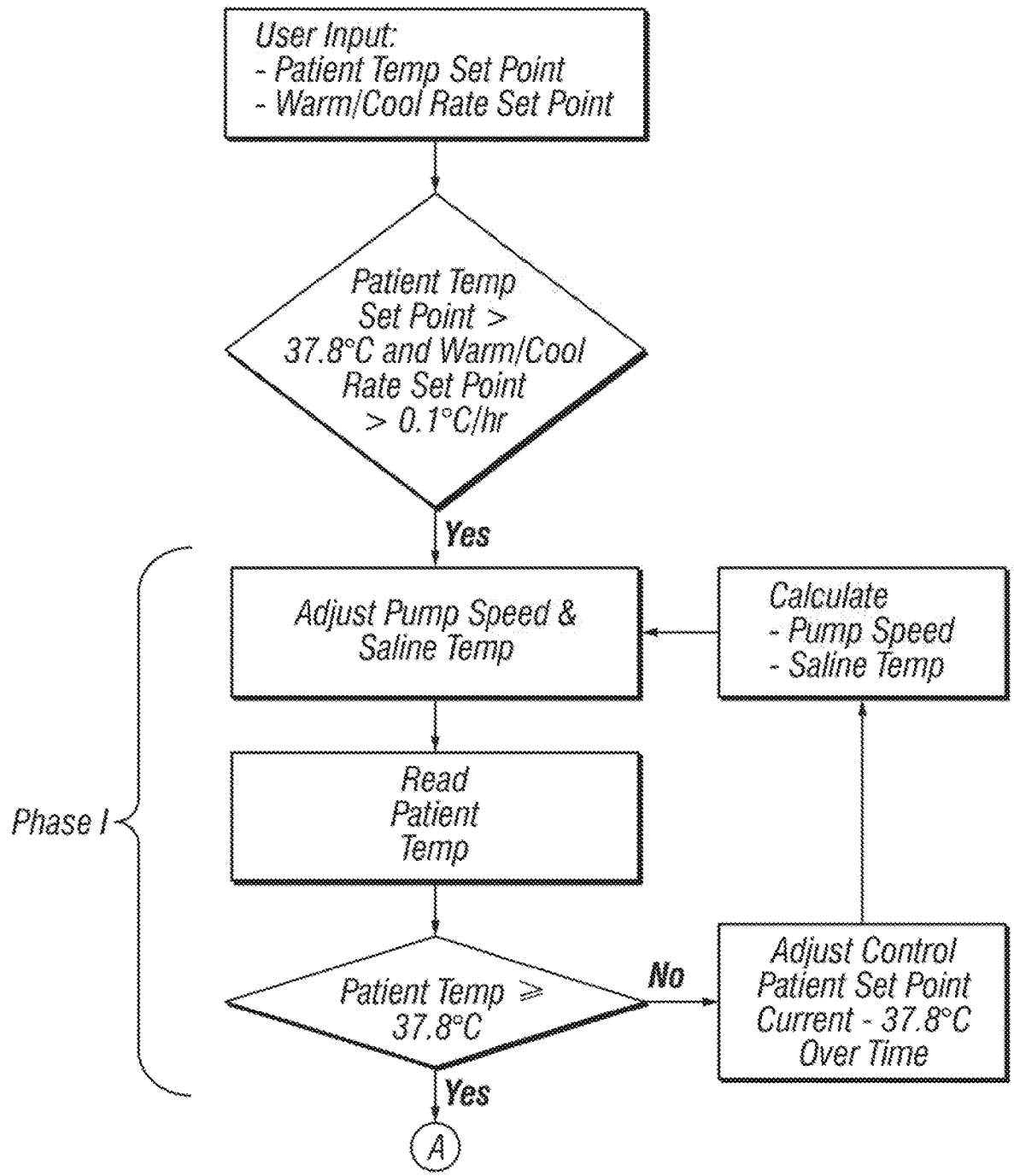
Figure 41:
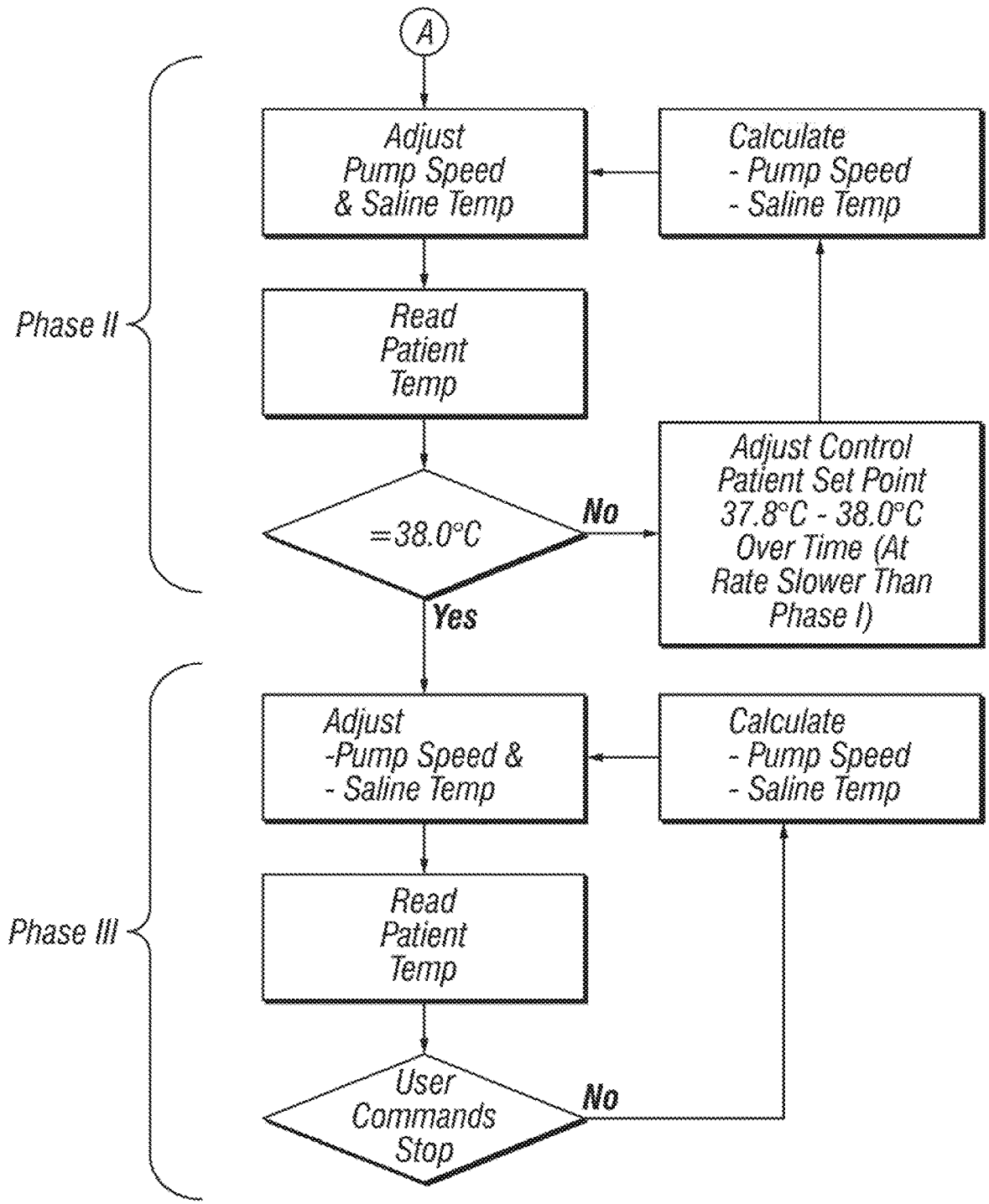

FIG. 41 is a flow diagram showing steps in one embodiment of a body warming process using a body heat exchange system as described herein.

DETAILED DESCRIPTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

FIG. 1 shows one embodiment of an endovascular heat exchange system 10 in operation to control the body temperature of a human subject. This endovascular heat exchange system 10 generally comprises an endovascular heat exchange catheter 12, an extracorporeal control console 14, a tubing/cassette/sensor module assembly 60 or cassette assembly which facilitates connection of the catheter 12 to the control console 14 and a temperature sensor TS. In at least some embodiments, the catheter 12, tubing/cassette/sensor module assembly 60 or cassette assembly and temperature sensor TS may be disposable items intended for a single use, while the control console 14 may be a non-disposable device intended for multiple uses.

In the embodiment shown, the endovascular heat exchange catheter 12 comprises an elongate catheter body 16 and a heat exchanger 18 positioned on a distal portion of the catheter body 16. Inflow and outflow lumens (not shown) are present within the catheter body 16 to facilitate circulation of a thermal exchange fluid (e.g., sterile 0.9% sodium chloride solution or other suitable thermal exchange fluid) through the heat exchanger 18. Optionally, the catheter shaft 16 may also include a working lumen (not shown) which extends through the catheter body 16 and terminates distally at an opening in the distal end of the catheter body 16. Such working lumen may serve as a guidewire lumen to facilitate insertion and position of the catheter 12 and/or may be used after insertion of the catheter 12 for delivery of fluids, medicaments or other devices. For example, as shown in FIG. 1, in some embodiments, the temperature sensor TS may be inserted through the catheter's working lumen and advanced out of the distal end opening to a location beyond the distal end of the catheter body 16. Alternatively, in other embodiments, the temperature sensor TS may be positioned at various other locations on or in the subject's body to sense the desired body temperature(s). Various heat exchange catheters may be used in the embodiments described herein.

With reference to FIGS. 32 through 33C, the elongate body 16 of the catheter 12 may comprise a proximal body 1300 and an assembly 1302 which comprises the heat exchanger 1304 attached to and/or extending distally from the proximal body 1300. As seen in the cross sectional view of FIG. 32B, in this particular embodiment, the proximal body 1300 has three lumens, an inflow lumen 1500*a*, an outflow lumen 1500*b* and an optional through lumen 1500*c*.

A hub 1700 is mounted on the proximal end PE of the proximal catheter body 1300. The hub 1700 has an inflow connector 30000 that is connected to the inflow lumen 1500*a* of the catheter body 1300 and an outflow connector 32000 that is connected to the outflow lumen 1500*b* of the proximal catheter body 1300. A through lumen port 2200 on the hub 1700 is connected to the through lumen 1500*c*.

The heat exchanger 1304 of this catheter embodiment comprises at least first and second coiled heat exchange tube segments 1307*a*, 1307*b*. In some embodiments, additional (e.g., third, fourth) heat exchange tube segments may be used. The heat exchange tube segments 1307*a*, 1307*b* may be formed of any suitable material. In the particular example shown, the heat exchange tube segments 1307*a*, 1307*b* may be advantageously formed of a noncompliant polymeric material, such as polyethylene terephthalate (PET), Pebax, Polyolefin, Polyurethane and/or Nylon, or other suitable compliant or noncompliant material and may be formed of a single tube or one or more tubes. In some embodiments the heat exchange tube segments 1307*a*, 1307*b* may expand and collapse depending on whether or not they are filled with fluid and, in such embodiments, the heat exchange tube segments 1307*a*, 1307*b* may be referred to a "balloons." For some applications, the heat exchange tube segments 130*fa*, 1307*b* may have outer diameters in the range of 2 mm-19 mm and wall thicknesses in the range of 0.0127 mm-0.1 mm.

In this example, the proximal end of the first tube segment 1307*a* is connected to the inflow lumen 1500*a* and the proximal end of the second tube 1307*b* segment is connected to the outflow lumen 1500*b*. The distal ends of the first and second tube segment 1307*a*, 1307*b* are directly or indirectly in fluidic connection with each other such that heat exchanger fluid that has flowed in the distal direction through the first tube segment 1307*a* will then return in the proximal direction through the second tube segment 1307*b*. The distal ends of the heat exchange tube segment 1307*a*, 1307*b* are connected to the inflow and outflow connectors 30000, 32000 of the catheter 12.

As seen in detail in FIGS. 33A-33C, the heat exchange assembly 1302 may comprise a spine or elongate member 4000 and at least one heat exchange member 1307 disposed on the spine or elongate member 4000. The heat exchange assembly 1302 is attached to and extends distally from the proximal body 1300, as shown. An introducer sheath may be used to introduce the catheter into a patient's body. Alternatively, the catheter may be introduced without using an introducer sheath.

The term "elongate member," may mean, in at least some embodiments, a member, e.g., a spine or similar structure, which extends from a catheter body and upon which at least one heat exchange member is disposed. In at least some embodiments, the elongate member 4000 is distinguishable from the proximal body 1302 on the basis of one or more differences in structure or physical property. In the particular embodiment shown, the elongate member 4000 comprises an elongate, generally C-shaped member having receiving features 4600 which comprise spaced-apart transverse notches, recesses or grooves formed along the open side of the generally C-shaped member. The heat exchange member(s) 1307 may be inserted in these recessed, groove, or notch-type receiving features 4600 such that the helical loops extend around the closed side of the generally C-shaped elongate member 4000. The heat exchange member(s) 1307 may be secured to the receiving features 4600 by adhesive or other suitable means.

Non-limiting examples of other heat exchange catheters and related apparatus that may be used are described in U.S. Pat. No. 9,492,633, and United States Patent Application Publications Nos. 2013/0090708, 2013/0178923, 2013/0079855, 2013/0079856, 2014/0094880, 2014/0094882, 2014/0094883, and unpublished, copending U.S. patent application Ser. Nos. 15/395,858, 15/395,923 and 15/412,390, the entire disclosure of each such patent and application being expressly incorporated herein by reference. Other examples of catheters that may be used in this invention include those commercially available from ZOLL Circulation, Inc., San Jose, Calif., such as the Cool Line® Catheter, Icy®️ Catheter, Quattro® Catheter: Solex 7® Catheter, InnerCool® RTx Accutrol Catheter and the InnerCool RTx Standard Catheter. Additionally incorporated herein by reference is the entire disclosure of U.S. patent application Ser. No. 15/594,539 entitled Advanced Systems and Methods for Patient Body Temperature Control, filed on May 12, 2017.

The extracorporeal control console 14 generally comprises a main housing 20 and a console head 24. As described in detail herebelow, the main housing 20 contains various apparatus and circuitry for warming/cooling thermal exchange fluid to controlled temperature(s) and for pumping such warmed or cooled thermal exchange fluid through the catheter 18 to effectively modify and/or control the subject's body temperature. The console head 24 comprises a display device or user interface, such as a touch screen system, whereby certain information may be input by, and certain information may be displayed to, users of the system 10. On the housing 20 there are provided a first connection port 40 for connection of a temperature sensor TS that is inserted through the heat exchange catheter 12 as shown in FIG. 1 as well as other connection ports 36, 38 for connection of additional or alternative types of temperature sensors and/or other apparatus.

Figure 4:
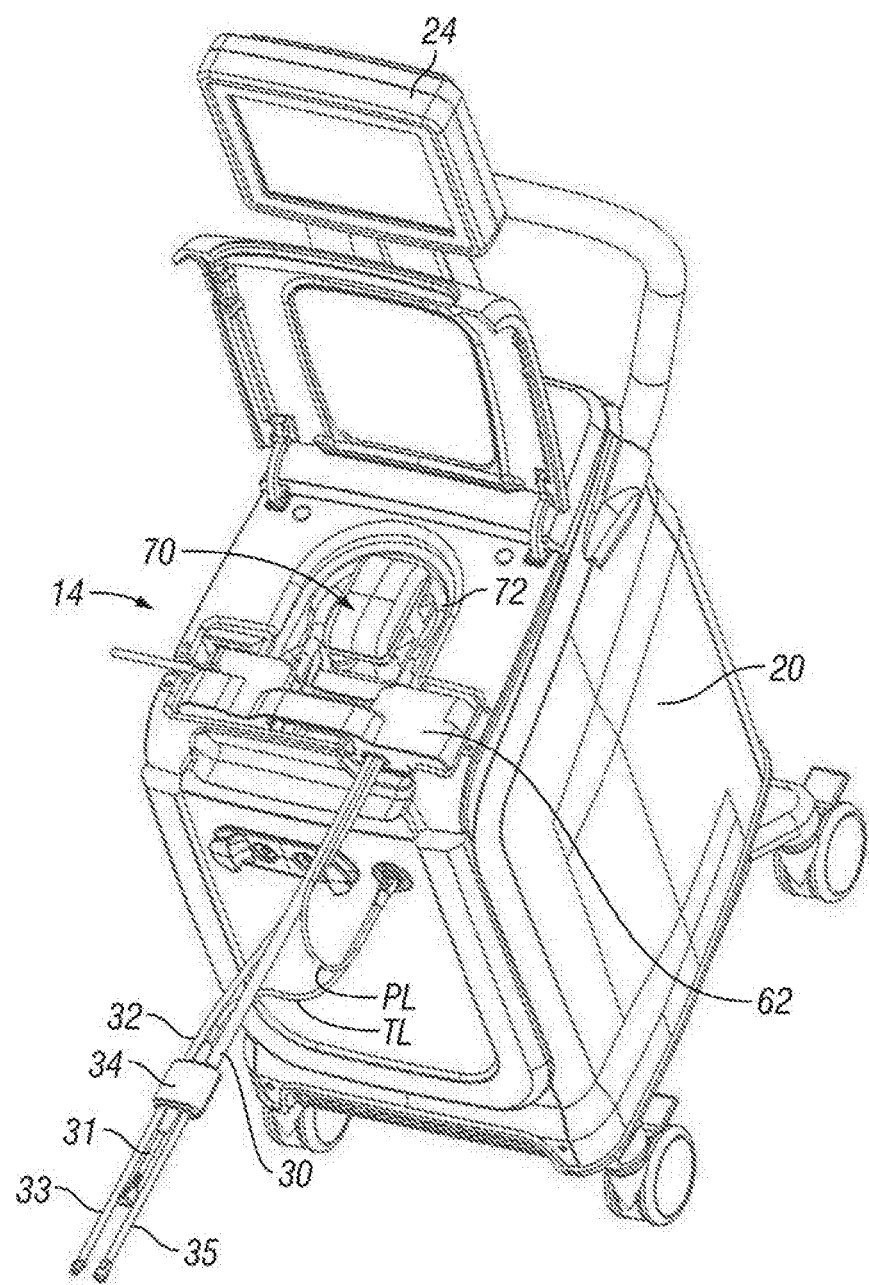
FIG. 4 is a top (perspective) view of the control console with its access cover in an open position and the tubing/cassette/sensor module assembly operatively inserted in and connected to the control console.
Figure 5:
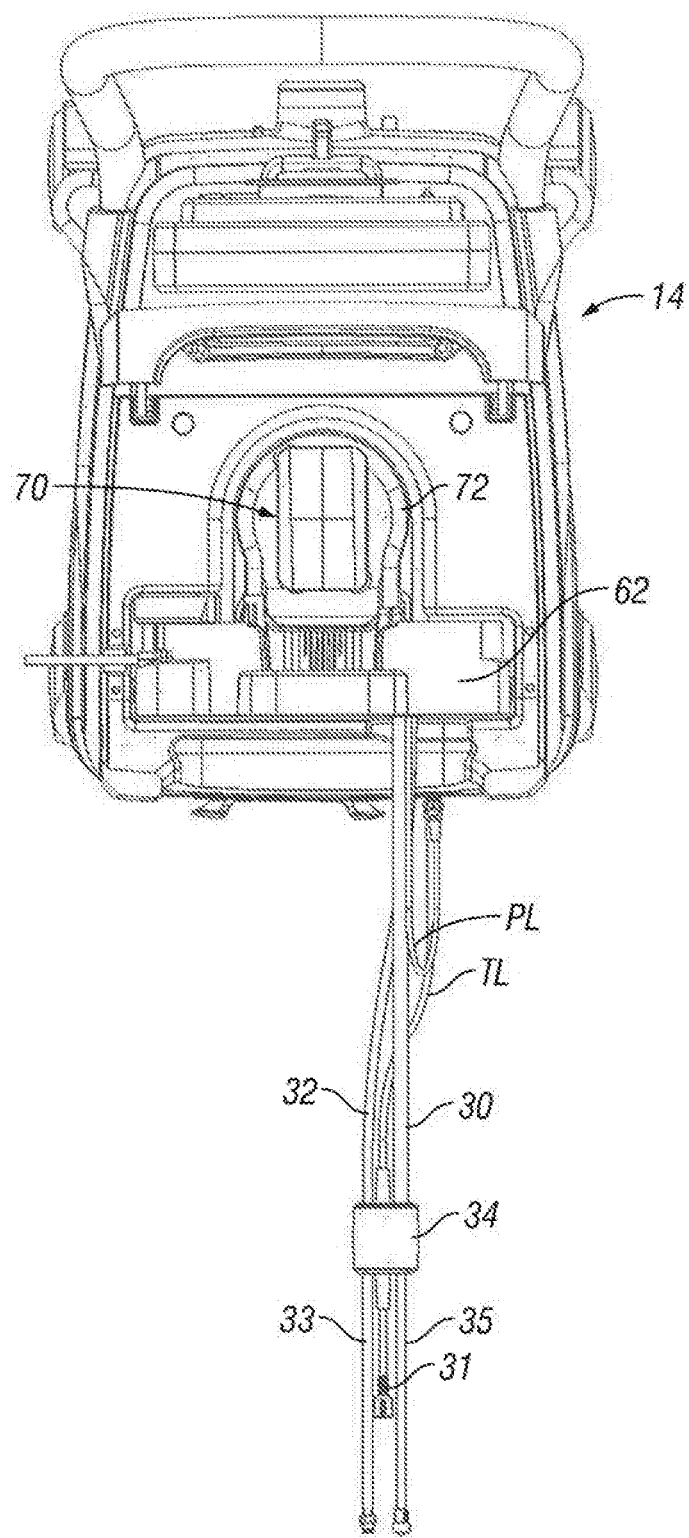
FIG. 5 is a top (plan) view of the control console with its access cover in an open position and the tubing/cassette/ sensor module assembly operatively inserted in and connected to the control console.

The tubing/cassette/sensor module assembly 60 or cassette assembly, which is seen in further detail in FIGS. 3-5, generally comprises a sensor module 34, an inflow conduit 32, inflow connector 33, outflow conduit 30, outflow connector 35, temperature lead TL, temperature lead connector 31, pressure lead PL, cassette 64, cassette housing 62 and peristaltic pump tubing 65. In certain embodiments, the pump tubing may be made of materials suitable for continuous or intermittent use over a desired period of time, e.g., suitable for use over a period of time from 20 minutes to 12 hours or 1 hour to 7 days or longer. Nonlimiting examples of such material include Elastollan® and Norprene® and other similar materials.

Figure 2A:
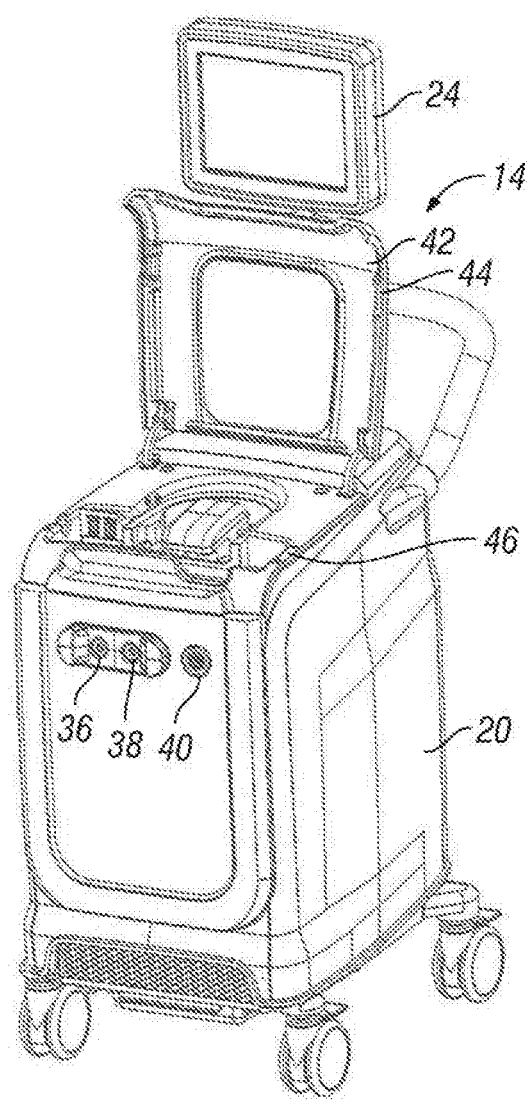
FIG. 2A is a left/front perspective view of the control console with its access cover in an open position.
Figure 2B:
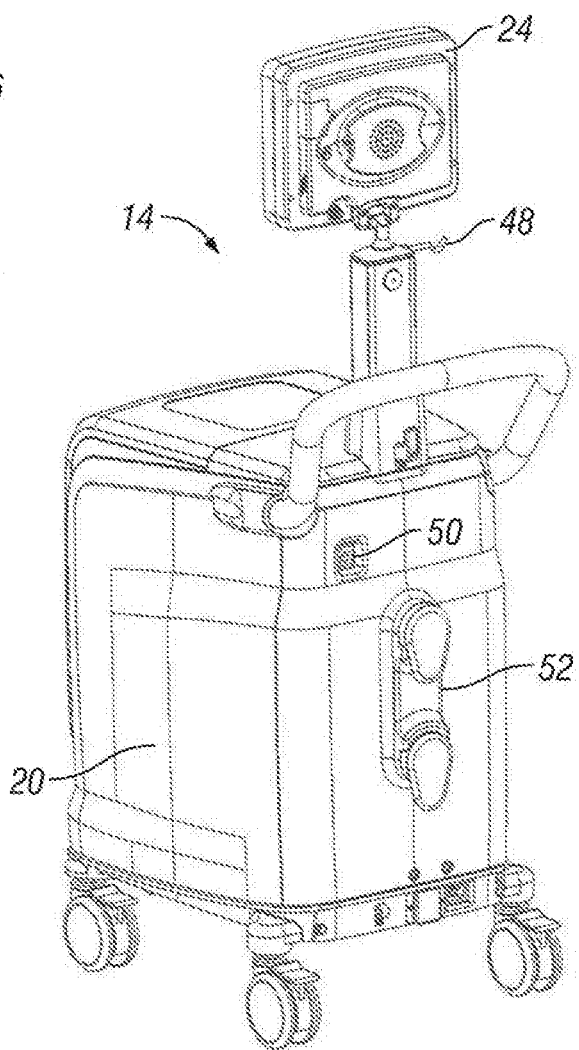
FIG. 2B is a left/rear perspective view of the control console.

FIGS. 2A through 9 show further detail of the components within the housing 20 and the manner in which the tubing/cassette/sensor module assembly 60 or cassette assembly is inserted in and connected to the control console 14. As seen in FIGS. 2A through 3, the control console 14 has an openable/closable access cover 42 which, when opened, permits insertion of the cassette 64 into a cassette receiving space 66 as well as other connection of the tubing/cassette/sensor module assembly 60 or cassette assembly to other components of the system described below. A magnet 44 on the access cover 42 interacts with a magnetic sensor 46 to emit signal(s) indicating whether the access cover 42 is opened or closed. Other sensors and detection mechanisms known to persons having skill in the art may be utilized as well. The system controller located in the housing 20 may be programmed to halt running of certain components of the system when the access cover 44 is opened. On the rear of the housing 20, there is provided a power switch 50 and a power cord holder 52. A bracket 48 is provided on an upstanding portion of the housing which supports the console head 24 for hanging a bag or container of fluid.

As seen in FIGS. 3 through 5, with the access cover 42 in an open position, the cassette 64 is insertable downwardly into the cassette receiving space 66 and the pump tubing 65 is insertable into a tubing raceway 72 of pump 70.

FIGS. 6 through 10 provide partially disassembled and sectional views which reveal various components of the control console 14. The thermal exchange engine 108, includes a refrigeration system which comprises a compressor 92, stepper motor for turning an expansion valve 106, fans 96 and 104, condenser 98 and compressor heat sink 100. The heat sink may be a metallic, e.g., aluminum, cylindrical enclosure that surrounds the compressor. The heat sink is in contact with the compressor and increases the surface area of the compressor to facilitate enhances removal of heat from the compressor. The thermal exchange system is powered by power supply 94. Thermal exchange plates 80, are provided to alternately warm or cool thermal exchange fluid as it circulates through a cassette 64 that has been inserted in the cassette receiving space 66 between the thermal exchange plates. Resistance heaters 82 are mounted on the plates 80 for warming the plates 80 when operating in a warming mode and a refrigerant, such as Refrigerant R143a (1,1,1,2 Tetrafluoroethane) is compressed by the compressor 92 and circulated through the condenser 98 and plates 80 to cool the plates when operating in a cooling mode. In certain embodiments, heaters may include a thermal cutout switch for automatically turning one or more of the heaters off if the heaters were to overheat.

When operating in a cooling mode, the thermal exchange engine 108 emits heat. Fans 96 and 104 circulate air through air plenums or spaces adjacent to the thermal exchange engine 108 and over surfaces of the compressor and compressor heat sink 100 to exhaust emitted heat and maintain the thermal exchange engine 108 at a suitable operating temperature. Specifically, in the embodiment shown, air enters air intake 84 through filter 90, circulates through the device as indicated by arrows on FIGS. 7 and 8, and is exhausted through an air outlet or exhaust vent on a side of the console 14 as shown specifically in FIG. 8. The airflow pathway is specifically configured to minimize the amount of sound that escapes from the system via the airflow pathway and is audible to a user or patient. The airflow pathway includes a convoluted pathway or channels which provide reflective surfaces to contain the acoustic energy within the cooling engine enclosure. Also, the interior of the intake and exhaust ducts and pathway or channels are lined with an acoustically absorbent material, e.g., open-celled elastomeric foam. The combination of these features minimizes the amount of sound, such as that generated by the fans and compressor, that escapes the system. For example, in certain embodiments, the operating noise level of a system may not exceed 65 dBA measured at a distance of 1 m from the system when the system is in maximum cooling and 58 dBA measured at a distance of 1 m from the system when the system is in maintenance or warming.

The structure and function of the thermal exchange plates may be appreciated in further detail in FIGS. 11 through 17. Thermal exchange plates 80 may be positioned on either side of the cassette receiving space 66. The thermal exchange plates are connected on their ends forming a cassette receiving space or slot between the plates. The thermal exchange plates may be referred to as a thermal exchange plate assembly. Resistance heaters 82 are mounted in one or more of plates 80 and are useable to warm the plates 80 when warming of the circulating thermal exchange fluid is desired. In certain embodiments, vertically oriented, serpentine or convoluted, refrigerant flow channels 120 are formed within the plates 80. This orientation and design of the refrigerant flow channels help maximize and realize the cooling power of the cooling engine, For example, the plates are configured to evaporate the refrigerant moved by a 900 W compressor (e.g., a Masterflux compressor) within a cooling engine envelope sized to fit within the housing 20, as illustrated in the figures herein. In each plate, cold refrigerant circulates through refrigerant inlet 112, through the refrigerant flow channels 120 and out of refrigerant outlet 114. The refrigerant changes phase from a liquid substantially to a gas while flowing through the refrigerant flow channels 120, thereby cooling the plates 80. Such warming or cooling of the plates 80, in turn causes warming or cooling of thermal exchange fluid being circulated through a cassette positioned within the cassette receiving space 66. Temperature sensors 110, e.g., thermistors, may be located on the plates to detect the temperature of the plates. Signals from the temperature sensors may be fed back to the system controller or control processor to control warming and/or cooling (e.g., to prevent freezing) by the system.

Optionally, as shown in the views of FIGS. 15 and 16, the thermal exchange plates 80 may incorporate channels 125 for circulation of a thermal exchange fluid directly through the plates. For example, a desired thermal exchange fluid may circulate in inlet 122, through horizontal flow channels 125 and out of outlet 124. A single inlet port may be used to supply thermal exchange fluid to both plates as the fluid passes from a first plate to the second plate, through channels located at the ends of the thermal exchange plate assembly, and exits the thermal exchange plate assembly through a single outlet port. A drain port 127 may be provided for draining residual thermal exchange fluid or flushing debris from the flow channels 125, when required.

These channels 125 may be used for cooling or warming a secondary thermal exchange fluid simultaneously with, or as an alternative to, the warming or cooling of a heat exchange fluid circulating through a cassette 64 inserted within the cassette receiving space 66. In some embodiments, the channels 125 may be configured to provide a volume flow of secondary thermal exchange fluid that differs from the volume flow of thermal exchange fluid which circulates through the cassette 64. For example, a cassette 64 may be inserted in the cassette receiving space 66 and used for circulating a relatively small volume of warmed or cooled thermal exchange fluid (e.g., sterile saline solution) through an endovascular catheter 12 and, simultaneously or alternately, the channels 125 may be used to warm or cool a larger volume of a secondary thermal exchange fluid (e.g., nonsterile water) for circulation through body surface cooling device(s) such as surface cooling pad(s), blanket(s), garment(s), etc. Further details and examples of such concurrent or separate use of endovascular and body surface temperature exchange are described in copending U.S. patent application Ser. No. 15/412,390 entitled Managing Patient Body Temperature Using Endovascular Heat Exchange in Combination With Body Surface Heat Exchange, the entire disclosure of which is expressly incorporated herein by reference.

A schematic diagram of an embodiment of a thermal exchange engine or refrigeration loop useable in the systems described herein is shown in FIG. 18. This embodiment has a high side HS and a low side LS. The components shown in this diagram include superheat temperature sensor 130, thermal exchange plate evaporators 132, electric heaters 134, an electronic expansion valve, compressor 140, counterflow heat exchanger 142, filter/drier sight glass 138, and electronic expansion valve 144. In the normal operational state of the cooling engine, the hot gas bypass valve 136 is closed, the compressor 140 is running, and refrigerant flows through the system as follows. First, refrigerant exits the compressor in the gaseous phase at high pressure (typically 8-14 bar) and high temperature (typically 100 to 130 degrees F.) and enters the condenser. In the condenser, heat is transferred from the refrigerant, causing it to condense into it's liquid phase and cool further (typically to 75-95 degrees F.). Liquid refrigerant then passes through the filter dryer 138 which filters the liquid for particulate and absorbs any water contained in the liquid. From there, liquid refrigerant passes the sight glass "S" which allows an observer (e.g. service person) to confirm the refrigerant is in the liquid phase. Liquid refrigerant then passes through the primary channel of the counterflow heat exchanger 142, which causes it to cool further (typically to 40-75 degrees F.) due to heat transfer with the secondary channel of the counterflow heat exchanger. From there, liquid refrigerant passes through the expansion valve 144, which acts as a restriction on the system. After passing through the expansion valve, refrigerant is suddenly at low pressure (typically 2-4 bar) and as a result drops in temperature (to typically 25-35 degrees F.) and partially enters the gaseous phase. Cold, low-pressure, liquid refrigerant then enters the heat exchange plates 132. Heat is added to the refrigerant from the following sources: from the thermal mass of the plates, from saline passing through the cassette heat exchanger, or from water passing through the liquid channels within the cold plates, all of which cause the refrigerant to mostly or entirely enter the gas phase. From the heat exchange plates 132, low-pressure refrigerant flows into the secondary channel of the counterflow heat exchanger where it transfers heat from the refrigerant contained in the primary channel, causing it to warm (to typically 35 to 70 degrees F.). Refrigerant at this point may be mostly or entirely in the gas phase, and then enters the compressor 140, thus completing the circuit. A secondary operational state exists for the cooling engine, where the HGBP valve 136 is open. In this state, hot, gaseous refrigerant exits the compressor and directly enters the heat exchange plates, causing them to warm up rapidly. This secondary state is used when it is desirable to slow down the cooling provided to the patient, or to warm the patient, without turning off the compressor. Alternatively, the compressor can be shut off, however use of the HGBP valve 136 has the advantage of being able to be opened and closed rapidly and repeatedly as necessary to maintain the desired heat exchange plate temperature. One embodiment of a pump 70 (e.g., a peristaltic pump) and associated assembly is shown in FIGS. 19 through 23. The pump 70 comprises a rotor assembly 160 and cover 161 connected to a drive motor 170 which causes the rotor assembly to rotate. The rotor assembly includes guide rollers 164a and 164b, and drive rollers 166a and 166b. As the rotor assembly rotates, during pump operation, the drive rollers apply pressure to the pump tubing (not shown), which is positioned in the pump raceway, thereby causing thermal exchange fluid to move through the pump tubing. The pump raceway is designed with a low height (i.e. as measured along the axes of the rollers) in order to allow the pump to be smaller, lighter weight, and lower cost. However with this low height it is critical to keep the pump tubing aligned with the raceway, in order to avoid jamming of the tubing within the pump assembly (leading to wear of the pump and wear or rupture of the tubing), and to avoid the tubing partially or entirely coming out of contact with the drive rollers and thereby not generating some or all of the pressure needed to pump heat exchange fluid through the catheter. As seen in FIG. 20A, each guide roller 164a, 164b has a tapered (e.g., barrel shaped) side wall 165. The guide roller may include a central section which is not tapered (i.e. parallel to the axis of rotation) 167. The tapered or barrel shape of the guide roller facilitates self-centering of the pump tubing on the guide roller, to ensure that the pump continues to perform as intended. Because the tubing is being stretched over the guide rollers, a normal force is generated, which in turn creates a frictional force. The taper on the rollers is at a shallow angle (e.g., of a range of 5 to 25 degrees) so that the frictional force is sufficient to prevent the tubing from sliding on the roller surface. Given that the tubing does not slide, the taper or barrel shape puts a higher tensile load on the pump tubing at the center of the roller (i.e. at the widest part of the barrel or roller), and a lower tensile load on the pump tubing at either the top or bottom edges of the roller (i.e. the narrowest part of the barrel or roller). This difference in tensile forces leads to the self-centering effect by developing a net force acting on the tubing along the axis of the roller, in the direction of the center of the roller. A front portion of the pump 70 is mounted on a front plate 172. Optical sensors 174, for detecting when a cassette 64 and its cassette housing 62 are in place and properly positioned for operation, may also be located on the front plate 172. Hooks 176a, 176b extend through slots in the front plate 172. These hooks 176a, 176b are positionable in retracted positions which allow installation of the cassette 64 and insertion of the pump tubing 65 in the pump raceway 162. Thereafter, these hooks 176a and 176b are movable to advanced positions wherein they exert a force on the cassette housing 62 at two separate points of contact thereby deterring unwanted movement of the cassette 64, cassette housing 62 or attached pump tubing 65, and securing the cassette in position for system operation. Also mounted on the front plate 172 are level sensors for sensing fluid levels within a reservoir formed within the cassette housing 62. The pump 70 is alternately disposable in an operative configuration (FIG. 22) and a loading configuration (FIG. 23). Translational motor 180 causes the hooks to move between a retracted and advanced position, and causes the pump to move between an operative and loading configuration or position.

Priming of the system, when the cassette 64 is positioned in the cassette receiving space 66 between thermal exchange plates 80, may be performed quickly by using one or more pump direction changes. The pump 70 may be switched back and forth between running in reverse and running in a forward direction for various durations of time, at various speeds. The first pump reversal creates a vacuum and the subsequent reversals help remove bubbles from the system/ line.

To purge the thermal exchange fluid from the system the pump 70 may be run in reverse. In one example, the pump 70 may be run in reverse at 60% of max pump speed for about 20 seconds, during which the return line or vessel outlet line is closed to prevent the cassette vessel/bag from refilling with thermal exchange fluid or saline when the pump is reversed or opened. A check valve may be utilized, which may be positioned in the cassette housing, e.g., in the vessel outlet tubing, between the tubing and the reservoir, to prevent the vessel/bag from refilling with thermal exchange fluid or saline when the pump is reversed or open. For example, in some embodiments, the check valve may be integrated into the inflow connector 206 seen in FIG. 28 to prevent fluid from back-flowing into the vessel/bag 63 when the pump is reversed or open.

FIGS. 24 through 28 show further details of the tubing/ cassette/sensor module assembly 60 or cassette assembly. The cassette housing 62 is attached to a frame 69 which supports the side edges of the expandable vessel or bag 63. In certain embodiments, the vessel or bag may include one or more sides having a thickness suitable to prevent tears during use or manufacture. For example, the thickness may be 0.001 inches-0.005 inches. In certain embodiments the thickness may be about 0.002 inches. A lower edge 63a of the expandable vessel or bag is sealed and may include a support. As seen in FIG. 28, the cassette housing (bottom cover removed) 62 encloses a reservoir 207, pressure sensor 202, outflow connector 204 which is connected to the pulse-damping outflow conduit 30, inflow connector 206 which is connected to return or inflow conduit 32. During system operation, thermal exchange fluid returns from the catheter, flowing through inflow conduit 32, through inflow connector 206, through vessel inlet tubing, into the expandable vessel or bag 63, through the expandable vessel or bag 63 from one side to the other as indicated by arrows on FIG. 28, exchanging heat with refrigerant flowing through the thermal exchange plates, then out of the vessel through vessel outlet tubing, into reservoir 207, through pump tubing 65, through outflow connector 204, through pulse-damping outflow conduit 30 and back to the catheter. Refrigerant flows through the refrigerant flow channels in the thermal exchange plates in a first direction, while thermal exchange fluid flows though the expandable vessel in a second direction that is substantially opposite the first direction. This counter flow of refrigerant and thermal exchange fluid helps maximize heat exchange between the two fluids.

To minimize the force required to insert or remove the Heat Exchange (Hx) Bag or vessel from the Cold Plates, several methods are described below.

The frictional force between the Cold Plates and the Hx Bag may be reduced by adding coating to the surface of the Cold Plates that lowers its coefficient of friction. Possible coatings include Teflon or similar. The surface of the Cold Plates may be polished. A coating may be added to the surface of the Hx Bag that lowers its coefficient of friction, e.g., materials that may be used include silicone, or similar (these can be brushed, sprayed, dipped, etc.)

In some embodiments, a layer (release layer or antifriction layer) of material may be placed over the outside surface of the Hx Bag which lowers its coefficient of friction. Possible materials include paralyene, HDPE (Triton), ePTFE, PTFE, FEP or similar. A low friction sheet made of these materials may be used. In certain embodiments, a fluoropolymer may be placed on the cold plates and use a urethane HX bag with HDPE release layer on the bag. The HX bag may include an HDPE release layer on each side of the bag with each layer and the urethane bag affixed to the cassette frame h pegs or clamps. Alternatively, a single longer piece of HDPE release layer may be folded around the HX bag and then the hag and release layers are affixed to the cassette frame with pegs or clamps The pulse-damping outflow conduit 30 functions not only as a conduit through which the thermal exchange fluid flows but also a pulse damper for damping pulses in the thermal exchange fluid as it flows through the outflow conduit, to a catheter. Pulses may arise due to the nature of the pump used for the thermal exchange fluid. For example, in the case of a peristaltic pump with two drive rollers, at certain times both drive rollers are in contact with the pump tubing, and at other times only one drive rollers is in contact with the pump tubing, depending on the angular position of the pump rotor within the raceway. The thermal exchange fluid system volume suddenly increases when a roller from the peristaltic pump loses contact with the pump tubing as a normal part of the pump's rotation. This happens because a section of the pump tubing that had been flattened, and had zero cross-sectional area, suddenly becomes round and contains a non-zero cross-sectional area. The increase in system volume is approximately the cross-sectional area of the tubing in its round state multiplied by the length of tubing flattened by the roller. The pulse dampener should have enough flexibility to contract suddenly and decrease its volume by approximately this amount in order to dampen the pulse. For example, the volume gained by the pump tubing when a roller leaves contact with it may be 2 to 3 mL. Therefore it is desirable for a pulse dampener to be able to decrease its volume by this amount with a minimal change in system pressure. The pulse damping conduit may comprise, for example, tubing that has sufficient elastic or flexural properties to dampen, attenuate or reduce the amplitude of pulses in the thermal exchange fluid as it flows therethrough. For example, if the conduit is able to expand by a volume of 20 to 30 mL under 60 psi of pressure, then it will be able to contract by 2 to 3 mL when the pressure drops by approximately 6 psi. The more compliant the conduit is, the smaller the pressure drop that occurs when the tubing contracts, and therefore the better the conduit performs its damping function. While a highly compliant tubing is desirable, at the same time, the conduit should have sufficient mechanical strength to expand and contract by this amount repeatedly without rupture. For example if a peristaltic pump has two driving rollers, turns at 40 RPM, and a procedure lasts for 12 hours, the conduit must withstand 57,600 pulsation cycles. To balance these conflicting requirements, for example, in certain embodiments, the length of the pulse damping conduit may be about 90" and could range between 20" and 100". The conduit may be made of a low durometer polyurethane (Prothane II 65-70A) and have a large ID at 0.25" and could range between 0.15" and 0.40". The wall thickness of the conduit is about 0.094" and could range between 0.06" and 0.25".

As seen in FIGS. 26 and 27 the cassette housing 62 is connected to the frame 69 by a hinged connection 200. As packaged prior to use, the hinged connection 200 is in a closed configuration so that the housing 62 and accompanying pump tubing 65 are folded over the cassette's flexible vessel or bag 63 in the manner seen in FIG. 27. At the time of use, the hinged connection is moved to an open configuration causing the housing 62 and accompanying pump tubing 65 to extend at a substantially right angle relative to the expandable vessel or bag 63, as seen in FIG. 26. The hinged connection 200 locks in such open position so that the cassette 64 cannot be returned to the folded configuration seen in FIG. 27 without removing, disrupting or altering the hinged connection 200. For example, the hinged connection may be unlocked or disengaged by sliding a hinge protrusion forward or backward within a hinge slot, thereby disengaging the lock.

Details of the sensor module 34 are shown in FIG. 29. The sensor module comprises upper and lower housing portions 302a, 302b which, in combination, form an enclosed housing. Within the housing there is positioned an electronic storage medium 310 which holds encoded information. Examples of the types of encoded information that may be stored include but are not limited to; unique identifier(s) for the changeable components (e.g., manufacturer identification, part number, lot number, etc.), indications of whether the changeable component(s) have previously been used (e.g., an encoded indication of first use), indications of whether the changeable component(s) is/are expired (e.g., encoded expiration date), operational characteristic(s) of the changeable component(s) (e.g., encoded indications of the size, type, volume, etc. of the changeable component(s). In this non-limiting example, the electronic storage medium comprises electrically erasable programmable read-only memory (EEPROM). One example of how the controller may check to determine whether the components had previously been used is by checking the EEPROM or other data storage medium 310 for a First-Use date. The First-Use date would be "EMPTY" if this is the first time the changeable component (e.g., the cassette assembly) has been connected to a console 14. If the First-Use date is "EMPTY", the controller will write the current date to the EEPROM's memory location where the First-Use date will then be stored. Also, within the housing of the sensor module 34, there are provided a first temperature sensor (e.g., a thermistor) for sensing the temperature of thermal exchange fluid flowing to the catheter 12 and a second temperature sensor 300b (e.g., a second thermistor) for sensing the temperature of thermal exchange fluid returning from the catheter 12. Signals from these first and second temperature sensors 300a, 300b, as well as body temperature signals from the connected body temperature sensor TS and encoded data from the electronic storage medium 310, are transmitted through temperature lead TL. A pressure lead PL, which carries signals from a pressure sensor that senses the pressure of thermal exchange fluid within the cassette tubing or console 14, combines with the temperature lead TL, as shown, and the combined leads are connected to the control console 14. In this manner, the controller in the console main housing receives signals indicating a) the encoded data from the electronic storage medium 310, b) subject body temperature, c) thermal exchange fluid temperature flowing to catheter, d) thermal exchange fluid temperature flowing from catheter and e) thermal exchange fluid pressure. The controller may be programmed to use the encoded information and/or sensed temperatures and/or sensed pressure for control of the system 10 and/or for computation/display of data. For example, the controller may be programmed to use the difference between the sensed temperature of thermal exchange fluid flowing to the catheter and the sensed temperature of thermal exchange fluid flowing from the catheter, along with the fluid flow rate or pump speed, to calculate the Power at which the body heat exchanger is operating or the power output of the heat exchanger. Power may be calculated by the following equation: Such Power may be displayed on the display or user interface 24.

$$\text{Power(Watts)} = (\text{HE Fluid Temp OUT} - \text{HE Fluid Temp IN}) \cdot \text{Flow Rate} \cdot \text{CP}$$

wherein:
HE Fluid Temp IN is the current measured temperature of heat exchange fluid flowing into the heat exchanger 18;
HE Fluid Temp OUT is the current measured temperature of heat exchange fluid flowing out of the heat exchanger;
Flow Rate is the measured or calculated flow rate of heat exchange fluid through the heat exchanger; and
CP is the specific heat capacity of the heat exchange fluid.

Also, the controller may be programmed to check and accept the encoded information from the electronic storage medium 310 before allowing the system 10 to be used for warming or cooling the body of the subject and/or to adjust operating variable or parameters to suit operative characteristics (e.g., size, operating volume, type) of the catheter 14, cassette 64, temperature probe, tubing or other components. This pre-check of the encoded information may occur in various sequences or processes. One example of a process by which this pre-check may occur is by the following steps:

1. User connects tubing/cassette/sensor module assembly 60 to control console 14.
2. Console controller detects this connection. Such detection of the connection may occur by the controller scanning the temperature sensor channels, which will open channels when no tubing/cassette/sensor module assembly 60 is connected but will become non-open when a tubing/cassette/sensor module assembly 60 is connected. Alternatively, this could be done by the controller polling the pressure sensor in the cassette 64 or the EEPROM in the sensing module 34 for a response.
3. Controller establishes a secure communication session with the EEPROM and reads its content. The EEPROM's content may be encrypted such that it is readable only by a processor having a secret key. In some embodiments, the EEPROM itself may be encoded with a secret key such that the controller may establish a secure session in connection with the sensing module 34.
4. In some embodiments, the EEPROM content may comprise the following information, some or all of which must be checked and verified/accepted by the controller before priming and operation of the system 10 may occur:
   a. Manufacturer ID (factory written)
   b. Cassette part # (factory written)
   c. Shelf-life Expiration date (factory written)
   d. Lot # (factory written)
   e. Expiration duration since first use (factory written)

f. First-Use date (written when the cassette is first plugged into the console)

Referring to FIG. 38, in some embodiments, the system 10 may be configured and programmed to alternately operate with more than one type of heat exchange device. In such embodiments, the system controller may be programmed to detect the particular type of heat exchange device or component that has been connected to the system and adjust the system's operation in accordance with the detected type of heat exchange device or component, e.g., tubing/cassette/sensor module assembly 60 or cassette assembly, and/or heat exchange device or component or body heat exchange device or component, e.g., catheter 12 or a body surface heat exchanger. For example, electronic storage medium 310 may include information identifying a particular model or size of cassette assembly 60 or heat exchange catheter 12 that is used in combination with the cassette assembly 60. The system controller may determine from that information the particular model and/or size of cassette assembly or heat exchange catheter 12 being used. The system user interface may be modified or altered depending on the particular cassette assembly or catheter identified. The controller may determine the number/location/type of patient temperature sensors used with that particular cassette assembly 60 or catheter, select and actuate a control algorithm e.g., temperature control algorithm, that is appropriate for the detected type and/or size of cassette assembly 60 or catheter 12 and set limits or parameters, such as maximum pressure limits, suitable for the detected type and/or size of cassette assembly 60 or catheter 12. The patient temperature sensors, e.g., patient temperature sensors A or B in exemplary FIG. 38, may include patient blood sensors, tissue sensors and/or deep tissue sensors, and such sensors may be positioned on or through a catheter or in remote location. Selection of the control algorithm may include selection of any control algorithm described herein and/or selection of whether the heat exchange rate is to be varied by a) altering the temperature of thermal exchange fluid being circulated through the catheter, altering the flow rate of thermal exchange fluid being circulated through the catheter and/or altering both the temperature and flow rate of thermal exchange fluid being circulated through the catheter. In certain embodiments, the above steps or actions may be performed for a body surface heat exchanger, e.g., a pad, based on e.g., identifying information of the pad and or associated cassette. Moreover, although the diagram of FIG. 38 shows only two possible cassette assemblies and catheters (i.e., Cassette Assembly A, Cassette Assembly B, Catheter A or Catheter B), it is to be appreciated that the electronic storage medium 310 may include information identifying any number of cassette assemblies, catheters or other body heat exchange devices, e.g., body surface heat exchangers or pads, that are alternately useable with the system 10. For example, the electronic storage medium 310 may include information identifying each of the following cassette assemblies and/or catheters:

| | |
|---|---|
| Catheter A | The catheter 12 shown in FIGS. 32 through 33C and described herein |
| Catheter B | Cool Line ® Catheter (ZOLL Circulation, Inc., San Jose, California) |
| Catheter C | Icy ® Catheter (ZOLL Circulation, Inc., San Jose, California) |
| Catheter D | Quattro ® Catheter (ZOLL Circulation, Inc., San Jose, California) |
| Catheter E | Solex 7 ® Catheter (ZOLL Circulation, Inc., San Jose, California) |
| Catheter F | InnerCool ® RTx Accutrol Catheter (ZOLL Circulation, Inc., San Jose, California) |
| Catheter G | InnerCool RTx Standard Catheter (ZOLL Circulation, Inc., San Jose, California) |
| Cassette Assembly A | Cassette assembly associated with Catheter A |
| Cassette Assembly B | Cassette assembly associated with one or more of Catheters B-G |

In some embodiments, a particular tubing/cassette/sensor module assembly 60 (a "first" cassette assembly) may be useable or approved for use with only one type of body heat exchanger. In such embodiments, the sensing module 34 may be encoded with information that is specific not only to the first cassette but which also includes or causes the system controller to use algorithms and/or operational settings/variables that are specific to the particular body heat exchanger type, e.g., catheter type or body surface heat exchanger (e.g., pad or garment) type that is useable or approved for use with that first cassette assembly 60. In other embodiments, an example of which is shown in FIG. 39, the first cassette assembly 60 or another cassette assembly 60a (a "second" cassette assembly) may be useable or approved for use with a plurality of different types of body heat exchangers, such as heat exchange catheters or body surface heat exchangers, e.g., heat exchanging blankets, pads or garments. In such embodiments, the sensing module 34 may be encoded with information that is specific not only to the cassette but which also includes or causes the system controller to use algorithms and/or operational settings/variables that are specific to the particular body heat exchanger, e.g., catheter type or body surface heat exchanger (e.g., pad or garment) type that is useable or approved for use with that cassette assembly. In the particular non-limiting example shown in FIG. 39, the second cassette assembly 60a is alternately connectable to and useable with a plurality of different types of approved heat exchange catheters 12a, 12b, 12c and 12d. In this particular example, the first approved heat exchange catheter 12a shown in FIG. 39 is commercially available as the Cool Line® Catheter (ZOLL Circulation, Inc., San Jose, Calif.), the second approved heat exchange catheter 12b is commercially available as the Solex 7® Catheter (ZOLL Circulation, Inc., San Jose, Calif.), the third approved heat exchange catheter 12c is commercially available as the Icy® Catheter (ZOLL Circulation, Inc., San Jose, Calif.) and the fourth approved heat exchange catheter 12d is commercially available as the Quattro® Catheter (ZOLL Circulation, Inc., San Jose, Calif.). Although these different types of catheters may have different operating parameters (e.g., different maximum fluid pressure ratings) they are all approved for use with cassette assembly 60a and the sensing module 34 of cassette assembly 60a may contain encoded information which includes, or which causes the system controller to select and use, algorithms and/or operational settings/parameters that are suitable for any of these heat exchange catheters 12a-12d. Specifically, the encoded information in the sensing module 34 may include the particular algorithms and/or operational settings/parameters to be used, or alternatively the system controller may be pre-programmed with a number of different algorithms and/or operational settings/parameters and may be further programmed to select and implement, on the basis of the encoded cassette information, the algorithm and/or operational settings/parameters suitable for the catheter or catheters that are useable or approved for use with the inserted cassette assembly 60 or 60a. For example, in certain embodiments, each of the plurality of approved body heat exchangers, e.g., catheters, may have a recommended pressure limit and a cassette's encoded information may include, or cause the controller to select and use, a control algorithm, operational setting or parameter that limits the speed of a pump such that heat exchange fluid pressure within the body heat exchanger connected to the cassette will not exceed a maximum pressure limit for that body heat exchanger, irrespective of which of the plurality of body heat exchanger types is connected to the cassette.

In other embodiments, the body heat exchanger, e.g., catheter or body surface heat exchanger such as pad or garment, may contain encoded information which includes, or which causes the system controller to select and use, algorithms and/or operational settings/parameters suitable for the particular body heat exchanger. Specifically, the encoded information in the body heat exchanger may include the particular algorithms and/or operational settings/parameters to be used, or alternatively the system controller may be pre-programmed with a number of different algorithms and/or operational settings/parameters and may be further programmed to select and implement, on the basis of the encoded body heat exchanger information, the algorithm and/or operational settings/parameters suitable for the particular body heat exchanger. Encoded information that is specific to a cassette or body heat exchanger may also cause a change in the user display of the console or system, which corresponds to the algorithms or operational settings/parameters for the cassette or body heat exchanger. FIG. 30 is a schematic diagram of the endovascular heat exchange system 10. This schematic diagram shows major components of the system 10, including the console 14, heat exchange catheter 12, thermal exchange engine 108, console head/user interface 24, thermal exchange plates 80 and cassette 64. Additionally, this schematic diagram includes other components and functional indicators labeled according to the following legend:

| | |
|---|---|
| FS | FLOW, SALINE |
| FW | FLOW, WATER |
| LS | LEVEL, SALINE |
| LW | LEVEL, WATER |
| PSR | PRESSURE SWITCH, REFRIGERANT |
| PS | PRESSURE, SALINE |
| S | SWITCH |
| TACH | TECHOMETER |
| TA | TEMPERATURE, AIR |
| TR | TEMPERATURE, REFRIGERANT |
| TP | TEMPERATURE, PLATE |
| TS | TEMPERATURE, SALINE |
| TW | TEMPERATURE, WATER |

To set up the system 10 a new tubing/cassette/sensor module assembly 60 or cassette assembly is obtained and removed from its packaging and the cassette 64 is unfolded to the opened and locked configuration seen in FIG. 26. The access cover 42 of the control console 14 is opened. An "open" button is pressed on the touch screen user interface 24 causing the pump 70 to shift to its loading configuration as seen in FIG. 23. The cassette frame 69 and expandable vessel or bag 63 are inserted downwardly into the cassette receiving space 66 until the housing 62 abuts front plate 172. The pump tubing 165 is inserted within the pump raceway 162. The access cover 42 is then closed and a "close" button is depressed on user interface 24 causing the pump 70 to shift to the operative configuration (FIG. 22). The user then presses a "prime" button on user interface 24 to prime the system with thermal exchange fluid from a bag or other container that has been hung on bracket 48 and connected to the system 10.

After the system has been primed, the catheter 12 is connected and inserted into the subject's body and the system 10 is operated to warm or cool the subject's body as desired.

FIG. 31 is a schematic diagram of an example of a heat exchange system 10a capable of providing endovascular and/or body surface heat exchange. The system includes all of the elements described in the system 10 of FIG. 30 and, like FIG. 30, includes labeling according to the legend set forth above.

Additionally, this system 10a includes a body surface heat exchange fluid circuit 400 such that the system can provide body surface heat exchange by circulating warmed or cooled heat exchange fluid through at least one body surface heat exchanger 402 (e.g., a heat exchange pad, blanket, garment, etc.) Such operation of the body surface heat exchange fluid circuit 400 and body surface heat exchanger 402 may be performed in addition to or instead of endovascular heat exchange. The body surface heat exchange fluid circuit includes a fluid reservoir, a pump, a bypass valve, a vent valve, thermal exchange plates and a body surface heat exchange device, e.g., a pad. A fluid, e.g., water, is added to the fluid reservoir. When the bypass valve is closed to the vent valve and open to the bypass line, fluid circulates from the pump, through the body surface fluid chambers in the thermal exchange plates, the reservoir, the bypass valve, and back into the pump. This allows the volume of fluid within the system to come to thermal equilibrium with the thermal exchange plates, which may be useful in preparing the device to deliver temperature management treatment to the patient. In normal operation, the bypass valve is open to the vent valve and the vent valve is closed, and fluid circulates from the pump, through the body surface fluid chambers in the thermal exchange plates, through the reservoir, bypass valve, and vent valve, to the body surface heat exchange device and then back through the pump. To drain the body surface heat exchange device, the vent valve is opened which allows air into the circuit and prevents fluid from flowing from the bypass valve. This forces fluid out of the body surface heat exchange device to the pump. The pump is a positive displacement pump capable of pumping air or liquid through the body surface fluid chambers in the thermal exchange plates, to the reservoir. The reservoir is open to ambient air (to allow excess air to escape the system if introduced by the draining process or normal operation, or to accommodate changes in fluid volume due to thermal expansion) and includes a fill port or drain. The circuit also includes body surface heat exchange fluid temperature sensors to provide feedback to the controller, and fluid temperature sensors and fluid flow sensors for use in power calculations.

In certain embodiments, one or more of the systems described herein may also include one or more physiological alarms and/or technical alarms. The physiological alarms may appear next to the patient's temp on the display screen, and may occur when the patient temperature exceeds the high or low patient temperature alarm value. Technical alarms may appear elsewhere on the display screen and may be triggered by console errors or other events, e.g., probe or catheter disconnection, saline loop overpressure, pump malfunction or open lid, and may be displayed by priority. Any of the alarms may be audible. The system may also transmit data, including patient and/or treatment data wirelessly, e.g., via Wifi, Bluetooth or other wireless connection. Data may also be transmitted via USB, Ethernet or wired connection. The system may be electrically powered or battery powered.

The endovascular temperature management system 10 described in various embodiments herein is a high powered system, capable of rapidly cooling a patient.

In certain embodiments, the cassette/console is designed and configured such that it is capable of delivering ≤4° C. working fluid or saline at a rate of ≥600 mL/min, at steady state, when up to 700 W of heat is added to the working fluid or saline loop (e.g., heat added by the subject's body).

In certain embodiments, the cassette/console is designed and configured such that it is capable of delivering ≤4° C. working fluid or saline at a rate of 220+−20 mL/min, at steady state, when ≤70 W of heat is added to the working fluid or saline loop (e.g., heat added by the subject's body).

In certain embodiments, the cassette/console is designed and configured such that it is capable of delivering ≥42° C. working fluid or saline at a rate of >400 mL/min, at steady state, when up to 200 W of heat is removed from the working fluid or saline loop.

In certain embodiments, the system (cassette, console, and catheter) is designed and configured such that it is capable of delivering greater than 400 Watts, or greater than or equal to 500 Watts, or greater than or equal to 600 Watts of cooling power, e.g., with ≤4° C. working fluid or saline at a catheter pressure of about 60 PSI. In certain embodiments, the system may deliver from 500 to 700 W or 600 to 700 W of cooling power or about 675 W of cooling power or greater than 700 W of cooling power.

In certain embodiments, the system (cassette, console, and catheter) is designed and configured such that it is capable of delivering > or equal to 50 W of warming power e.g., with >37° C. working fluid or saline at a catheter pressure of about 40 PSI.

In certain embodiments, the system performance parameters were verified during a bench test. The bench test included placing a catheter (which is connected to a console/cassette assembly) in a rigid 22 mm ID tube, which simulates the average IVC (inferior vena cava) diameter, through which water at a temperature of 37 degrees C. is flowing at a rate of 2.5 liters per minute (simulating blood flow) over the catheter in a direction from the proximal end of the catheter to the distal end of the catheter.

In certain embodiments, in maintenance and controlled rate warming, the system may control a stable patient's temperature, as measured by console, within about 0.3° C. of target when using a temperature sensor or probe on or in the catheter. During normal use and in the case of a sudden saline loop blockage, the system shall regulate and limit working fluid or saline pressure for catheters as follows: <20 C: 60 psi nominal, 90 psi limit; >=20 C: 40 psi nominal, 70 psi limit; or 40 psi nominal, 70 psi limit. The console working fluid pump and cassette shall be capable of an output up to 600 mL/min at 70 psi. Saline or working fluid pressure at the outlet of the saline pump may be measured, e.g., over a range of 0-100 psi with an accuracy of ±5 psi over the range 10-70 psi. The system may be used concurrently with a defibrillator, electro surgical unit or other device or during an MRI. The console and cassette together may be capable of delivering <8° C. saline, at a rate of 600 mL/min, within 5 minutes of turning on the console, when starting with the system equilibrated to ambient temperature. The console and cassette together may be capable of changing the temperature from 4° C. to 40° C. within 10 minutes.

Supplemental Warming by Hot Gas Bypass

With reference to FIG. 34, at least some embodiments of the system 10 may include a hot gas bypass circuit and controller/processor(s) programmed to cause hot refrigerant to circulate from the refrigeration system of the cooling engine 108 through the thermal exchange plates 80 to assist the heaters 82 when conditions are deemed to indicate that such assistance of the heaters 82 is appropriate. When the system 10 requires less cooling than what the cooling engine provides when the compressor is at the minimum speed, the heater(s) 82 are operative to warm the thermal exchange plates 80. An indicator of the warming power output of the heater(s) 82 is monitored. So long as the warming power expended by the heater(s) 82 remains below a predetermined limit, the system 10 will continue to operate with only the heater(s) 82 warming the thermal exchange plates 80. However, if the warming power output of the heater(s) 82 exceeds a predetermined limit, the controller(s) will cause hot refrigerant to circulate from the refrigeration system of the cooling engine 108 through the hot gas bypass circuit and through the thermal exchange plates 80, thereby assisting the heaters 82 in warming the thermal exchange plates 80. The amount of assistance the given to the heaters by the hot gas bypass circuit is determined by the duty cycle of the hot gas bypass being open vs being closed. When the monitored heater power falls below the predetermined limit, the controller(s) may then incrementally or progressively reduce the hot gas bypass valve duty cycle (BVDC) to facilitate the correct amount of cooling or warming of the subject body temperature to the target temperature without significant overshoot of the target temperature.

To provide incremental or continuous change of the amount of supplemental heating provided by the hot gas bypass, the controller in some embodiments of the system 10 may be programmed to vary duty cycle of the hot gas bypass as the monitored power output of the heater(s) 82 changes. For example, if the maximum heating power output of the heater(s) 82 occurs at a heater duty cycle (HDC) of 30%, the predetermined limit may be set at an HDC of 15% (i.e., one half of the maximum possible heater output). The hot gas bypass circuit may be operative to deliver hot refrigerant to the thermal exchange plates 80 on a hot gas bypass valve duty cycle (BVDC). For example, at a BVDC of 50%, a bypass valve would open for a period of 50 seconds to allow a 50 second flow of hot refrigerant to the thermal exchange plates 80 and would then close for a period of 50 seconds to halt the flow of hot refrigerant to the thermal exchange plates 80 for a subsequent period of 50 seconds, etc. Once the monitored heater power has exceeded the 15% HDC predetermined limit, the controller will trigger the bypass circuit to begin delivering hot refrigerant to the thermal exchange plates 80. Once the flow of hot refrigerant to the thermal exchange plates 80 has commenced, the controller will cause the BVDC to increase as the HDC increases above the 15% HDC predetermined limit and will cause the BVDC to decrease as the HDC decreases below the 15% HDC predetermined limit. There may be a maximum and minimum limit of the BVDC, and the BVDC cannot exceed those limits (e.g., max of 90% and min of 0%).

Combined Variation of Heat Exchange Fluid Flow Rate and Temperature for Precision Maintenance of Target Body Temperature In some embodiments of the system 10, the controller/processor(s) may be programmed to vary not only the temperature of the heat exchange fluid being circulated through the heat exchange catheter 12, but also the rate and/or frequency of such flow. One non-limiting example of this is shown in the flow diagram of FIG. 35. In this example, after the subject has reached the target temperature and the system 10 is operating to maintain the body temperature at or within a permissible variance range of the target temperature, the system 10 holds the temperature of the heat exchange fluid constant and varies the speed of the pump 70 to adjust the flow rate of heat exchange fluid through the catheter 12 as needed to maintain the body temperature. The controller monitors the pump speed. If the pump speed exceeds a predetermined limit, the controller will then cause warming or cooling of the thermal exchange plates 80 to adjust the temperature of the heat exchange fluid as needed to reduce the pump speed to the predetermined limit. This allows for optimal combination of flow rate and temperature adjustment during the maintenance phase of a treatment session. It is to be understood that this applies only so long as the system is continuing to cool or continuing to warm in order to maintain the body temperature. If it becomes necessary for the system to switch from cooling to warming or from warming to cooling, the controller will adjust the temperature of the heat exchange fluid irrespective of whether the pump speed has exceeded the limit.

For example, after the system 10 has cooled a subject to a target body temperature of 32 degrees C., the subject's body may tend to rewarm. Thus, the system will operate in cooling mode to maintain the target body temperature against the body's inherent tendency to rewarm. In doing so, the system will maintain a constant temperature of heat exchange fluid and will vary the speed of the pump 70 as needed to maintain the target body temperature. However, if it becomes necessary for the pump 70 to run at a speed that exceeds a predetermined limit, the controller will cause the cooling engine 108 to reduce the temperature of the heat exchange fluid by an amount which will allow the pump to slow to a predetermined limit while still maintaining the target body temperature.

Pressure Feedback

As described, the heat exchange catheter system 10 may incorporate pressure sensor(s) for sensing the pressure of the circulating heat exchange fluid. During a given treatment session, over-pressurization events can occur. This is when the saline pressure is above the saline pressure predetermined limit. Such over-pressurization events are typically of a transient nature and result from temporary compression or bending of the catheter 12 or associated tubing, or other causes. During a given treatment session, under-pressurization events can also occur. Such under-pressurization events occur when the Saline Pump Maximum Set Point (SPM_set) is reached, meaning the saline pump is not allowed to move any faster, but the saline pressure is below the saline pressure predetermined limit. When an over-pressurization or under-pressurization event of significant magnitude occurs, it may be desirable to adjust SPM_set. However, it is preferable not to abruptly change or overly reduce/ increase the pump speed. Additionally, after a transient over-pressurization or under-pressurization event has past, it is desirable to return the speed of the pump 70 to optimal operating speeds to maintain normal pressurization of the circulating heat exchange fluid.

FIG. 36 is a flow diagram illustrating the SPM_set adjustment protocol that some embodiments of the system 10 may be programmed to perform. The system 10 is equipped to sense the temperature of the heat exchange fluid, and the heat exchange fluid is classified as "cold" or "hot". In this non-limiting example, the predetermined limit for "cold" heat exchange fluid is set at 60 pounds per square inch (psi) and the predetermined limit for "hot" heat exchange fluid is set at 40 psi. The SPM_set will only be adjusted if the saline pressure is above the predetermined limit or the saline pump set point is equal to SPM_set. The controller will cause the SPM_set to decrease if the saline pressure is above the pressure predetermined limit, and will cause the SPM_set to increase as the saline pressure is below the pressure predetermined limit. There may be a maximum and minimum limit of the SPM_set, and the SPM_set cannot exceed those limits (e.g., max of 100% and min of 10%).

Optionally, the controller/processor(s) may also be programmed to store the most recent SPM_set for "cold" and "hot" heat exchange fluids. Thus, when the saline temperature threshold is crossed, the system 10 will switch from "cold" mode to "hot" mode, or vice versa, and upon doing so may recall and apply the recently calculated SPM_set setting for that temperature. In this example, the SPM_set adjustment protocol repeats every three seconds, however other intervals could alternatively be used.

Control of Body Cooling or Warming to Prevent Overshoot

In some situations, when warming or cooling a subject's body to a target temperature, it may be desirable to control such cooling or warming in a manner that substantially prevents or avoids overshooting the target patient temperature. For example, in embodiments of the system 10 which allow a user to select a "maximum" rate of warming or cooling, the system controller may be programmed to follow a multi-phase warming or cooling protocol, examples of which are shown in FIGS. 40 and 41. FIG. 40 is a graph of patient temperature versus time during a body warming process using a body heat exchange system as described herein. FIG. 41 is a flow diagram showing steps in one embodiment of a body warming process using a body heat exchange system as described herein. As shown in FIG. 41, a user initially inputs a Patient Temperature Set Point and a Warm/Cool Rate Set Point. If the user inputs a Patient Temperature Set Point greater than 37.8 degrees C. (e.g., 38.0 degrees C.) and a Warm/Cool Rate Set Point of greater than 0.1 degrees C. per hour (e.g., 0.5 degrees C. per hour or max), the system controller will cause the system 10 to effect the rewarming in three phases, as follows:

Phase 1—In phase 1 the system controller initially causes the system 10 to circulate heat exchange fluid through a body heat exchanger, such as a heat exchange catheter 12 or body surface heat exchanger (pad or garment), using a maximum pump speed and maximum heat exchange fluid temperature (e.g., the maximum safe temperature and flow rate for warming). The actual patient temperature is received by the controller. During phase 1, the heat exchange fluid temperature and/or pump speed may be periodically recalculated and adjusted based on feedback of the sensed patient temperature, as needed, to cause the sensed actual body or patient temperature to increase from the current temperature to a predetermined interim temperature. During phase 1, the controller may incrementally adjust the control patient temperature set point over time, e.g., from 32 degrees C. to 37.8 degrees C., at the user defined rate, e.g., at 0.5 degrees C. per hour. The pump speed and heat exchange fluid temperature used during phase 1 causes the sensed actual body or patient temperature to increase until it reaches a predetermined interim temperature, which is lower than the user-input patient temperature set point or user-input target patient temperature. In this non-limiting example the interim temperature is 37.8 degrees C. If the rate is chosen to be max, the rate at which the actual patient temperature changes during phase 1 may not necessarily be linear or constant as seen in the graph of FIG. 40. Rather, the actual rate of change of the subject's body temperature during phase 1 may, in some cases, vary due to physiological, pharmacological and/or environmental factors (e.g. patient sweating, changes in heart or respiration rate, dosing or changing infusion rate of certain drugs, changes in room temperature, changes in amount of clothing, blankets, or other warming deices, etc.). In certain embodiments, during the first phase, the heat exchange fluid may circulate through the body heat exchanger at a substantially constant temperature and flow rate/pump speed.

Phase 2—as shown in FIG. 41, when the sensed patient temperature reaches 37.8 degrees C. (i.e., the interim temperature) the controller will cause the system to begin phase 2 of the warming process. In phase 2, the system controller causes the system 10 to circulate heat exchange fluid through the body heat exchanger so as to further warm the subject's body at one or more rate(s). The overall rate of warming during phase 2 is slower than the overall rate of warming during phase 1. During phase 2, the heat exchange fluid temperature and/or pump speed may be periodically recalculated and adjusted based on feedback of the sensed patient temperature, as needed, to cause the sensed actual body or patient temperature to increase from the interim temperature to the user-input patient temperature set point of 38 degrees C., without overshooting or exceeding such target patient temperature. During phase 2, the controller may incrementally adjust the control patient temperature set point over time, e.g., from 37.8 degrees C. to the user-input patient temperature set point of 38 degrees C., at a slower rate than in phase 1, e.g. at 0.1 degrees C. per hour. Because the system controller monitors the sensed actual body or patient temperature and makes periodic (e.g., every minute) adjustments to the heat exchange fluid temperature and/or pump speed or flow rate during phase 2, such rate is precisely controlled and overshoot of the 38.0 degrees C. user-input patient temperature set point is avoided. The controller may be programmed to incrementally reduce the phase 2 warming rate as the actual body or patient temperature gets closer to the user-input patient temperature set point.

Phase 3—As shown in FIG. 41, when the sensed patient temperature reaches the user-input patient temperature set point of 38.0 degrees C., the controller will cause the system to proceed with phase 3 of the warming process to maintain the target patient temperature. In phase 3, the system controller continues to receive the actual sensed patient temperature and periodically (e.g., every minute) adjusts the heat exchange fluid temperature and/or pump speed, as needed, to maintain the sensed actual patient temperature substantially equal to the user-input patient temperature set point until such time as the user enters a "stop" command. As an alternative to a "stop" command, in some embodiments, the user may input a time period for phase 3 maintenance of the user-input patient temperature set point and the system may automatically stop the flow of heat exchange fluid through the body heat exchanger at the end of such user-input time period.

In cases where the system 10 is being used to warm a subject's body, an overall warming rate of 0.01 degrees C. per hour to 0.2 degrees C. per hour may be used during phase 2. For example, a warming rate of 0.05 degrees C. per hour to 0.1 degrees C. per hour may be used during phase 2. In cases where the system 10 is being used to cool a subject's body, an overall cooling rate of 0.05 degrees C. per hour to 1.0 degrees C. per hour may be used during phase 2.

In some embodiments, during warming, if the user-input patient temperature set point is greater than 37.8 the controller may be programmed to actually cause the heat exchange fluid to stop flowing through the body heat exchanger when the sensed actual body or patient temperature reaches 37.8 degrees C., irrespective of the user-input patient temperature set point.

In certain embodiments, an additional feature to ensure the patient temperature does not exceed 38.0 degrees C. may be provided. If the actual patient temperature is higher than 38.0 degrees C. and the saline temperature is determined to be higher than 38.0 degrees C., the saline pump will turn off. This prevents warming of the patient when the actual patient temperature is above 38.0 degrees C.

Hypothermic Treatment to Deter Reperfusion Injury

FIG. 26 shows one example of a clinical protocol that may be used to effect rapid hypothermia to deter reperfusion injury in a subject suffering from an ischemic event that may be treated in a manner that causes reperfusion or restoration of blood flow to the ischemic tissue. Non-limiting examples of such reperfusion procedures include angioplasty, stenting, atherectomy, embolectomy, thrombectomy, insertion of a perfusion wire or other conduit to carry blood or oxygenated fluid through or past an obstruction, administration or a thrombolytic agent (e.g., streptokinase or tissue plasminogen activator), some types of surgical revascularization, etc. While reperfusion treatments may restore a flow of blood or other oxygenated fluid to the ischemic tissue, they can also result in significant reperfusion injury which contributes to the amount of tissue that is ultimately infarcted or caused to become necrotic due to the ischemic event. Reperfusion injury is thought to occur in stages. Initially, the ischemia causes increased permeability of capillaries and arterioles. When reperfusion is accomplished, the renewed pressure within those damaged capillaries and arterioles results in diffusion and filtration of fluid into the adjacent tissue. This causes chemical imbalances within the tissue that give rise to an inflammatory response. These events and possibly others result in post-reperfusion damage to the tissue that may be permanent.

As explained herein, the above-described heat exchange catheter system 10 has the unique ability to cool an adult human subject's body to a hypothermic temperature below 34 degrees C., and preferably between 32 degrees C. and 34 degrees C., in approximately 20 minutes. This rapid induction of hypothermia allows caregivers to select an appropriate time to perform the reperfusion procedure after the subjects body temperature has been lowered to the target temperature. Prior studies have indicated that if hypothermia below 35 degrees C. is effected prior to reperfusion, the severity of reperfusion injury, and hence the size or severity of any permanent tissue infarction, is reduced. Applicant has performed a pilot study using the above-described protocol for deterrence of reperfusion injury in human subjects presenting at hospital emergency departments suffering from acute ST elevation myocardial infarction (STEW). In this pilot study, subjects were randomized into hypothermia and non-hypothermia (control) groups. Subjects in the hypothermia group received standard anti-shivering medication and a heat exchange catheter was placed in the inferior vena cava (IVC). A high power heat exchange catheter system was then used to rapidly cool the body of each subject in the hypothermia group to a temperature below 34 degrees C. within <90 minutes of the subject's arrival in the emergency department. Each subject then underwent percutaneous coronary Intervention (PCI) resulting in reperfusion of the ischemic myocardium. The subjects in the hypothermia group had a body temperatures at the time of reperfusion (i.e., measured at PCI wire crossing) of 33.6+1.0 degrees C.

Following completion of the reperfusion procedure, hypothermia was maintained in each hypothermia group subject for a period of three hours at a target temperature setting of 32 degrees C. Thereafter, the hypothermia group subjects were gradually rewarmed to a body temperature of 36 degrees C.

Four to six days after the event, each subject underwent cardiac magnetic resonance imaging (cMR) and infarct size divided by left ventricular mass (IS/LVM) was determined. On average, subjects in the hypothermia group had a 7.1% absolute change in IS/LVM and approximately a 30% relative reduction compared to the non-hypothermia controls. A 5% absolute change in IS/LVM is generally viewed as a good clinical outcome.

The results of this pilot study, when compared with previously reported data, suggests that 1) cooling of the subject's body temperature at a faster rate (i.e., made possible by using a high cooling power system) results in reduced infarct size measured as IS/LVM, 2) There appears to be a dose-response relationship whereby lower body temperature at the time of reperfusion correlates with greater protection against reperfusion injury and, thus, smaller infarct size.

Accordingly, a method for reducing reperfusion injury in a human or animal subject who undergoes a reperfusion procedure following an ischemic event (e.g., myocardial infarction, acute coronary syndrome, stroke, infarction or ischemia of any metabolic tissue or organ including but not limited to heart, lung, kidney, liver and brain) is provided. In this method, the heat exchange catheter 12 is inserted into the subject's vasculature and the system 10 is used to lower a body temperature of the subject to a temperature below 34 degrees C. and preferably between 32 degrees C. and 34 degrees C. prior to reperfusion. The above described techniques for estimating body temperature at a target location may be utilized in this method and the target location may be in or near the organ or tissue where the ischemia is occurring. For example, in a subject suffering from an evolving myocardial infarction of myocardial ischemia, the system 10 may operate to lower the estimated cardiac temperature (LV Temperature) to the hypothermic temperature. Thereafter, caregivers may perform a reperfusion procedure at a selected time after the body temperature has been cooled to the target hypothermic temperature, thereby deterring reperfusion injury and/or reducing the amount of tissue that ultimately becomes infarcted or necrotic.

Although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A system for warming or cooling a body of a human or animal subject, said system comprising:
   an extracorporeal control console having a warming and/or cooling apparatus, a pump and a controller; and
   a cassette having a fluid flow path that is connectable to a body heat exchanger positionable on or in the body of the human or animal subject, the cassette being positionable at an operating position on or in the extracorporeal control console while connected to the body heat exchanger, wherein the pump is configured to circulate heat exchange fluid through the fluid flow path, through the connected body heat exchanger and back into the fluid flow path and wherein the warming and/or cooling apparatus is configured to warm and/or cool the circulating heat exchange fluid;
   the cassette further comprising an electronic storage medium comprising machine readable encoded information, the machine readable encoded information including cassette identifying information; and
   the extracorporeal control console further comprising a reader configured to:
      access a memory of the electronic storage medium to obtain the machine readable encoded information including the cassette identifying information; and
      read the machine readable encoded information to enable the controller to determine a cassette identity from the cassette identifying information;
   wherein the controller, based on determining the cassette identity as read by the reader, controls operation of at least a portion of the extracorporeal control console.

2. A system according to claim 1 wherein:
   the cassette is useable or approved for use with a single body heat exchanger type, and the machine readable encoded information either includes, or causes the controller to select and use, a control algorithm, operational setting, or parameter that is suitable for that single body heat exchanger type.

3. A system according to claim 2, wherein the cassette is a first cassette, the system further comprising a second cassette having a second fluid flow path that is connectable to the body heat exchanger, the second cassette being alternately positionable, instead of the first cassette, at the operating position wherein the pump is configured to circulate heat exchange fluid through the second fluid flow path, through the connected body heat exchanger, and back into the second fluid flow path, and wherein the warming and/or cooling apparatus is configured to warm and/or cool the circulating heat exchange fluid;
   the second cassette further comprising a second electronic storage medium containing second machine readable encoded information different from the machine readable encoded information;
   wherein the reader receives and reads the second machine readable encoded information; and wherein the controller controls operation of at least a portion of the extracorporeal control console based on the second machine readable encoded information.

4. A system according to claim 3 wherein:
the second cassette is useable or approved for use with a plurality of different body heat exchanger types and, wherein the second machine readable encoded information includes, or causes the controller to select and use, a given control algorithm, a given operational setting or a given parameter that is suitable for any of the body heat exchanger types useable or approved for use with the second cassette.

5. A system according to claim 3 wherein the second machine readable encoded information distinguishes the second cassette from the first cassette, and wherein the controller is configured to select and use, based on the machine readable encoded information or the second machine readable encoded information, a control algorithm, operational setting, or parameter that is suitable for one or more body heat exchangers, that are useable or approved for use of either the first cassette or the second cassette, depending on whether the first cassette or the second cassette is presently inserted in the operating position.

6. A system according to claim 3 wherein the electronic storage medium comprises a medium type selected from: non-volatile random access memory (RAM); non-volatile flash memory; electrically erasable programmable read-only memory (EEPROM); ferroelectric random access memory (FRAM); a chip-embedded storage medium, and a microchip-embedded storage medium.

7. A system according to claim 3 wherein second machine readable encoded information includes an indication that the second cassette satisfies a prerequisite requirement, and wherein the extracorporeal control console is configured to proceed with warming or cooling of the heat exchange fluid when the controller determines that the second machine readable encoded information includes the indication that the second cassette satisfies the prerequisite requirement.

8. A system according to claim 7 wherein the indication that the second cassette meets the prerequisite requirement comprises at least one of: an expiration date and an absence of an indication that the second cassette has been previously used.

9. A system according to claim 1 wherein:
the cassette is useable or approved for use with a plurality of different body heat exchanger types, wherein the machine readable encoded information includes, or causes the controller to select and use, a control algorithm, operational setting, or parameter that is suitable for any one of the plurality of different body heat exchanger types useable or approved for use with the cassette.

10. A system according to claim 9 or 4 wherein each of the plurality of approved body heat exchanger types has a recommended pressure limit and the second cassette's machine readable encoded information includes, or causes the controller to select and use, a control algorithm, operational setting or parameter that limits a speed of the pump such that heat exchange fluid pressure within the body heat exchanger connected to the second cassette does not exceed a maximum pressure limit associated with said body heat exchanger.

11. A system according to claim 1 wherein the electronic storage medium comprises a medium type selected from: non-volatile random access memory (RAM); non-volatile flash memory; electrically erasable programmable read-only memory (EEPROM); ferroelectric random access memory (FRAM); a chip-embedded storage medium, and a microchip-embedded storage medium.

12. A system according to claim 1 wherein the machine readable encoded information includes an indication that the cassette satisfies a prerequisite requirement, wherein the extracorporeal control console is configured to proceed with warming or cooling of the heat exchange fluid when the controller determines that the machine readable encoded information includes the indication that the cassette satisfies the prerequisite requirement.

13. A system according to claim 12 wherein the indication that the cassette satisfies the prerequisite requirement comprises at least one of: an expiration date, and an absence of an indication that the cassette has been previously used.

14. A system according to claim 1, wherein the body heat exchanger comprises a catheter or body surface heat exchanger.

* * * * *

UNITED STATES PATENT AND TRADEMARK OFFICE
CERTIFICATE OF CORRECTION

PATENT NO. : 11,337,851 B2
APPLICATION NO. : 16/052551
DATED : May 24, 2022
INVENTOR(S) : John Jacobsen et al.

It is certified that error appears in the above-identified patent and that said Letters Patent is hereby corrected as shown below:

In the Drawings

Sheet 31 of 49, FIG. 30, Line 5, delete "Condensor" and insert --Condenser--
Sheet 35 of 49, FIG. 31, Line 5, delete "Condensor" and insert --Condenser--
Sheet 40 of 49, FIG. 34, Line 1, delete "(10" and insert --(10)--
Sheet 41 of 49, FIG. 35, Line 11, delete "Exchage" and insert --Exchange--
Sheet 47 of 49, FIG. 40, Line 1, delete "(C)" and insert --(° C.)--

In the Specification

Column 2, Line 46, delete "not limited to;" and insert --not limited to:--
Column 2, Line 53, delete "and or" and insert --and/or--
Column 2, Line 54, delete "and or" and insert --and/or--
Column 2, Line 55, delete "component(s)." and insert --component(s)).--
Column 3, Line 13, delete "finable" and insert --fillable--
Column 4, Line 10, delete "cassette," and insert --cassette;--
Column 7, Line 18, delete "of heat of heat" and insert --of heat--
Column 7, Line 51, delete "4'C" and insert --4° C.--
Column 14, Line 2, delete "330" and insert --33C--
Column 15, Line 57, delete "130fa," and insert --1307a--
Column 16, Line 45, delete "Catheter:" and --Catheter,--
Column 21, Line 61, delete "though" and insert --through--
Column 22, Line 12, delete "paralyene," and insert --parylene,--
Column 22, Line 18, delete "h" and insert --with--
Column 22, Line 20, delete "hag" and insert --bag--
Column 22, Line 22, delete "clamps" and insert --clamps.--
Column 23, Line 29, delete "not limited to;" and insert --not limited to:--
Column 23, Line 37, delete "component(s)." and insert --component(s)).--
Column 25, Line 45, delete "and or" and insert --and/or--

Signed and Sealed this
Sixteenth Day of May, 2023

Katherine Kelly Vidal
*Director of the United States Patent and Trademark Office*

CERTIFICATE OF CORRECTION (continued)
U.S. Pat. No. 11,337,851 B2

Column 27, Line 47, delete "TECHOMETER" and insert --TACHOMETER--
Column 29, Line 58, delete "600" and insert --≥600--
Column 33, Line 10, delete "deices" and insert --devices,--
Column 34, Line 60, delete "(STEW)." and insert --(STEMI).--